US010943675B2

(12) United States Patent
Cembrowski et al.

(10) Patent No.: US 10,943,675 B2
(45) Date of Patent: Mar. 9, 2021

(54) ALTERING PATIENT CARE BASED ON LONG TERM SDD

(71) Applicants: George S. Cembrowski, Edmonton (CA); Junyi Mei, Edmonton (CA)

(72) Inventors: George S. Cembrowski, Edmonton (CA); Junyi Mei, Edmonton (CA)

(*) Notice: Subject to any disclaimer, the term of this patent is extended or adjusted under 35 U.S.C. 154(b) by 291 days.

(21) Appl. No.: 16/049,488

(22) Filed: Jul. 30, 2018

(65) Prior Publication Data

US 2019/0035490 A1 Jan. 31, 2019

Related U.S. Application Data

(60) Provisional application No. 62/538,176, filed on Jul. 28, 2017.

(51) Int. Cl.
*G16H 10/40* (2018.01)
*G16H 50/20* (2018.01)

(52) U.S. Cl.
CPC ............. *G16H 10/40* (2018.01); *G16H 50/20* (2018.01)

(58) Field of Classification Search
None
See application file for complete search history.

(56) References Cited

U.S. PATENT DOCUMENTS

| | | | | |
|---|---|---|---|---|
| 2003/0125609 A1* | 7/2003 | Becker | ................... | G16H 70/20 600/300 |
| 2005/0130321 A1* | 6/2005 | Nicholson | .............. | A61B 5/412 436/518 |
| 2007/0192134 A1* | 8/2007 | Littenberg | ............. | G16H 70/20 705/2 |
| 2007/0198213 A1* | 8/2007 | Parvin | .................... | G16H 10/40 702/179 |
| 2008/0091471 A1* | 4/2008 | Michon | .................. | G06Q 40/08 705/3 |
| 2009/0156911 A1* | 6/2009 | Rule | .................. | A61B 5/14535 600/309 |
| 2011/0240842 A1* | 10/2011 | Grant | ..................... | G01N 33/78 250/282 |
| 2011/0245634 A1* | 10/2011 | Ray | .................... | A61B 5/14532 600/309 |
| 2012/0107862 A1* | 5/2012 | Harrop | ............... | G01N 33/6893 435/29 |
| 2012/0171672 A1* | 7/2012 | Barken | ................ | G01N 33/564 435/6.11 |
| 2013/0165900 A1* | 6/2013 | Braig | ............... | A61B 5/150862 604/504 |
| 2013/0226605 A1* | 8/2013 | Miller | .................... | G16H 50/20 705/2 |

(Continued)

*Primary Examiner* — Michael Tomaszewski
*Assistant Examiner* — Jay M. Patel
(74) *Attorney, Agent, or Firm* — Schwegman Lundberg & Woessner, P.A.

(57) ABSTRACT

Generally discussed herein are systems, apparatuses, and methods that relate to altering patient care and increasing the efficacy of medical diagnostics. A standard deviation of deltas (SDD) plot of analyte measurements can provide insights into the medical diagnostics. One or more SDD plots can be used to help diagnose a patient and alter a patient's care depending on the relation of the patient's own SDD plot characteristics relative to the one or more SDD plots. Any or all of the analysis can be automated, such as to reduce human interaction with process.

20 Claims, 37 Drawing Sheets

(56) References Cited

U.S. PATENT DOCUMENTS

| | | | | |
|---|---|---|---|---|
| 2013/0297222 A1* | 11/2013 | Callicoat | ............... | G01N 33/66 |
| | | | | 702/21 |
| 2013/0323739 A1* | 12/2013 | Klem | ................ | G01N 33/5091 |
| | | | | 435/6.12 |
| 2014/0011879 A1* | 1/2014 | Baribaud | ........... | G01N 33/6893 |
| | | | | 514/562 |
| 2016/0317744 A1* | 11/2016 | Rule | ................... | G06F 19/3468 |
| 2016/0370394 A1* | 12/2016 | Cembrowski | .... | G01N 35/00693 |
| 2017/0023575 A1* | 1/2017 | Raftery | ................. | G01N 24/08 |

\* cited by examiner

ALTERING PATIENT CARE BASED ON LONG TERM SDD

RELATED APPLICATION

This application claims the benefit of priority to U.S. Provisional Patent Application No. 62/538,176 titled "Long Term Analytic and Biologic Variation" and filed on Jul. 28, 2017, which is incorporated by reference herein in its entirety.

BACKGROUND

It is estimated that as much as eight hundred fifty billion dollars is spent on needless medical procedures each year in the United States. One or more methods or devices discussed herein may help reduce the amount of money spent on wasteful medical procedures.

DETAILED DESCRIPTION

Figure 1:
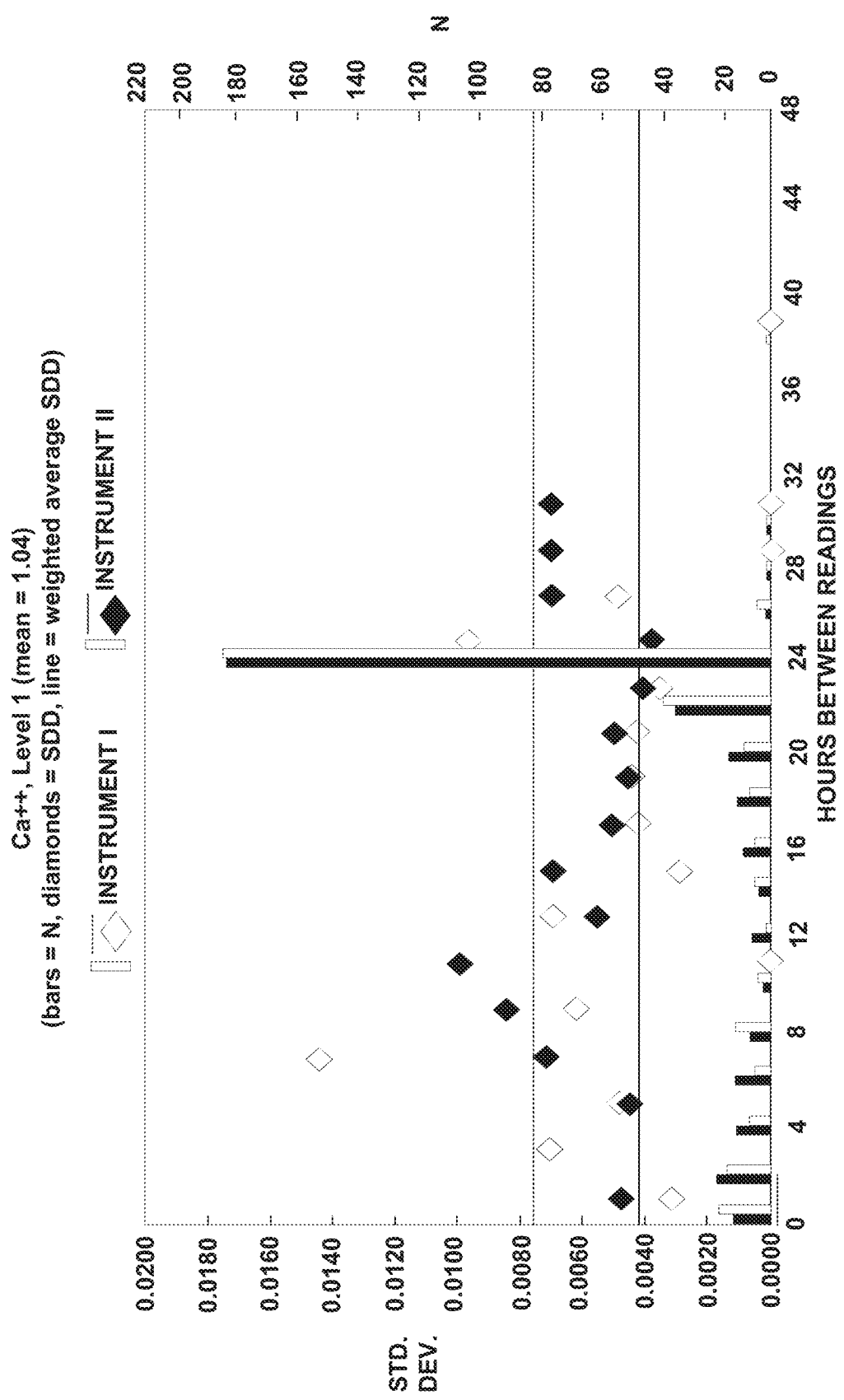
FIG. 1 illustrates, by way of example, an embodiment of an SDD graph for Level 1 Radiometer 800 QC data from 2 different instruments, represented by dark and light points, respectively.

Embodiments in this disclosure relate generally to detecting error in a laboratory analyzer, whether a test is necessary, or making a diagnosis based on one or more results from the laboratory analyzer. Methods, systems, or devices in accord with this disclosure may help in determining if a laboratory analyzer should be calibrated or otherwise requires an adjustment. Methods, systems, or devices in accord with this disclosure may help in determining the appropriateness of re-analyzing a specimen associated with an analyzer error signal. Methods, systems, or devices in accord with this disclosure may help in determining long term analytic stability (variability) and long-term patient test stability (variability) derived from quality control (QC) data or sequential patient laboratory data, respectively.

Modern laboratory equipment (e.g., chemistry analyzers, hematology analyzers, or the like) should be precise and accurate. A precise and accurate laboratory analyzer allows a doctor to have more confidence in their diagnosis. A precise and accurate laboratory analyzer helps ensure a patient that the doctor is basing their decisions on good analyte measurement data. An inaccurate analyte measurement can cause one of a variety of bad actions including: (1) ordering another analyte measurement that would be unnecessary if the original analyte measurement were accurate; (2) an improper diagnosis; (3) an improper prescription or drug treatment, such as a supplement, or the like; and (4) time and monetary costs associated with each of (1)-(3).

Laboratory analyzers may be calibrated with calibrating solutions where the calibration can be verified by an analysis of QC specimens. If the laboratory analyzer returns the value that is expected for the control specimen within a specified tolerance, then the laboratory analyzer is considered calibrated. If not, then operation of the laboratory analyzer is investigated, possibly repaired, and may be re-calibrated so that the analyzer returns a measurement of the specimen within the specified tolerance. On such systems, once the analysis of one or more QC specimens confirms that an analytical run is accurate, the laboratorian generally assumes that the prevalence of analytically defective testing is very low (sometimes called analytic variation of the laboratory analyzer). For this reason, QC specimens may be analyzed infrequently. QC specimen analysis is often used to confirm the expected absence of analytical shifts and increased random error and not to detect error. With analytic errors that are episodic (e.g., periodic and/or transient), it is possible that QC results may be within tolerance specifications, while preceding and/or subsequent analyses are defective but not detected. This problem of undetected error may be attributed, at least partially, to infrequent control analyses.

To detect these intermittent errors, QC specimens might be analyzed more frequently. Such a solution requires scheduling more tests on laboratory analyzers that may include an already full schedule, thus increasing costs and reducing the availability of the laboratory analyzer. This solution may also be expensive in terms of delays in reporting of the patient results, the additional QC material consumed, the additional test reagents consumed, and the technologist's time and effort in the follow-up of any outlying data that are detected during the analysis of the additional QC specimens.

Another solution to detect the intermittent errors may include using an adequately sensitive and specific patient data analysis technique to detect an error in a laboratory analyzer. One such technique includes monitoring inter-patient medians or averages and deviations therefrom. Such techniques may provide details regarding a distribution of patient data and characteristics of the distribution. Various data reduction schemes have been used to provide averages or medians of truncated (e.g., trimmed) patient results. Unfortunately, while the deviation of patient results from the usual average or median can signal an analytic shift, it can also indicate a change in patient constituency, an analytic bias, or a combination thereof. Another disadvantage of such median or average tracking is that it detects an analytic shift or a systematic error, but does not detect an increase in random error.

About fifty years ago, Hoffman and Waid introduced the average of normal (AON) quality control (QC) method in their paper titled "The 'average of normals' method of quality control". Using AON, test results that are determined to be within a "normal" range of expected results (e.g., within a certain standard deviation of average) were averaged and that average was used to monitor changes in the laboratory equipment and/or process of analyzing specimens. Using AON, either no error condition exists (patient average was within limits) or an error exists (patient average is outside of limits and presumably due to an analytical shift with the average of the results either increased or decreased). As laboratory results outside their usual limits tend to have repeated measurements more often than normal results, Hoffman and Waid recommended that only results within the normal range be averaged.

In 1984, Cembrowski et al. assessed AON as an analysis tool in the publication titled "Assessment of 'average of normals' quality control procedures and guidelines for implementation." The simulations performed by Cembrowski et al. showed that AON reliability depends on a number of factors such as number of samples divided by an analytical standard deviation (Sa) (i.e. the standard deviation inherent in the analysis procedure), a width of the range considered of samples considered "normal" samples, the number of "normal" samples used in determining the average after truncating samples outside of the normal range, and the range of the control limits for the average of the normal samples.

One of the most popular approaches to hematology QC is Bull's approach (also known as $X_b$, pronounced "x bar b") which uses a unique average of sequential batches of twenty patient red cell indices to demonstrate (in)stability in red cell associated Coulter measurements. The red cell indices consist of the directly measured mean corpuscular volume (MCV), the mean corpuscular hemoglobin calculated from hemoglobin (Hgb) and red blood cell (RBC) count, and the mean corpuscular hemoglobin concentration (MCHC) derived from Hgb, RBC and MCV. Too often, especially with today's highly precise hematology analyzers, these outlying average indices in hospital patients indicates the analysis of non randomized selection of patients with a high proportion of abnormal indices including neonates, renal failure patients or oncology patients undergoing chemotherapy.

In the 1980's and 1990's, review of control every twenty specimens may have had significant utility. Today, however, many more samples are being analyzed and QC review every twenty samples is cumbersome. To decrease the implicit variation of the patient average and to improve its error signaling, it may be intuitive to average more specimens. In an evaluation of patient averages, it was determined that the error-detection capabilities of patient averages depend on multiple factors with an important factor being the number of patient results averaged (N) and the ratio of the standard deviation of the patient population (sp) to the standard deviation of the analytical method (sa). Other important factors included the limits for evaluating the mean (control limits), the limits for determining which patient data are averaged (truncation limits), and the magnitude of the population lying outside the truncation limits.

In one or more embodiments, it can be beneficial to prevent the averaging of specimens with outlying results. For example, in a referral laboratory which analyzes primarily specimens from generally healthy patients, the occasional incorporation of blood from a patient with renal failure or chemotherapy will not affect the patient mean if proper truncation limits are implemented.

To monitor laboratory analyzers, either middleware or the analyzer's own software can be programmed to refrain from averaging patients from specific units (e.g., renal failure, oncology) or patients of specific ages (e.g., the neonate). Before averaging, to reduce the effect of the more frequent testing of outlying abnormal results, these data can be excluded (truncated) from averaging.

In modern day applications of averages of patient data, intermittent transient shifts in the patient averages can largely be ignored. The trouble-shooting of persistently shifted patient averages can incorporate assessment of pre-analytical as well as post analytical (e.g., laboratory information) issues. The laboratorian should have an understanding of the clinical reasons for shifts in the patient averages before assuming analytical error and adjusting analyzer parameters. It is not always clear to laboratory staff whether a persistent shift is due to a subtle patient population shift or an altered analytical process. As such, the investigation of persistent outlying patient averages can be problematic. Techniques that employ patient averaging techniques may not easily detect random error.

Stability in the laboratory analyze measurements of hospital patients can be seen in patients that are sampled (and analyzed) only once per day, such as between 0400 hours and 1200 hours in many hospitals. This stability arises from at least two different independent mechanisms: 1) for many laboratory tests, there is an implicit diurnal variation, so sampling and analyzing them on a 24-hour basis will tend to cause the least variation in their sequential results; and 2) in hospitals, patient acuity of illness is associated with more frequent testing. Thus, generally, only more stable patients will be sampled about once per 24 hours. The testing can occur in the morning because of requirements for tests in the fasting status and clinicians usually perform their testing rounds in the morning and require "fresh" laboratory results to help them determine the medical course of the patient.

The between day differences in the patient results is generally minimal. As such, the average difference of a specific analyte measurement in all the patients who have their blood sampled only in the morning hours may be close to zero unless there is a persistent error in the analyzer or there is a trend in the patient data independent of the analyzer (this may be significant in only a few analytes).

Many laboratory tests are repeated (e.g., hourly, every day, or other time frame between tests). Patients who have repeat testing at most every day (e.g., somewhere between sixteen and thirty-two hours between analyte collection) are probably quite stable and are not being aggressively treated. These patients and their corresponding measurements can provide a basis for analyzing whether an operating laboratory analyzer needs recalibration or needs to be further investigated, repaired, and/or recalibrated.

Based on a high prevalence of about 24 hour repeats (about 70% of tests area repeated within forty-eight hours) and lower biologic variation at about 24 hours, patients retested at about 24 hours can be used as their own controls. A delta can be calculated (patient 1 (0 hours)—patient 1 (16 to 32 hours later)) for each data pair. The Standard Deviation of Deltas (SDD) and/or average of deltas (AoD) can be calculated to determine systematic error in a laboratory analyzer and/or increased random error in the laboratory analyzer.

An AoD (e.g., a moving AoD) can be calculated, such as can include differences in an analyte measurement of a patient that is repeated within 16 and 32 hours. The AoD calculation is summarized as in Equation 1:

$$AoD = \sum_{i=1}^{N} \Delta_i / N. \qquad \text{Equation 1}$$

In Equation 1, $\Delta_i$ is the difference between consecutive analyte measurements of the same patient that is repeated within 16 to 32 hours and N is the number of deltas used in determining the average. If the AoD value is outside a range of acceptable AoD values, such as a standard deviation of AoD values being outside an acceptable range of standard deviation values, then an error condition can be signaled.

The deltas can be averaged, such as by using moving averages AoDs), with an AoD or a standard deviation of AoDs exceeding a threshold indicating a significant analytical shift. A significant analytical shift can mean that the laboratory analyzer requires servicing, such as usually includes re-calibration. As analytical shifts can either represent a bad shift (going from a correct to an incorrect calibration state) or a good shift (going from an incorrect to a correct calibration state), a previous average, such as a prior day's average (mean, median, AoD, or mode), can be compared to the calculated average to determine if the shift is a good shift or a bad shift. A "normal" previous average with a higher positive or negative AoD can signal a developing error. A high previous average and a lower current average of deltas can indicate a situation in which the error condition is being corrected.

The standard deviation of the AoD can be calculated as in Equation 2

$$\sqrt{\left(\sum_{j=1}^{M} (AoD_j - AoD_\mu)^2 / M\right)} \qquad \text{Equation 2}$$

In Equation 2, $AoD_j$ is a determined AoD value, such as by using Equation 1, $AoD_\mu$ is the average of the M $AoD_j$ values, and M is the number of $AoD_j$ values used in the standard deviation calculation.

A specified number of delta calculations (e.g., AoDs) can be used for each calculation, such as to help ensure statistical significance. The specified group size can vary between analytes. If the AoD calculation is out of range, such as can be indicated by the SDD exceeding a specified SDD limit, then an error flag can be turned on.

Using software modeling of patient data collected during 669 days and selecting only those samples from patients that were repeated within 16-32 hours of the previous analysis the ability of the calculation to detect a simulated significant shift in instrument performance was demonstrated.

Each analyte to be considered for monitoring by the average of deltas (AoD) can have a unique requirement for the number of pairs (deltas) of samples to be averaged (N). Similarly, each analyte can have unique limits to the magnitude of deltas or individual analyte measurements that can be included in the calculation. In order to determine a set (e.g., an optimal set) of parameters for the P oD calculation for each analyte, the patient data pairs were analyzed via a computer script that induces a user defined error at increasing intervals throughout the data stream and calculates the average number of deltas to detection (ANDD), the standard deviation of the ANDD, mode number of deltas to detection (Mode NDD) and median number of deltas to detection (Median NDD). The computer script, using a simulated annealing algorithm can stochastically select the number of patient pairs to average (N) and the allowable magnitude of the delta pairs, or truncation limits, to use to minimize the ANDD value.

The truncation limits, in effect, exclude delta values greater than or less than a set limit from the ANDD calculation. Selection of the upper truncation limits (TLU) or lower truncation limits (TLL) is intended to reduce the magnitude of the ANDD oscillations caused by large deltas. The exclusion of the larger deltas can serve at least two purposes. The first is that the AoD calculation relies on pairs of values from stable patients to determine the analytic performance of the instrument; pairs of samples with large deltas likely do not represent stable patients. The second purpose is strictly mathematical, large values when included in an average calculation will unduly pull the mean towards an extreme value. In general, the size of the allowable delta (e.g., an allowable measurement value) is a function of the difference between the concentrations of the analyte of interest between healthy and acutely ill patients, the maximal physiologically delta possible within 16-32 hours, and the magnitude of the analytical error or bias one is trying to detect.

As an example of this effect, simulations determined the truncation limits for pairs of potassium results to be 1.20 and −1.59 mmol/L in order to detect a shift of +/−0.5 mmol/L. In contrast, for Alanine Aminotransferase, simulations determined truncation limits were determined to be 31 and −16 U/L to detect a shift of +/−7 U/L.

Using this system, the N value and truncation limits for each analyte to be monitored could be determined from a stream of historical data pairs. If the AoD shifts due to an out of control instrument condition, the AoD will exceed the user defined limit and the system or device can alert laboratory personnel to the error condition. This system is a shift away from prior calibration techniques that are typically performed on a QC sample at a predefined time interval, rather than a patient's own analyte measurements. The measurements already being performed using the laboratory analyzer can be used to determine the accuracy and preciseness of the laboratory analyzer results.

Long Term Analytic Stability and Long Term Patient Test Stability

The knowledge offered previously in this application is expanded to long term variation of either QC data or repeated patient results. The long-term results may be for periods that are weeks, months, years, or longer. This long-term variation of the QC data enables charting of QC data. This data may help a laboratorian distinguish adequately accurate laboratory tests from tests that exhibit excess analytic error. This information may ultimately decrease a test's monitoring or diagnostic capability. The long-term variation of repeated patient results may help establish statistical limits for distinguishing acceptable (normal results) from results that would define variation associated with disease or altered physiology.

While the scientific community has attempted to define these zones of usual and acceptable variation, they have done it with simplistic models which do not incorporate factors such as fasting/nonfasting, short term variation (for example diurnal variation), seasonal variation, and abnormally high analytic variation. Models discussed herein may incorporate all, or just a portion of these parameters, thus providing a more realistic approximation of patient variation.

In previous work, an approach was presented for summarizing the short term (ST) and intermediate term variation in repeated measurements, including both a) repeated QC results arising from the analysis of a series of apparently identical samples over days or months or b) the analysis of patient specimens, obtained repeatedly from patients along with time of procural or time of testing, usually associated with the patients' care. The serial QC results and the time of testing are used to determine the average short term analytic (analyzer-associated) variation. Graphing the variation of the serial patient results against the time of procural or testing can be used to determine the statistical sum of the short term analytic (instrument associated) variation and the biologic (patient associated) variation. If two of these three terms are known, (e.g., the biologic variation and the statistical sum of the short term analytic and biologic variation) then the other term can be computed (e.g., the analytic variation).

The determination of the short-term QC or patient variation can require large numbers of consecutive QC data or large numbers of consecutive intra-patient data, respectively. Assume the series of observations (e.g., analyte measurements) is represented by $x_1t_1, x_2t_2, x_3t_3 \ldots$ where $t_1$ represents the time of analysis of the first specimen, $x_1$, $t_2$ represents the time of analysis of the next specimen, $x_2$, and $t_3$ represents the time of analysis of the third specimen, $x_3$. After all the data are collected they can be arranged in pairs of temporally consecutive results: $(xt_1, xt_2), (xt_2, xt_3), \ldots, (xt_{2i-1}, xt_{2i}) \ldots (xt_{2n-1}, xt_{2n})$. Result pairs can be gathered into period bins that reflect the interval of time between consecutive tests. The intervals could be as short as 1 or 2 hours or as long as years. If the intervals were spaced into 2 hour increments, then the time interval between successive tests would include 0 to 2 hours, 2 to 4 hours, 4 to 6 hours, etc.

For each time interval, the standard deviation of duplicates (SDD) can be calculated for all of the QC pairs or intra-patient test pairs within that interval: for the quality control data, the SDD vs time line seems to be linear with a slope close to zero. This zero slope can be attributed to the stability of calibration and the accuracy of the calibration process. The y-intercept corresponds to the average imprecision of that control.

For the patient data, it was found that the SDD vs time line is generally linear over the initial shorter intervals that a test is repeated. For longer time intervals the data become curvilinear. The shape of the curve and the mathematical interpretation is presented herein. For the QC data, if the SDD is regressed against the time intervals, the y-intercept ($y_0$) represents the average analytic (instrument) variation $s_a^2$. For the intra patient data, if the SDD is regressed against the time intervals, the y-intercept $(y_0)^2$ represents the sum of the analytic (instrument) variance ($s_a^2$) and the intra-patient biologic variance $(s_b^2):y_0^2=s_a^2+s_b^2$.

Transformation of Quality Control Results into Short Term Analytical Variation

In clinical laboratory testing, 2 or 3 levels of QC material are often assayed per 24 hours per analyte. FIG. 1 shows, for two Radiometer 800 blood gas analyzers, from Radiometer of Copenhagen, Denmark, an SDD calculated for 2-hour intervals (the analyzers' SDD values are represented by light and dark points, corresponding to respective analyzers). Both analyzers ran Level 1 QC product for ionized calcium. The number of differences that are incorporated into the SDD calculation are represented by the vertical bars, either light or dark, again representing the individual analyzer. Most of the time, the blood gas testing is separated by 24 hours (highest frequency bar at 24 hours). The SDD of the instrument represented by the dark points is approximately 0.005 mmol/L. The SDD of the other instrument (light points) is approximately 0.008 mmol/L. FIG. 1 illustrates SDD graphs for Level 1 Radiometer 800 QC data from 2 different instruments, represented by dark and light points, respectively.

Figure 2:
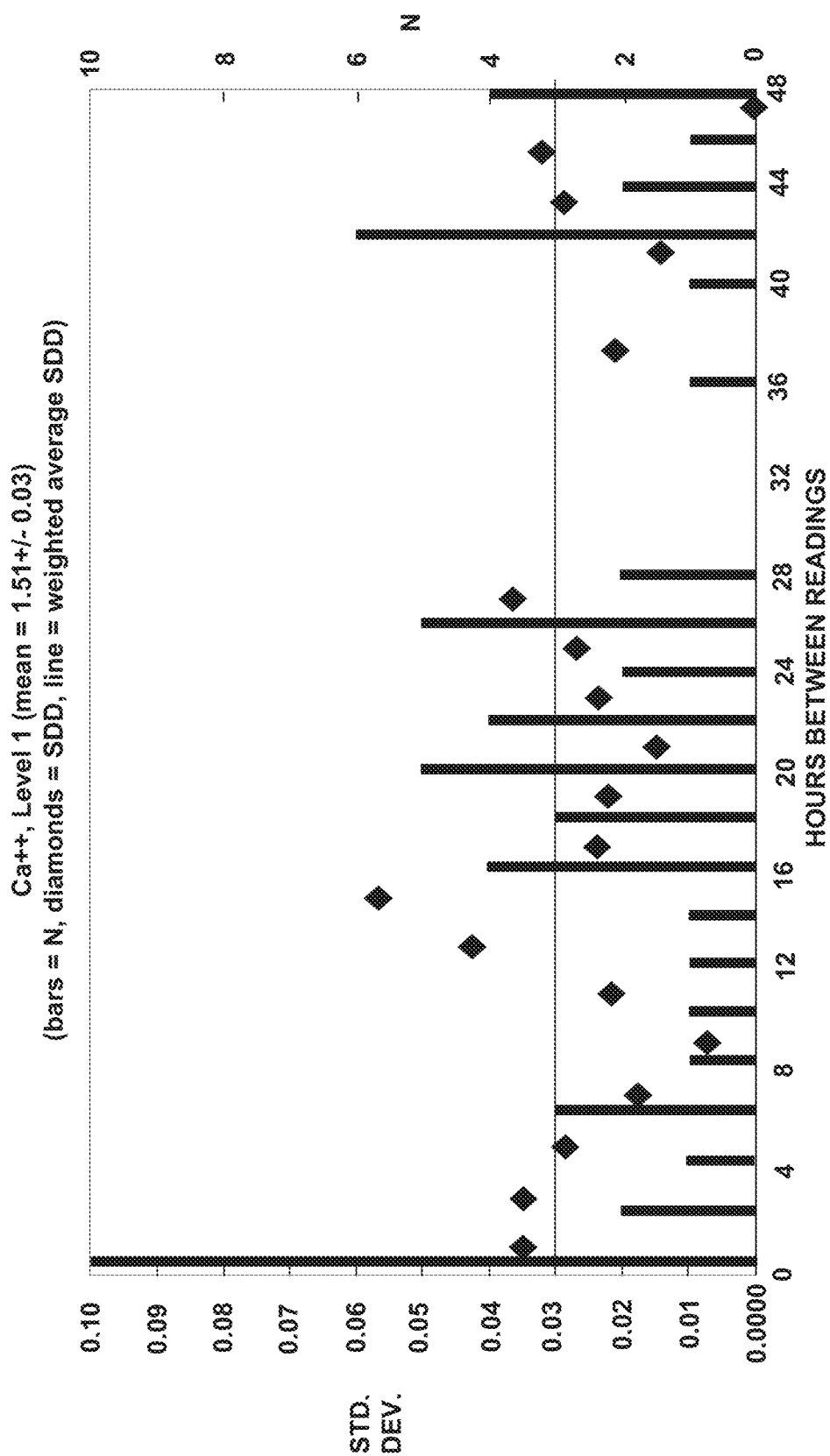
FIG. 2 illustrates, by way of example, an embodiment of an SDD graph for two GEM 5000 blood gas analyzers with the SDD calculated at 2 hour intervals for both analyzers.

FIG. 2 shows the SDD graph for two GEM 5000 blood gas analyzers with the SDD calculated at 2 hour intervals for both analyzers (the resultant SDD values are represented by dark points) analyzing the Level 1 quality control product for ionized calcium. After a control is analyzed, very little time elapses before another QC specimen is analyzed. This short time interval implies that the value of the newest control result may be so unexpected that there is another QC specimen run just to verify the previous value. The SDD intercept is much higher on the GEM analyzer compared to the Radiometer (in excess of 0.03 compared to 0.008 mmol/L). FIG. 2, SDD graph for a Level 1 GEM instrument, from Instrumentation Laboratory of Bedford, Mass., USA, represented by dark points.

Transformation of Consecutive Intr-Patient Results into Short Term Analytical Variation and Biologic Variation It has previously been shown for serial electrolytes and blood gases measured in an intensive care unit, that biologic variation of these analytes can be derived from graphical analysis of the standard deviation of differences (SDD) of the serial tests vs the time between the serial tests (Clin. Chem. Lab Med. 2010 October; 48(10):1447-54).

At very short time intervals between serial tests, the average variance of the test results represents the sum of the analytic variance ($s_a^2$) and the usual biologic variance ($s_b^2$) statistic, which can be obtained in the usual manner in which samples are regularly obtained from healthy individuals and then analyzed on highly precise instrumentation. $s_{t \to 0}=(s_a^2+s_b^2)^{1/2}$ As the time lengthens between the serial tests, more variation may be added to the total variation. If the variation is regressed against the time between sampling (or testing), the variation at the y intercept is $y_0=(s_a^2+s_b^2)^{1/2}$.

Thus, if the average intra-patient variation of thyroid stimulating hormone (TSH), for example, is plotted against time between consecutive TSH tests, the y-intercept ($y_0$) represents the sum of the short-term analytic variation and the biologic variation $y_0=(s_{aTSH}^2+s_{bTSH}^2)^{1/2}$.

The biologic variation can be calculated from: $s_{bTSH}=(y_0^2-s_{aTSH}^2)^{1/2}$.

Thus, within-patient variation (biologic variation) can be derived from patient data available in the laboratory information system (LIS) with no extra sampling or testing required. This average within-patient (sometimes called intra-patient) variation can be derived from the large numbers of patients being tested at relatively short time intervals with the time interval representing the time between successive sampling.

Figure 3:
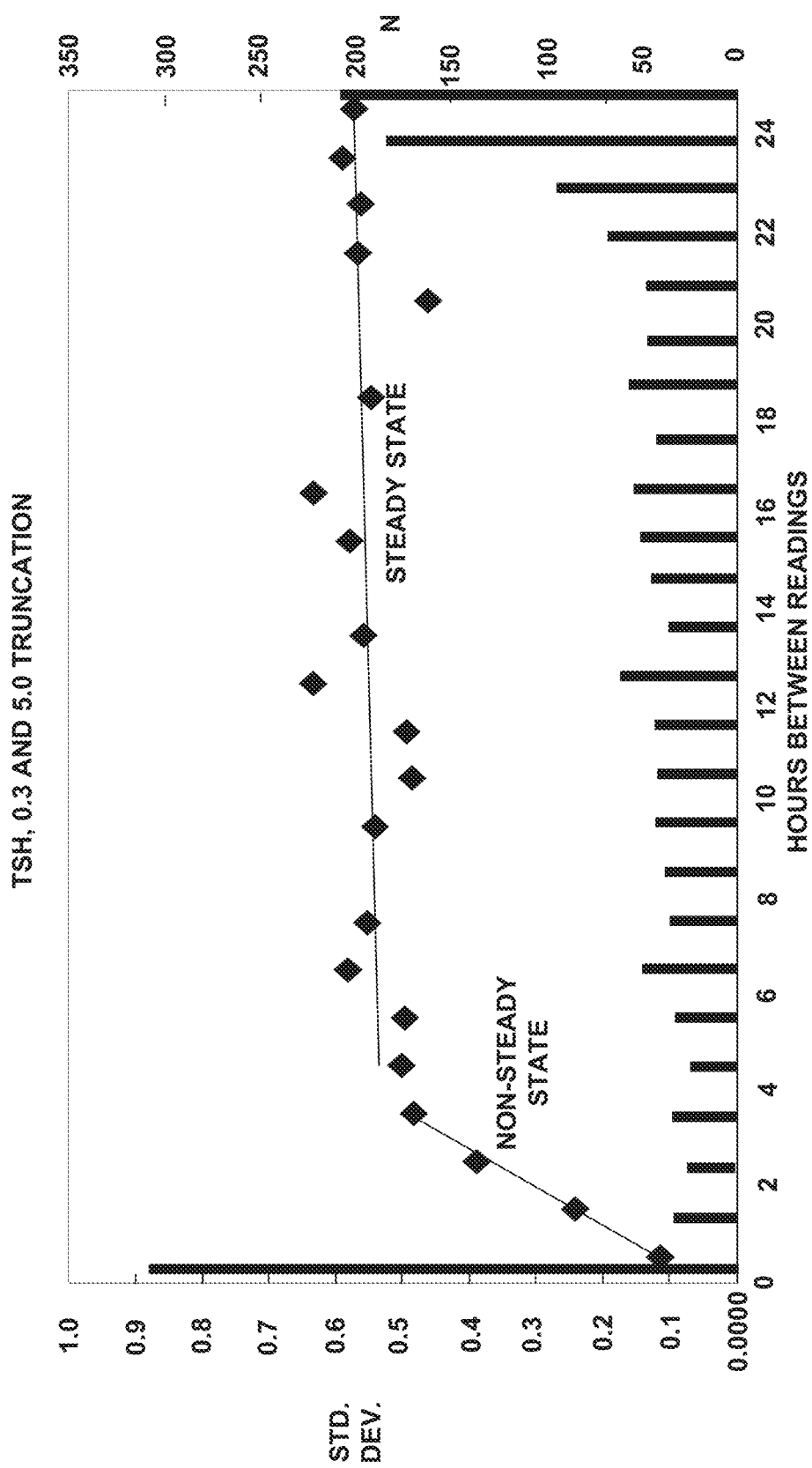
FIG. 3 illustrates, by way of example, an embodiment of an SDD graph for TSH.

In FIG. 3, the SDD approach was used to estimate biologic variation of TSH of primarily in-patients who have had their TSH repeated within 25 hours. Outlying TSH data (<0.3 or >5.0 mIU/L) was eliminated. A total of 1856 different patients had 4155 TSH ordered at least twice within 48 hours (median TSH=1.7, average TSH=1.98 mIU/L). FIG. 3 illustrates an SDD analysis of repeated TSH values; steady state regression analysis yields $y_0$ and sum of biologic and analytic variation.

FIG. 3 shows the SDD points for TSH for the first 25 hours (long regressed line). The standard deviation of the serial patient TSH pairs (the SDD [indicated by the diamond symbol]) are plotted against the time interval between the paired serial tests. The number of paired patient samples (N) is indicated by the vertical bar.

Two sets of linear regression lines have been inserted. The longer line, derived from the SDD from hour 5 to hour 25 represents TSH in a steady state (e.g., enough time has transpired for the hypothalamic-pituitary-thyroid axis to have adjusted). This longer line is the type of curve that may be expected in such numerical analyses. The y-intercept is about 0.52 mIU/L.

The shorter line, derived from about the first 4 hours of SDD points shows a non-steady state consisting of the early responses of the hypothalamic-pituitary-thyroid axis to various thyroid perturbations. Currently, TSH is the only analyte known by the inventors to have this early response. The y-intercept is about 0.064 mIU/L and is a measure of the average analytic standard deviation for a median TSH of 1.7 mIU/L. At this TSH median of 1.7 mIU/L, the QC derived $s_a$ is about 0.10.

For the steady-state TSH, the regression equation of the intra-patient SDD vs. time yields a y intercept of 0.52 mIU/L. Substitution of the QC derived $s_a$ results in a $s_b$ of $(0.52 \times 0.52 - 0.1 \times 0.1)^{1/2} = 0.51$ mIU/L. When expressed as a relative error, this $s_b$ is 30%, higher than the 19% estimate in Ricos' compilation of biologic variations, obtained in a traditional manner.

For the non-steady state TSH, it is probable that the y-intercept will primarily reflect the analytic error of the assay with little or no perturbations of TSH due to physiology and pathophysiology. The analytic imprecision would be 0.06 mIU/L at median TSH of 1.7.

A methodology was developed that transforms either sequential QC data or sequential intra-patient test results into measures of analytic and biologic variation from the patient data. This methodology has been used to study the imprecision of single and multiple analytical systems reporting either QC or patient blood gas, hematology, and glycohemoglobin results. This method does not require any additional laboratory testing. Rather, it involves procuring a series of either QC or patient data available in laboratory information systems. Then these consecutive QC test pairs or intra-patient result pairs into period bins that reflect the interval of time between consecutive tests. For each time interval, the SDD can be calculated for intra-patient test pairs within that interval, $(x_1, x_2), (x_3, x_4), \ldots, (x_{2i-1} x_{2i},) \ldots (x_{2n-1}, x_{2n})$:

$$SDD = \sqrt{\frac{\sum(x_{i-1}-x_i)^2}{2n}} \quad [1]$$

In the first few hours that a test is repeated, the SDD vs time line is generally linear and, if the SDD is regressed against the midpoints of the time intervals, the y-intercept $(y_0)^2$ represents the sum of the analytic variance ($s_a^2$) and the intra-patient biologic variance ($s_b^2$):

$$y_0^2 = s_a^2 + s_b^2 \quad [2]$$

For many analytes, especially those whose concentrations are closely controlled by the body's homeostatic mechanisms, $s_b$ is relatively constant. By rearranging equation [2], the biologic variation, expressed as a standard deviation can be derived from the y intercept of the SDD graph and the analytic variation $$s_b = (y_0^2 - s_a^2)^{1/2} \quad [3]$$

I. Transformation of Quality Control Results into Long Term Analytical Variation (Long Term Standard Deviation of Differences: LTSDD)

FIGS. 4-19 show how QC charts (graphs of QC values vs time) can be transformed with long-term SDD analysis to provide meaningful information to the laboratorian regarding the overall analytic acceptability of diagnostic assays based on months or years of testing QC materials. As a general rule, the lower is the biologic variation or the lower the analytic error, the easier it can be to study discriminate changes in the concentration of the measured analytes and associate the changes with a yet undiagnosed disease state, altered pathophysiology, or even improvement in patient status.

Figure 4:
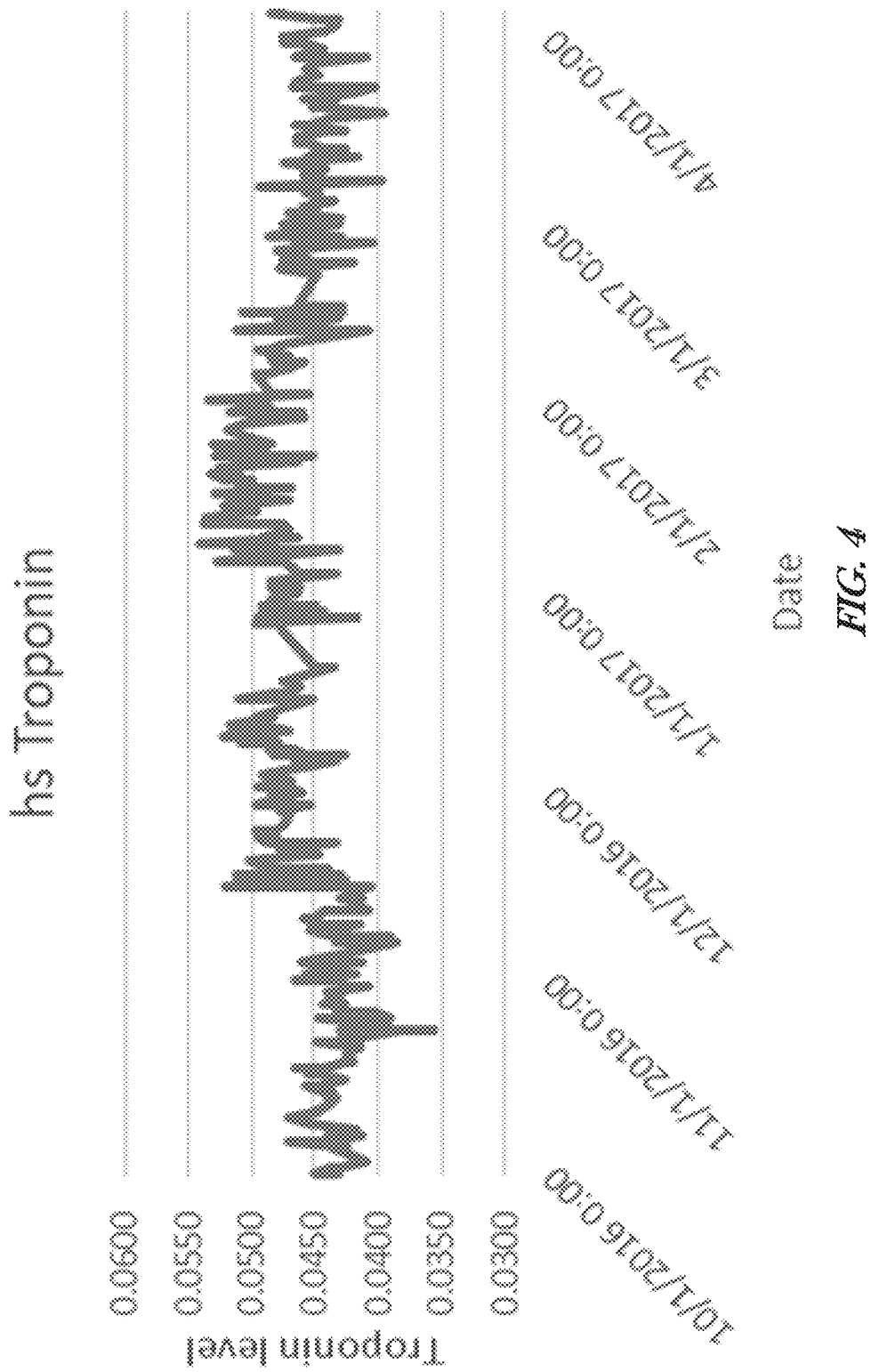
FIG. 4 illustrates, by way of example, a typical QC chart for a troponin test for diagnosing myocardial infarctions (heart attacks).

FIG. 4 shows a typical QC chart for a troponin test for diagnosing myocardial infarctions (heart attacks). Diagnostic companies are now designing troponin measurement methods to measure low levels of troponin in an accurate manner. Some manufacturers assert that if the total variation of the troponin measurement is less than 10% (maximum analytical error plus biologic variation), then the troponin test could be used to test healthy patients to get a baseline troponin value; then a year or more later, the troponin test might be repeated. If the variation exceeds the usual variation of the instrument plus the usual variation of the patient, then there might be a medical need to study the patient further, such as to discover any treatable causes of elevated troponin.

The manufacturers hope that the usual analytic error in troponin testing and the usual patient variation in troponin should interact to provide troponin levels that are apparently acceptable and not worthy of followup. Unusually increased analytic error does exist and can result in false diagnoses of elevated troponins, and may be due to a number of factors including reagent instability and degradation, calibration issues, instrument issues, or the like.

The manner that QC specimens are generally evaluated is overly simplistic and does not simulate what happens when a patient is sampled and tested at a certain time and then sampled and tested a few months or years later. There are more opportunities for the unusual analytic error to occur and cause an artifactual change in the monitored analyte or even disguise a real change in the monitored test.

What is needed, is an approach for interpreting the QC data to determine the long-term analytic variation. A previous patent covers a calculation of the SDD for measured pairs $(x_1, x_2), (x_2, x_3), (x_3, x_4), \ldots, (x_n, x_{n+1})$. The SDD analysis of these series of repeated control results permitted the calculation of short-term variation. If it is considered that a QC measurement represents a single patient measurement and measurements of the same analyte are available for 300 or more days, then any one of those other measurements may represent a repeat of the same patient.

Figure 5:
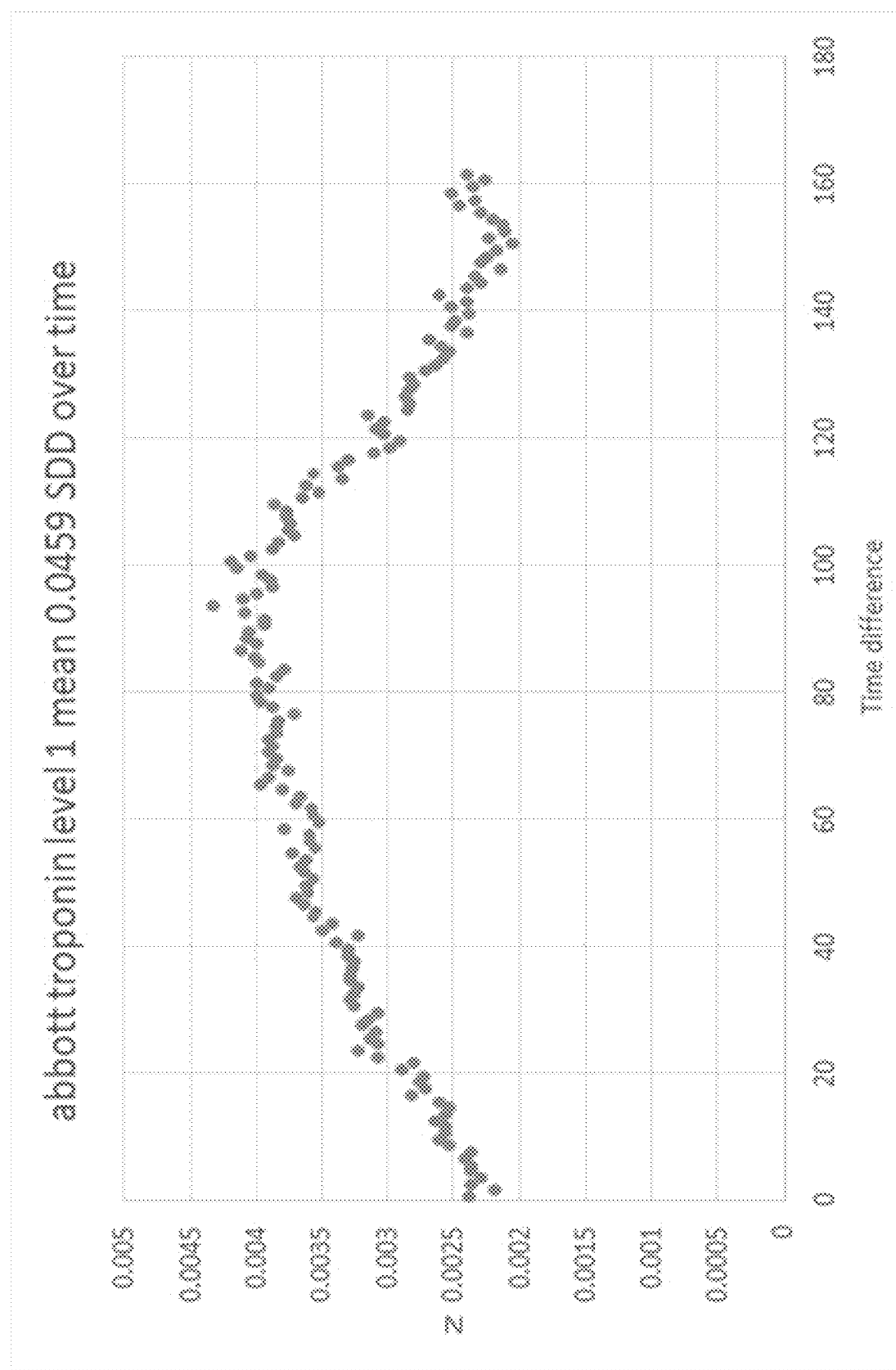
FIG. 5 illustrates, by way of example, an embodiment of an LTSDD view of QC chart showing unyielding climb of analytical variation for approximately 3 months.
Figure 6:
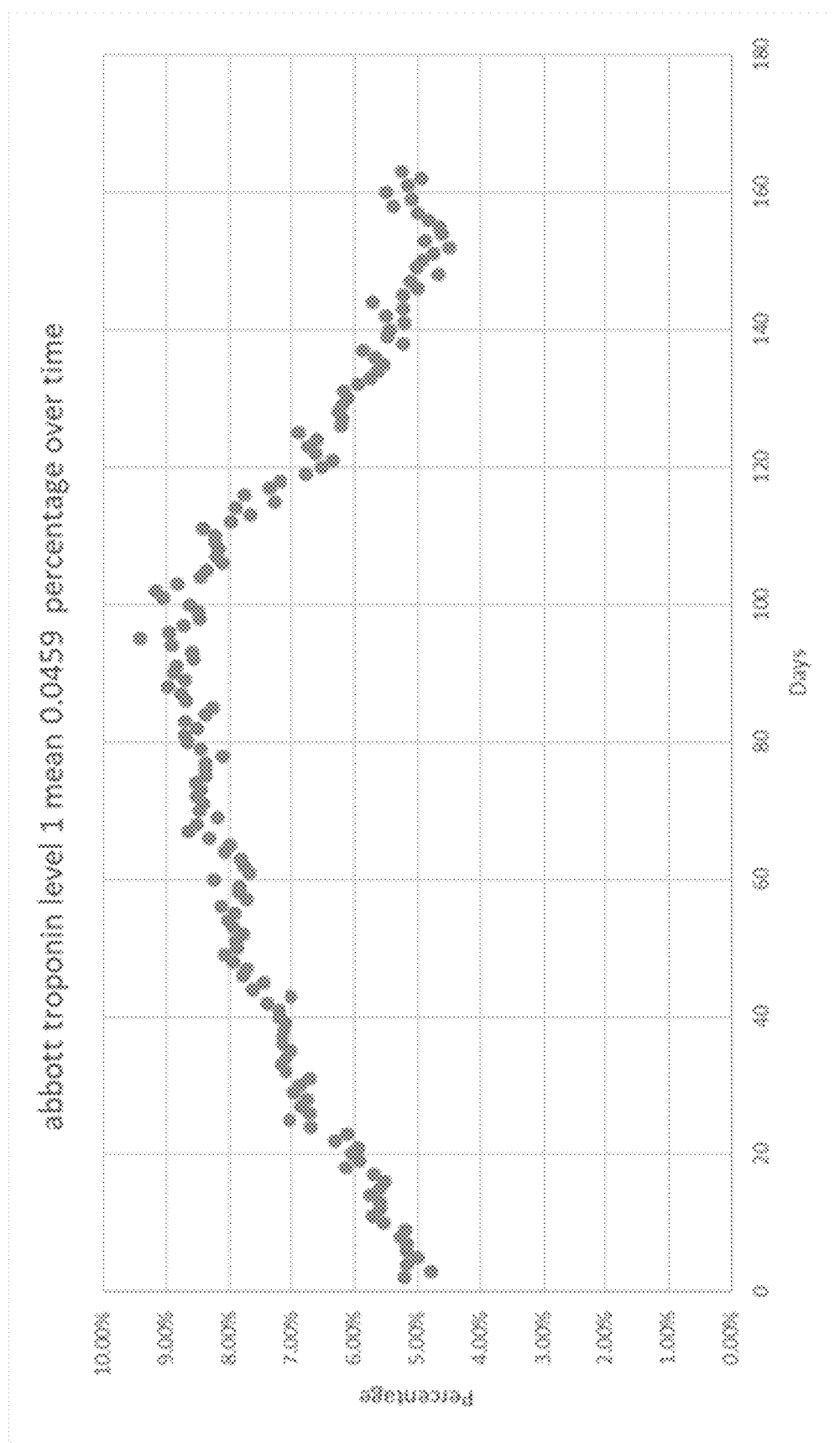
FIG. 6 illustrates, by way of example, an embodiment of an LTSDD view of a QC chart expressed as percentage showing unyielding climb of analytical variation for approximately 3 months (10% is often used to indicate maximum analytical variation in troponin).

All possible combinations of different time periods were considered and the measurements at the first and last times and were used in an SDD analysis, such as to produce an overall variation that can be experienced by a patient, regardless of when they are sampled and analyzed. FIG. 5 shows the magnitude of the average variation from the first to the last day of testing. At about 100 days, the potential patient variation becomes the highest and then decreases thereafter. FIG. 5 shows an LTSDD view of QC chart showing unyielding climb of analytical variation for approximately 3 months. FIG. 6 shows an LTSDD view of a QC chart expressed as percentage showing unyielding climb of analytical variation for approximately 3 months (10% is often used to indicate maximum analytical variation in troponin).

This is important, because a patient whose time between tests is near 100 days will be more likely to have further tests and analysis into their heart conditions based on these measured troponin levels.

Figure 7:
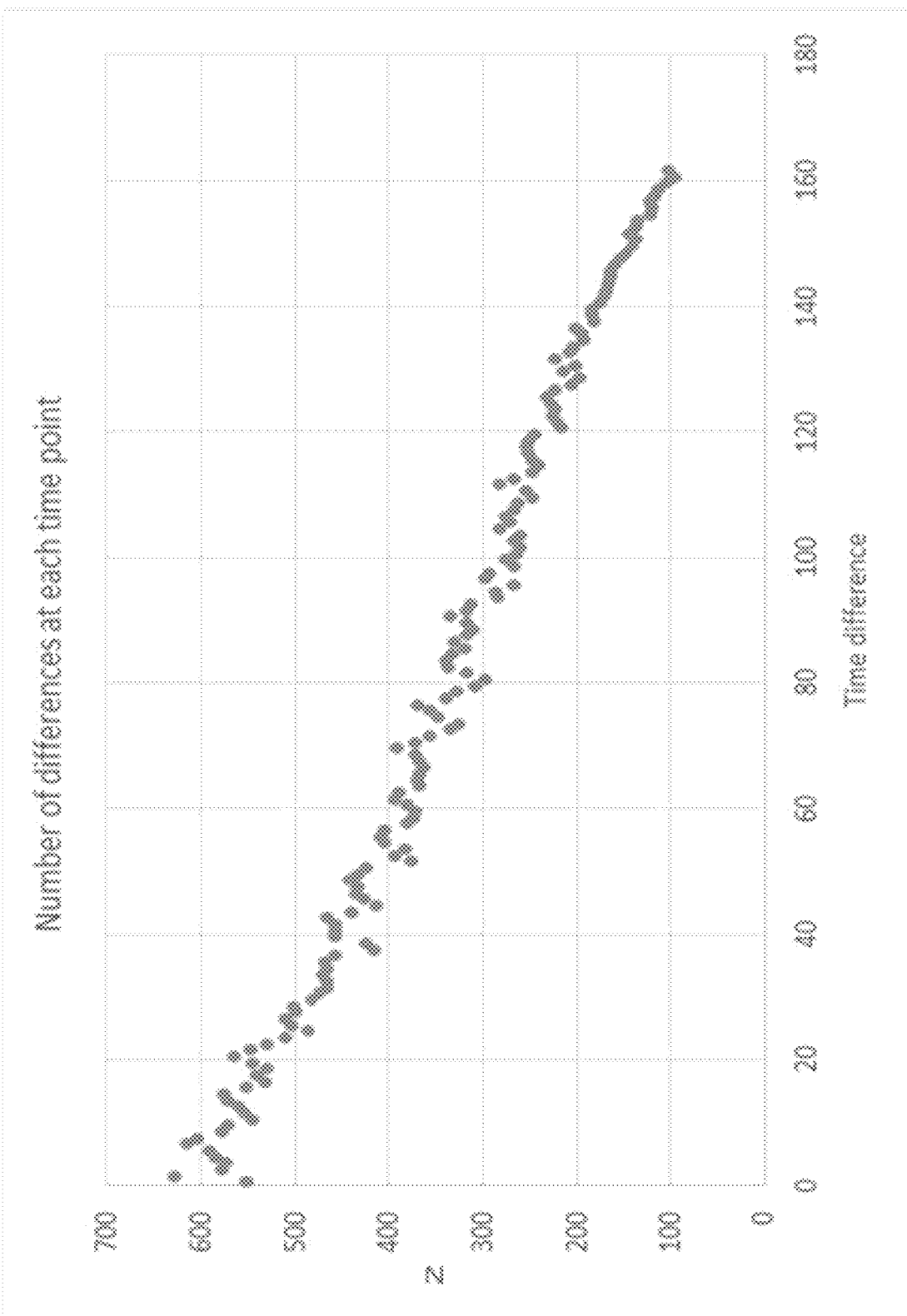
FIG. 7 illustrates, by way of example, an embodiment of the number of first and second result pairs that are analyzed with the SDD analysis to obtain the average variation.
Figure 8:
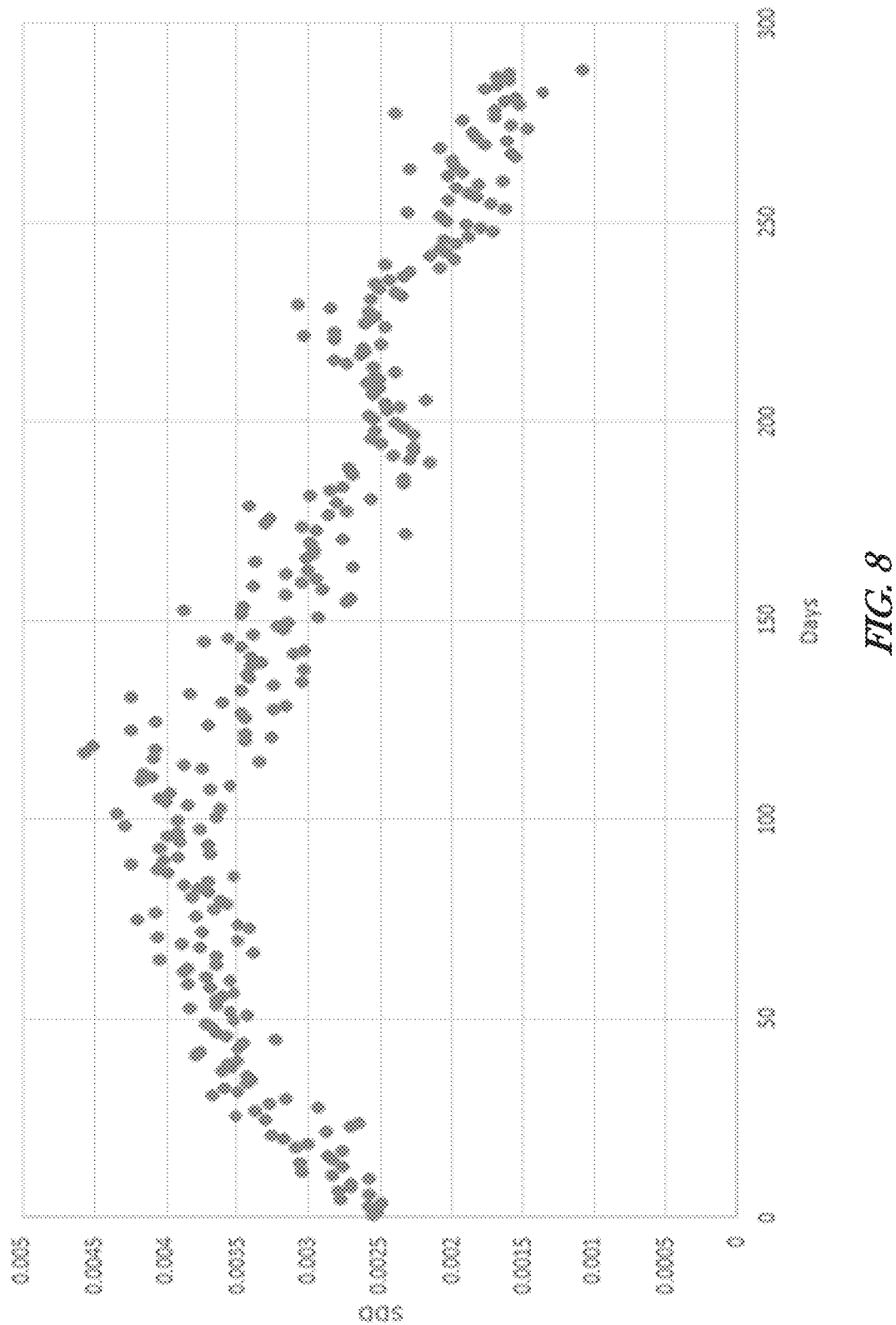
FIGS. 8-11 illustrate, by way of example, an embodiment of an LTSDD transformations of QC charts for hemoglobin A1c analyte measurements performed by a Beckman Coulter assay system, from Beckman Coulter of Brea, Calif.

FIG. 7 shows the number of first and second result pairs that are analyzed with the SDD analysis to obtain the average variation. FIG. 6 shows that the maximum analytic variation is around 9%. The sum of this variation and any patient variation can be close to the 10% recommended by industry as an indicator of significant change in the patient troponin. As virtually all of this change is analytical and not associated with the patient, it is evident that this troponin assay does not have adequate accuracy to be used for screening. FIG. 7 shows a number of pairs of first and next troponin pairs assessed in LTSDD calculations. The first few short time differences (intervals) encompass the maximum number of pairs. There were only around 100 troponin pairs that were separated by 160 days. This LTSDD analysis shows that this troponin assay of 10% needing further analysis is flawed. Medical personnel should consider the time between consecutive troponin measurements and adjust the troponin measurement levels by the time between such measurements. Then, the medical personnel can, after the adjustment, determine whether the troponin measurement indicates an abnormal condition that warrants further analysis. This adjustment will save many medical personnel hours, laboratory technician hours, or other hospital resources in attending to false-positive troponin tests.

FIGS. 8-11 show LTSDD transformations of QC charts for hemoglobin A1c analyte measurements performed by a Beckman Coulter assay system, from Beckman Coulter of Brea, Calif., USA. FIGS. 12-15 show LTSDD transformations of QC charts for hemoglobin A1c analyte measurements performed by a Capillarys system from Sebia of Norcross, Ga., USA. FIGS. 16-19 show LTSDD transformations of QC charts for hemoglobin A1c analyte measurements performed by a Roche Diagnostics assay system, from Roche Holding AG of Basel, Switzerland.

Figure 9:
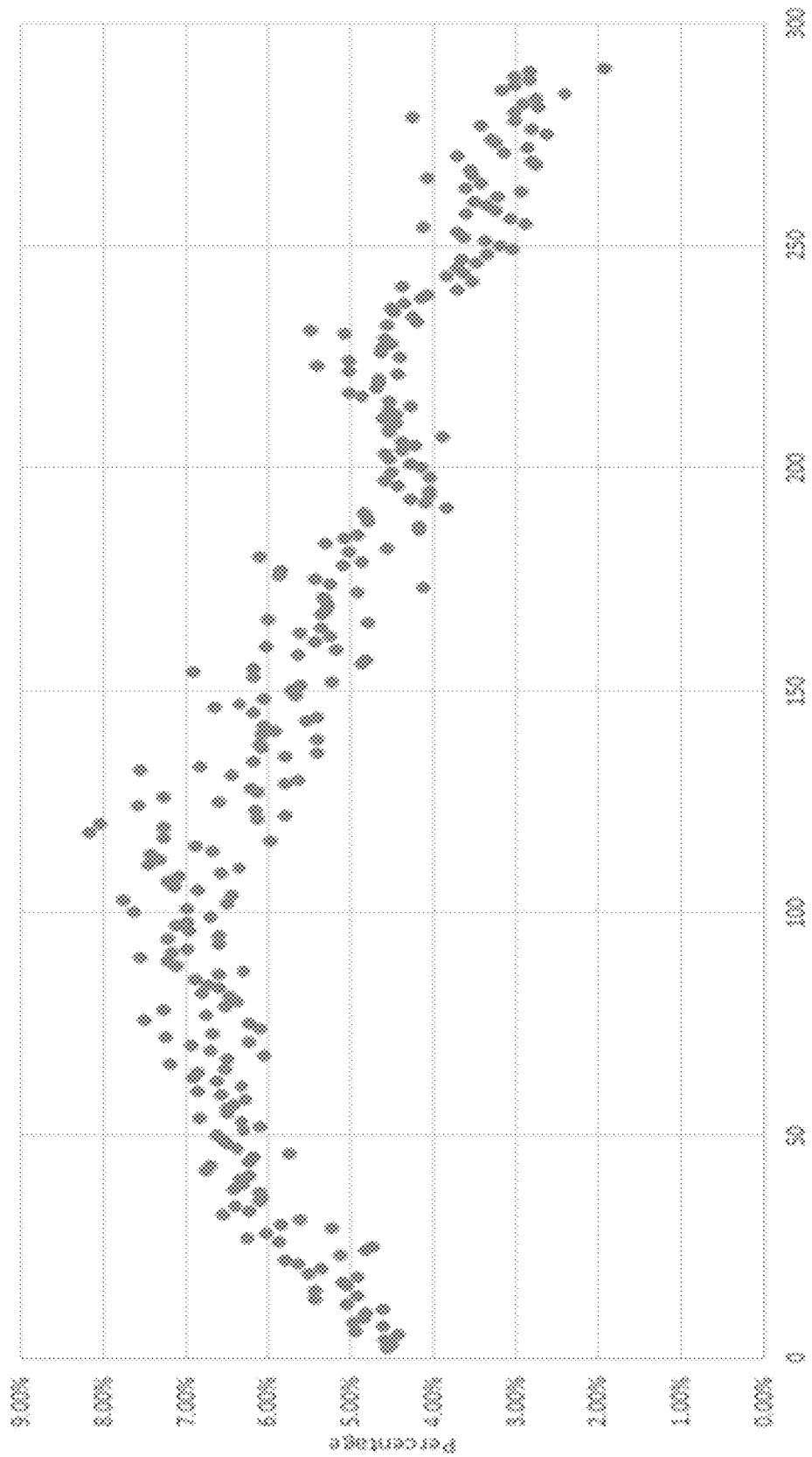
Figure 10:
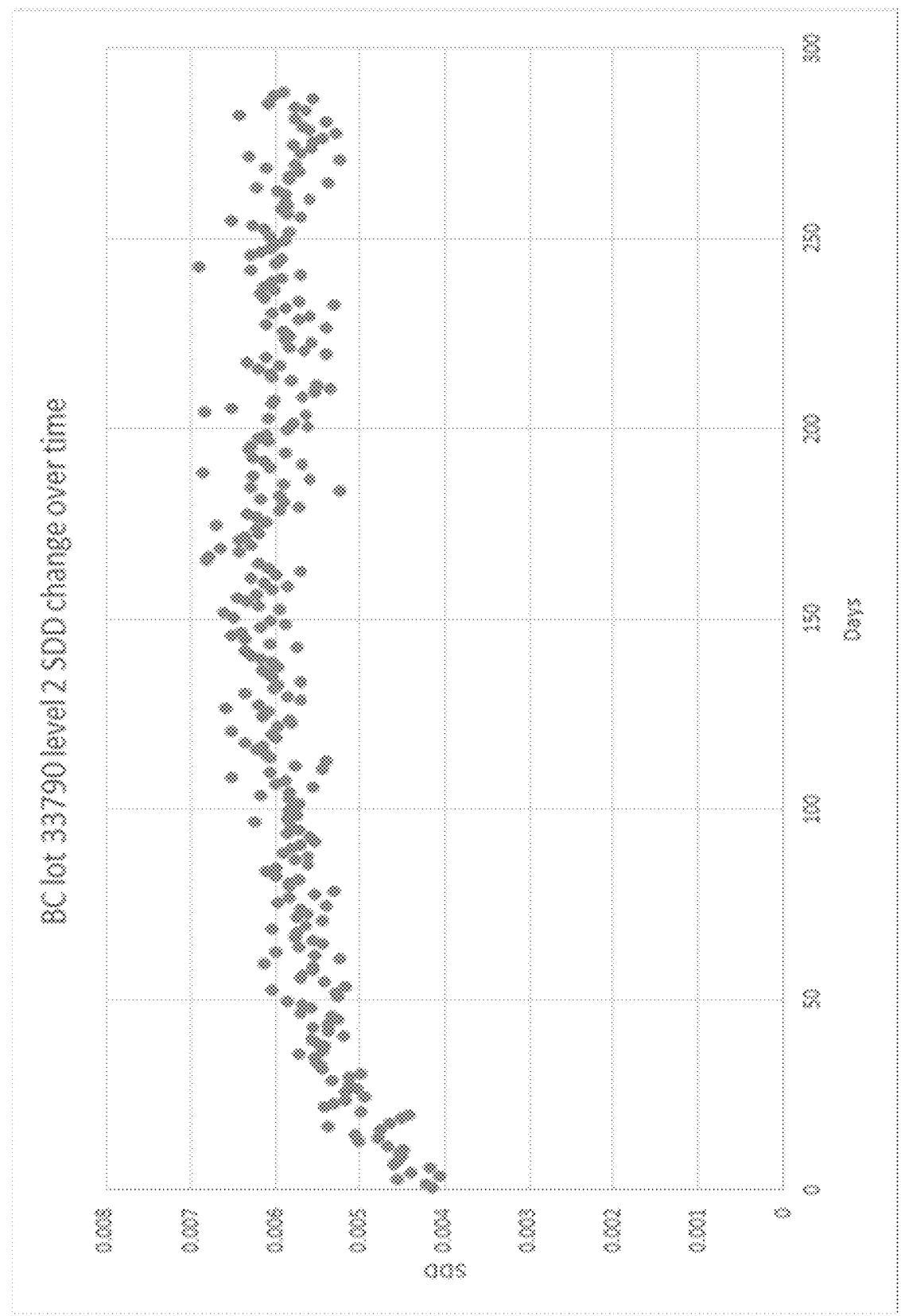
Figure 11:
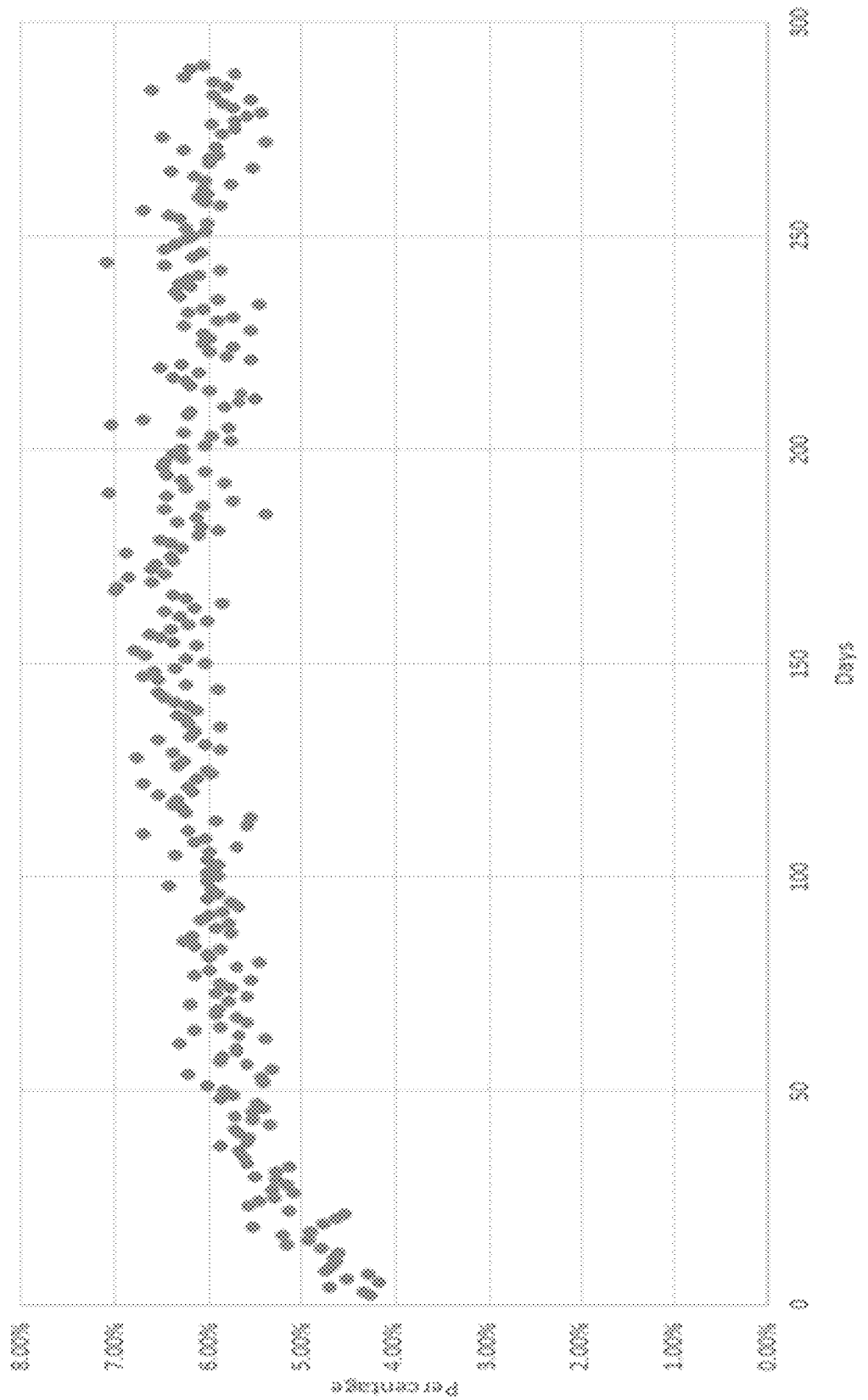
Figure 12:
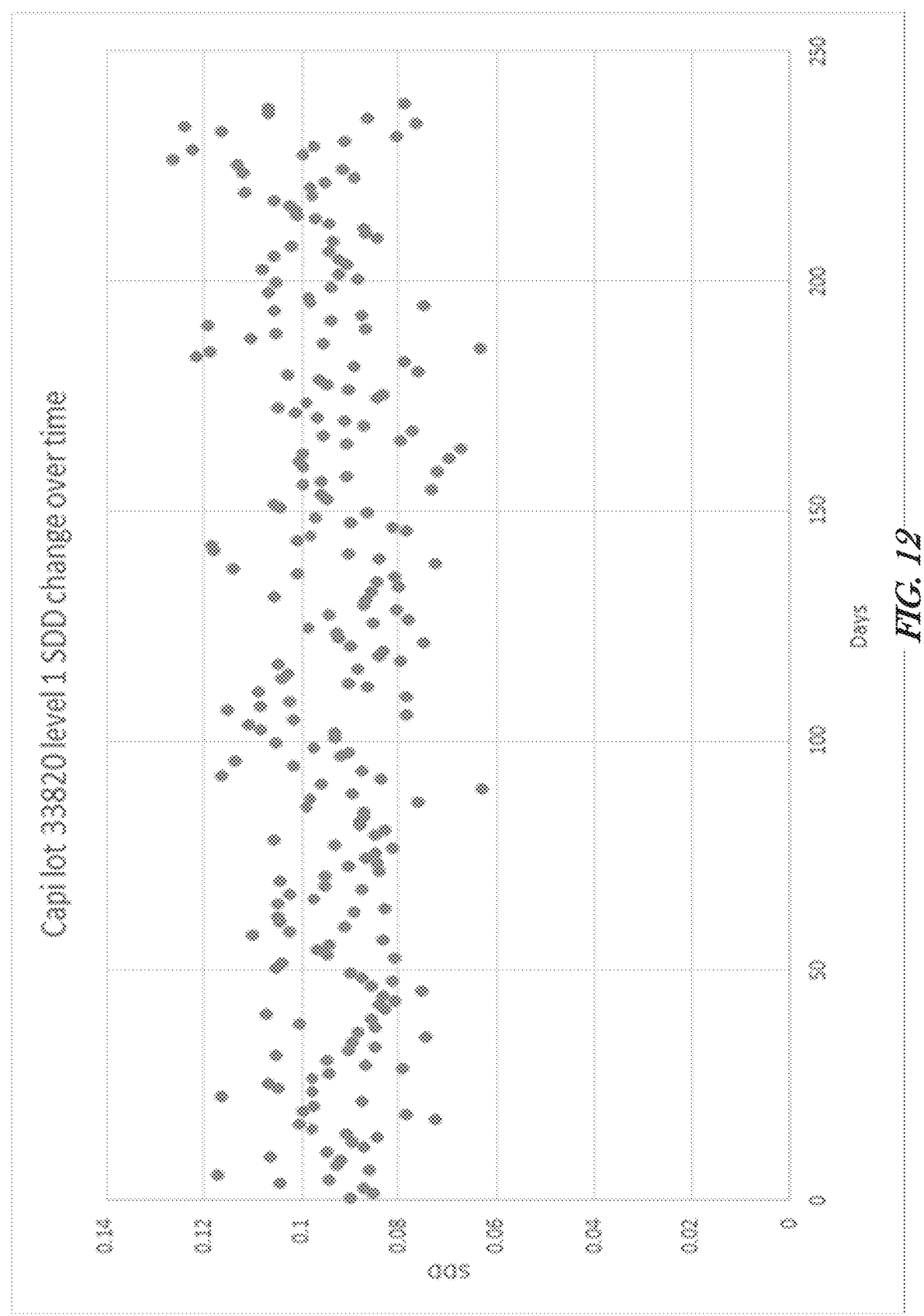
FIGS. 12-15 illustrate, by way of example, embodiments of LTSDD transformations of QC charts for hemoglobin A1c analyte measurements performed by a Capillarys system from Sebia of Norcross, Ga., USA.
Figure 13:
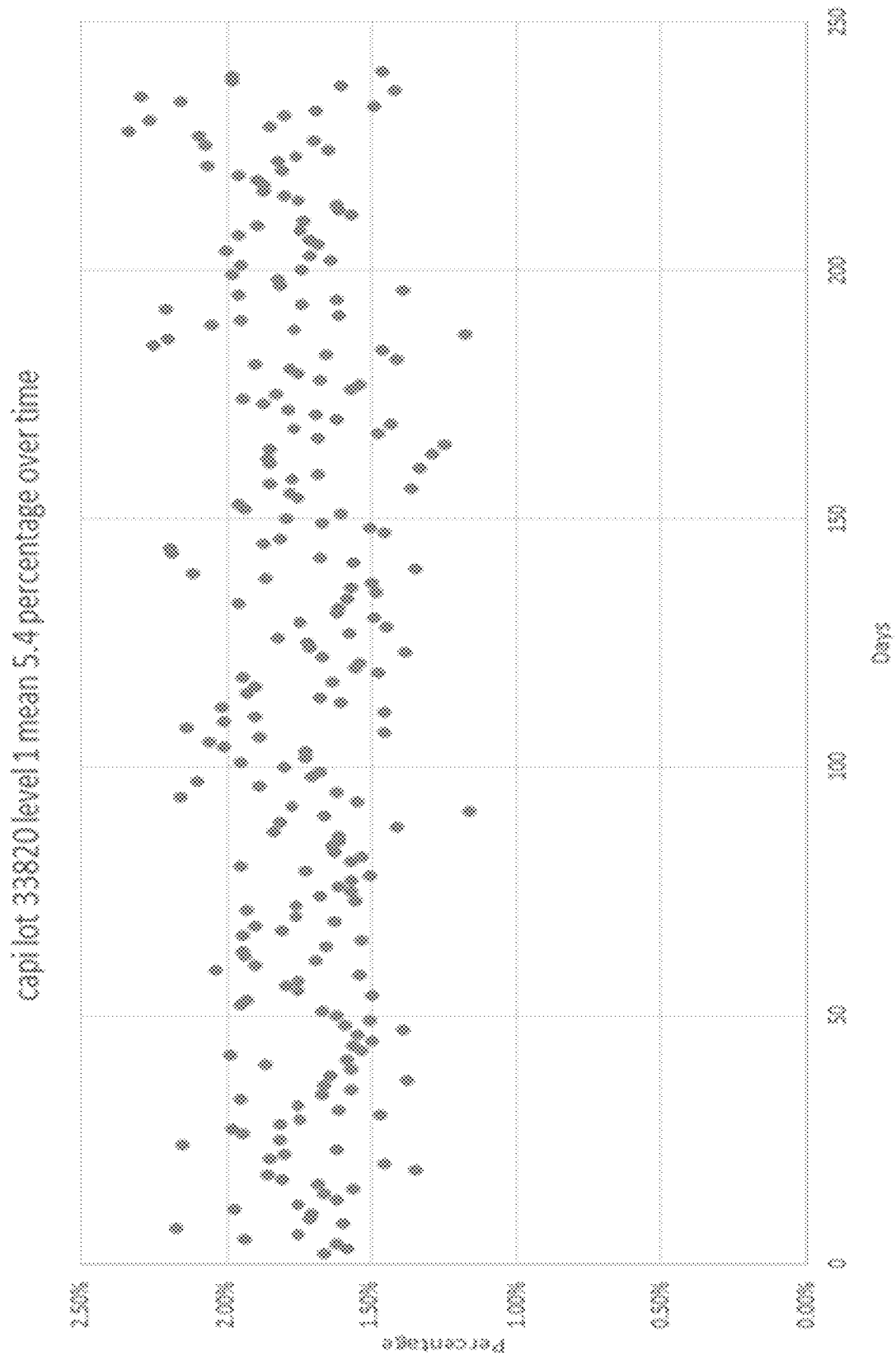
Figure 14:
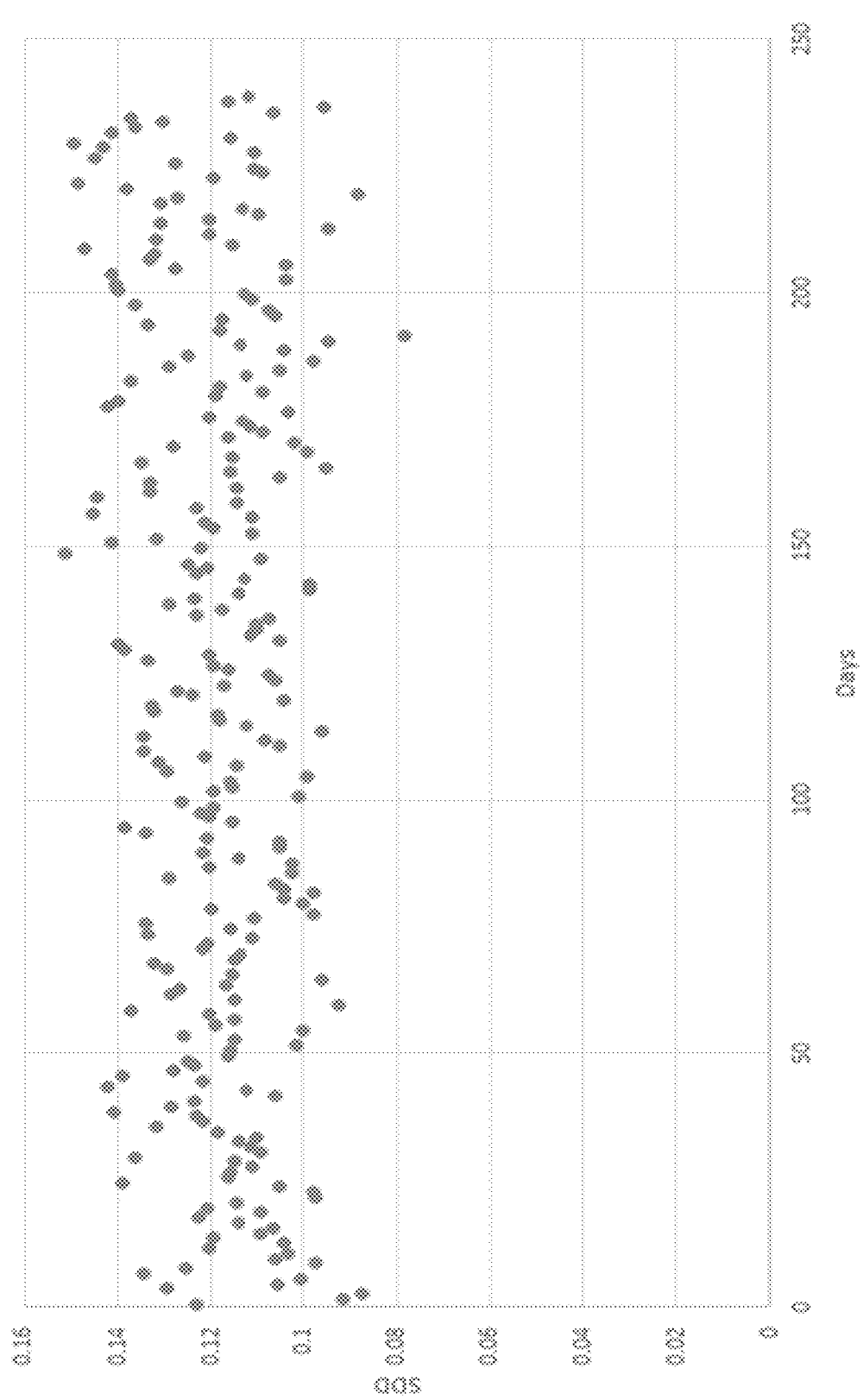
Figure 15:
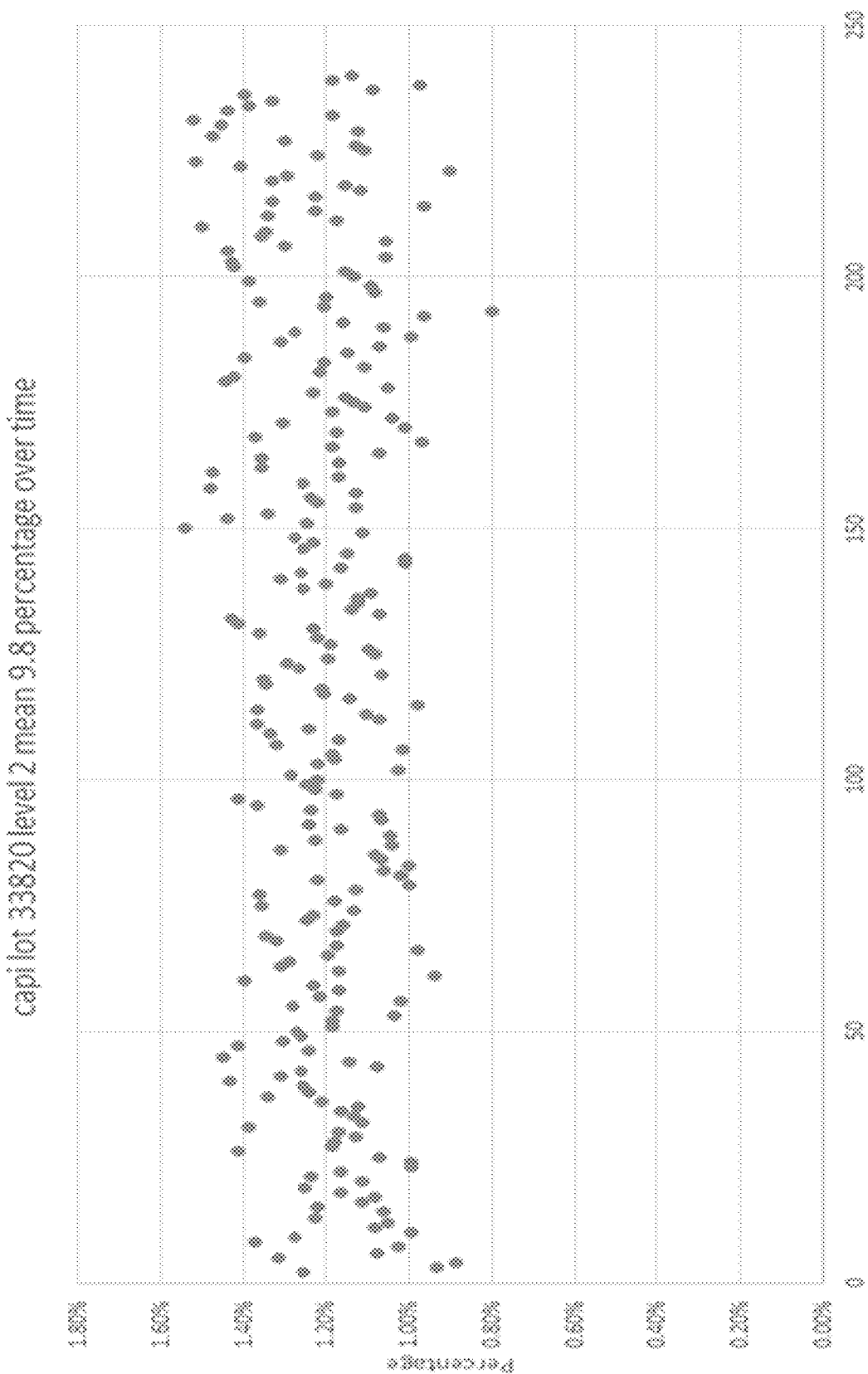
Figure 16:
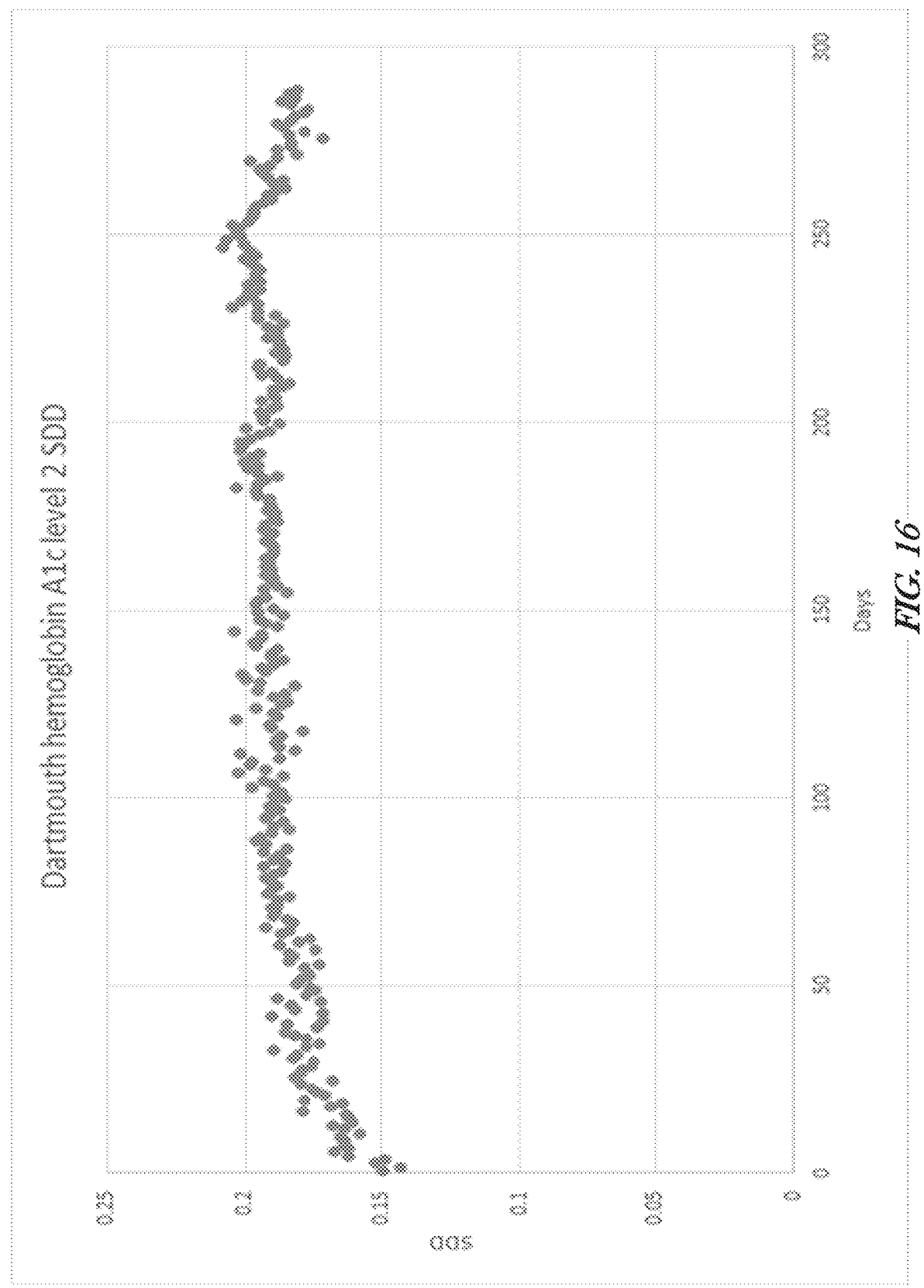
FIGS. 16-19 illustrate, by way of example, embodiments of LTSDD transformations of QC charts for hemoglobin A1c analyte measurements performed by a Roche Diagnostics assay system, from Roche Holding AG of Basel, Switzerland.
Figure 17:
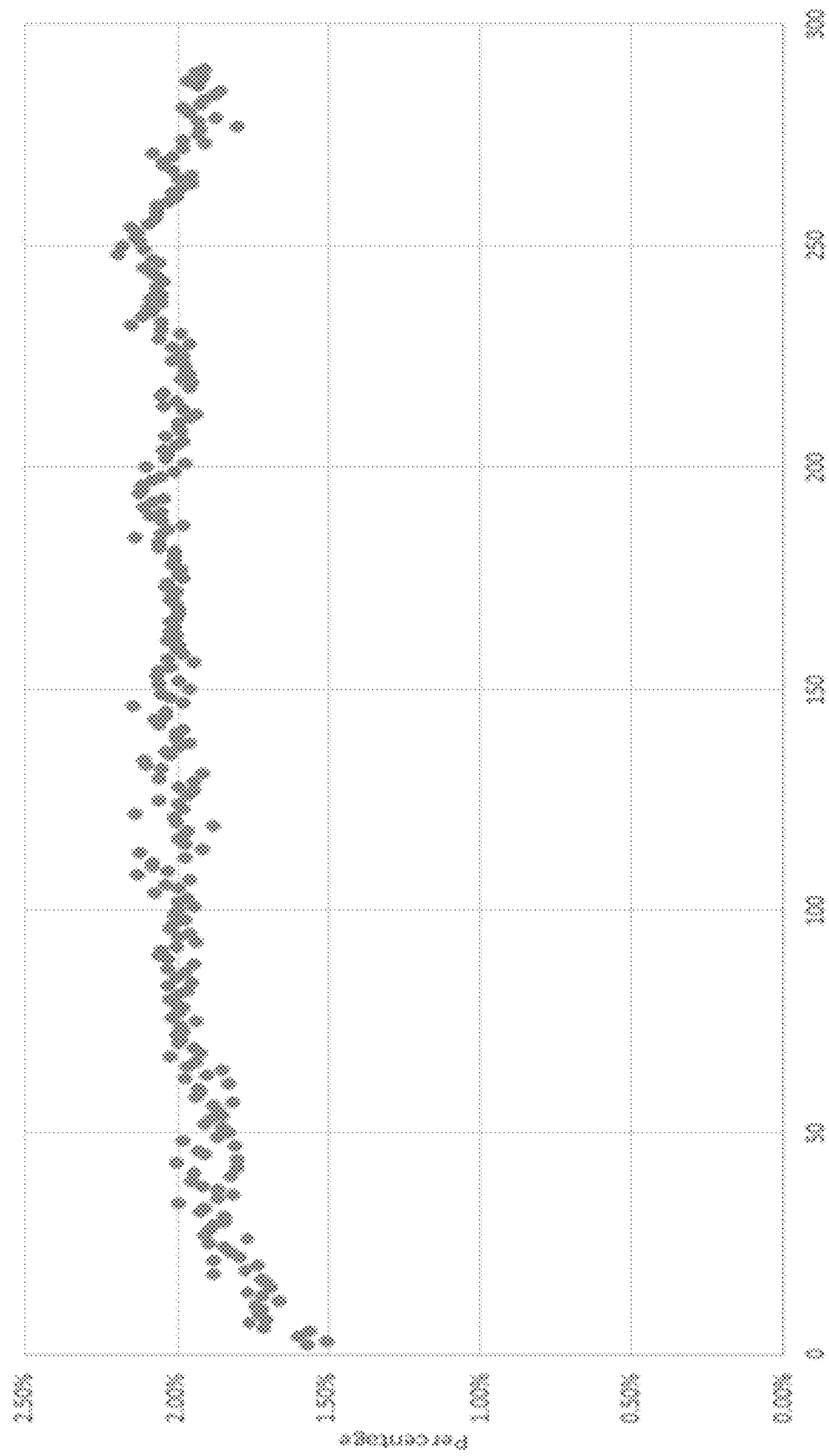
Figure 18:
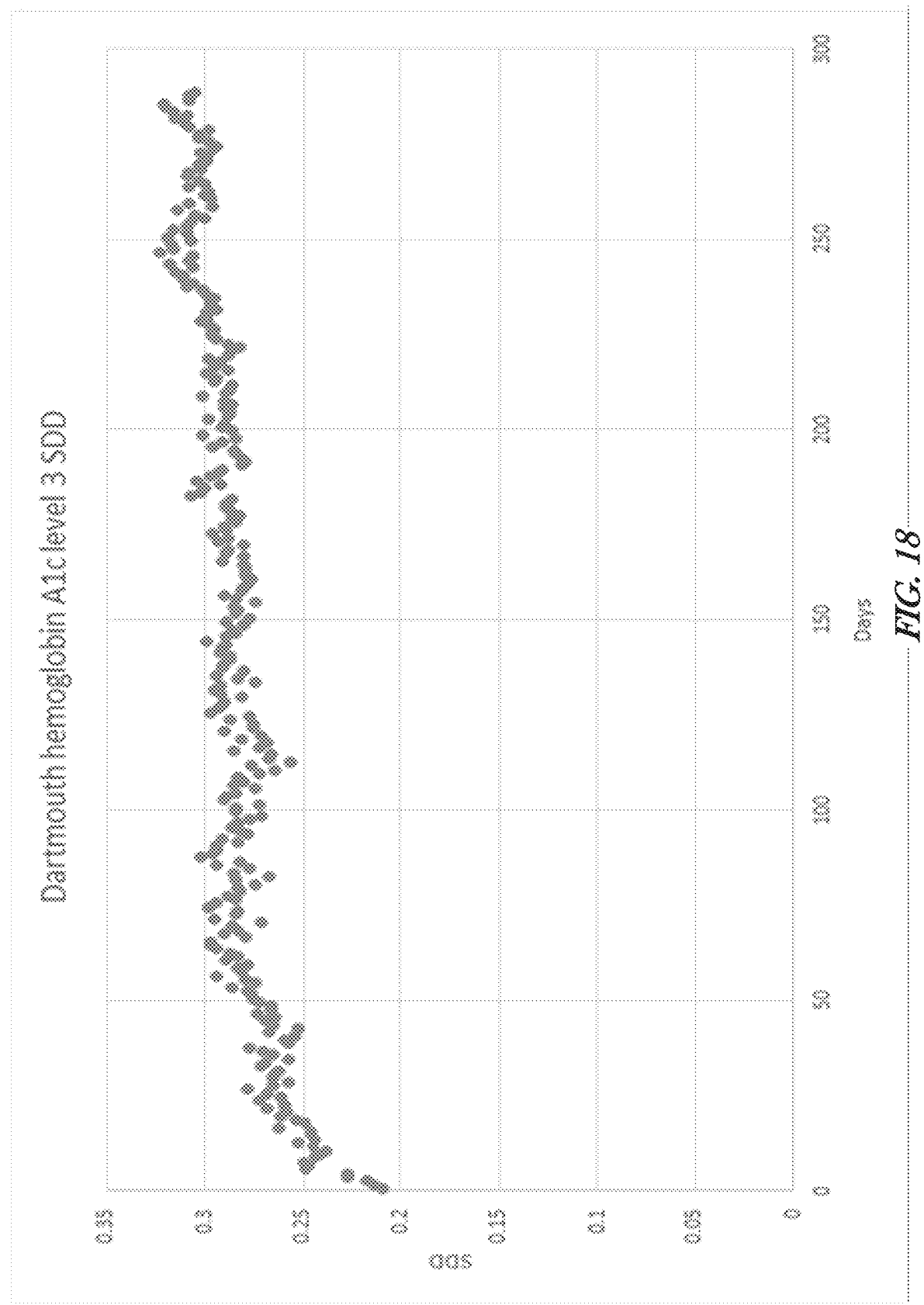
Figure 19:
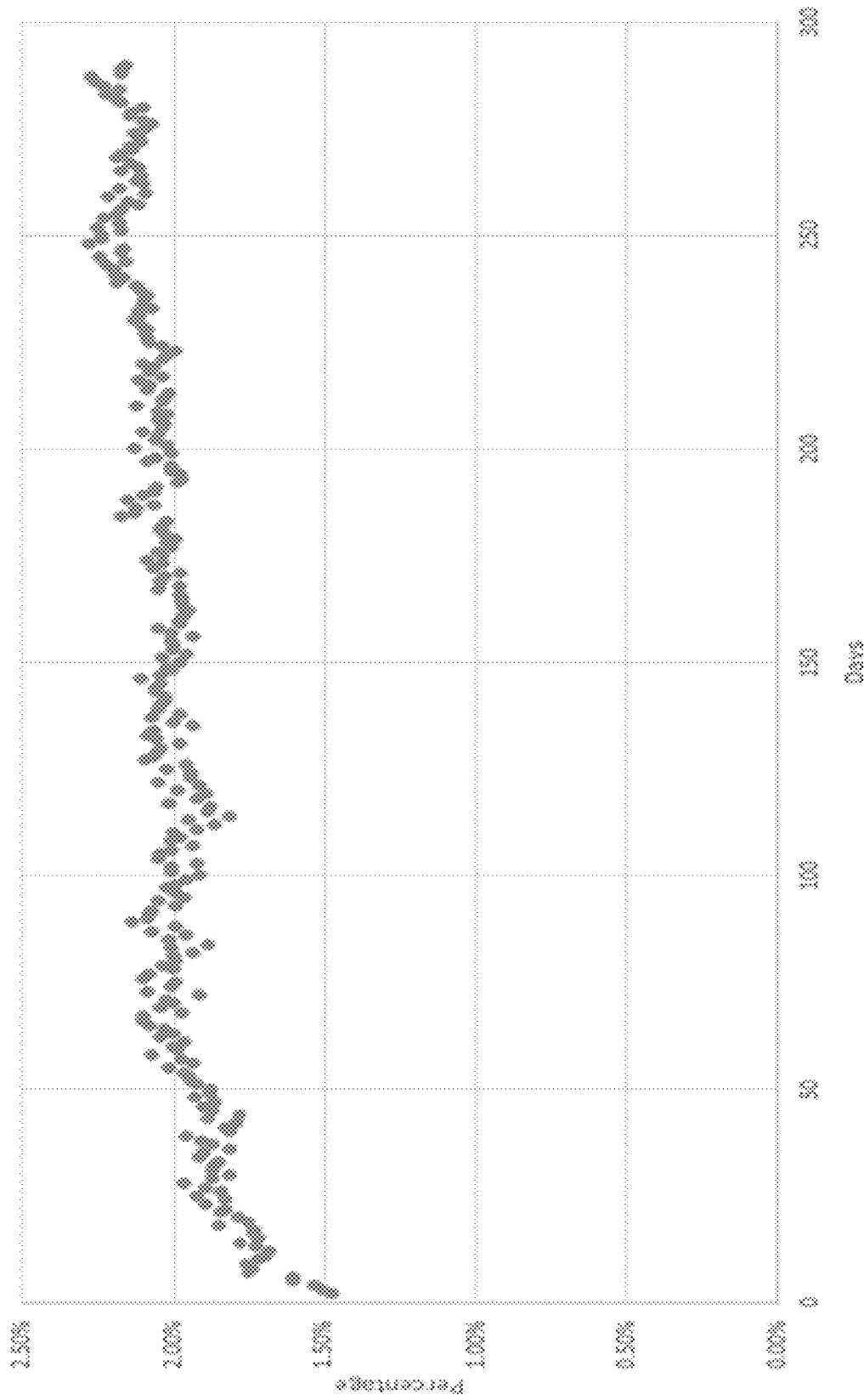

Hemoglobin A1c is used as a diagnostic marker for diabetes and can be related to patient's 3-month average blood sugar. The QC charts are not presented. An expansion of the Beckman LTSDD percentage variation from 4% to 7% to 8% over the time that the QC product is run is seen in FIG. 9. FIG. 11 shows the percentage van ation for the level 2 measurements have just a slightly lower variation. Various recommendations have been made regarding an optimal percentage variation of the hemoglobin A1c test. An example target of 2% is common provided for the long-term monitoring of patients with diabetes. If the user of the Beckman hemoglobin Mc assay realized that the assay would deliver results that varied by more than 7%, they would likely find a more stable method for measuring hemoglobin A1c. Such alternate methods would include those of the Capillarys and Roche systems whose transformed LTSDD graphs are shown in FIGS. 12-15 and FIGS. 16-19, respectively.

FIGS. 4-19 illustrate that some current assays are not suitable for the medical diagnostics that they are being used for. One use of long-term QC data measurements is to determine the efficacy of an assay. To determine the efficacy of an assay, historical QC laboratory analyzer data can be analyzed or additional QC laboratory analyzer measurements may be performed. A QC measurement is of a QC sample, rather than a measurement of a patient's analyte. The same QC sample can be measured repeatedly, at different times. The LTSDD values of the measurement can be plotted as a function of time (e.g., days) between measurements. Since all the measurements are on the same QC sample, all of the variation is attributed to analytic variation. If the analytic cariation is within a specified percentage (e.g., 15%, 20%, 25%, 33%, or 50%, or some percentage therebetween) of a target percentage, the assay is not sufficient and should be changed.

The target percentage can be different for different analytes. For example, for hemoglobin A1c, if using the Backman device assay, the target percentage can be about 5% more than a target percentage for using the Capillarys or Roche device assays. For Capillarys or Roche, the percentage can be about 2%. The specified percentage can be determined based on the costs of a false positive vs the risks of a false negative. If a false negative would be really detrimental to a patient's health, the specified percentage can be greater. If a false positive is too cost intensive to justify the risk, the specified percentage can be smaller.

The next section covers using an LTSDD analysis of intra-patient laboratory repeats to obtain meaningful measures of patient variation. Again, it is emphasized, the lower the biologic variation or the lower the analytic error, the easier it can be to study and discriminate changes in the concentration of the measured analytes and associate the changes with a yet undiagnosed disease state, altered pathophysiology, or even improvement in patient status.

Figure 20:
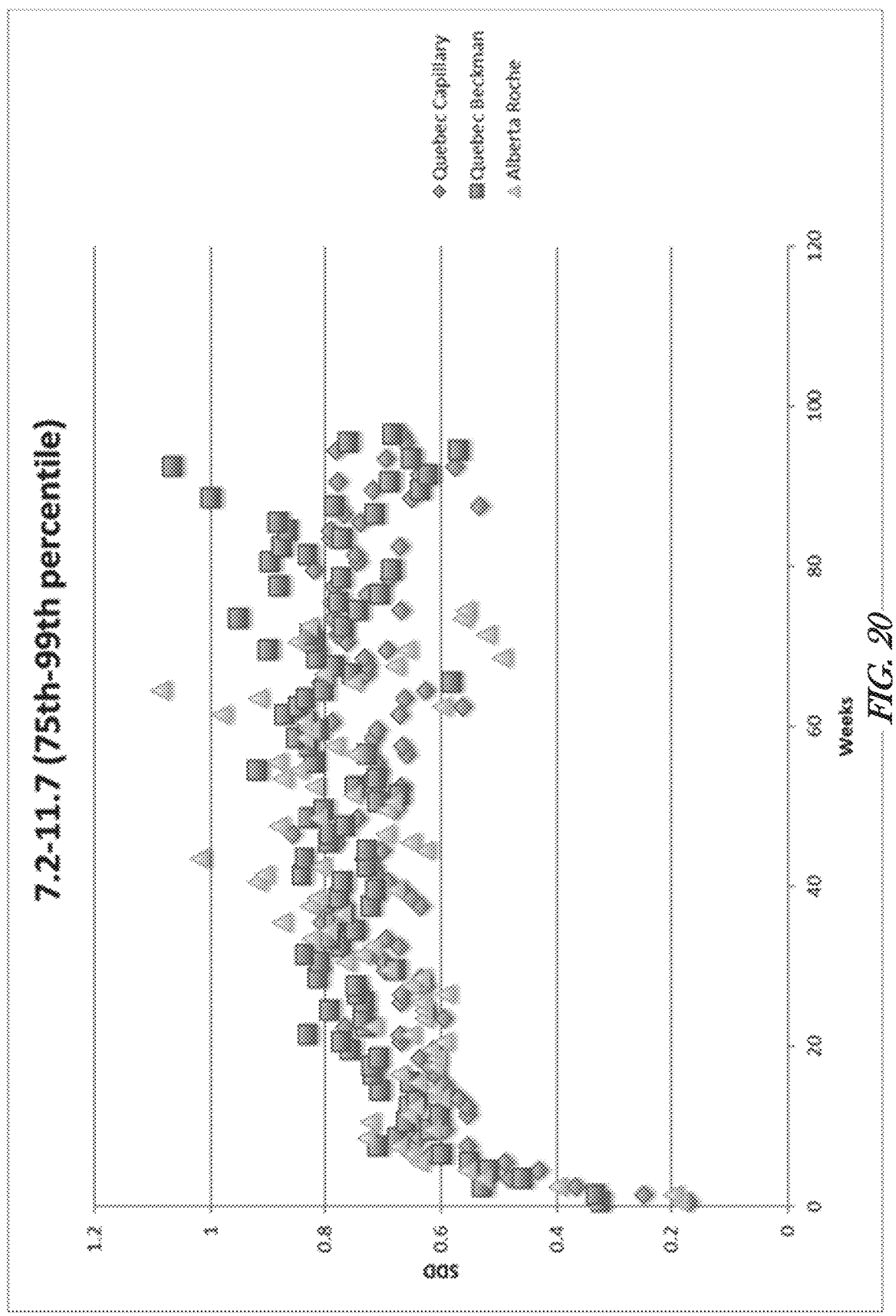
FIG. 20 illustrates the LTSDD of 3 different hemoglobin A1c assays in patients with poor diabetes control. There is a general overlap in the methods.

II. Transformation of Consecutive Intra-Patient Results into Density Diagrams of Analytical Variation and Biologic Variation Illustration 1: Hemoglobin A1c Hemoglobin A1c (HbMc) is a primary study analyte. A series of patient HbA1c measurements were assembled from 2 different laboratories and several different analytic methods, the Beckman immunoassay method, the Capillary's electrophoresis method, and the Roche immunoassay. The patient SDD graphs for these 3 different tests are shown in FIG. 20. FIG. 20 illustrates the LTSDD of 3 different hemoglobin A1c assays in patients with poor diabetes control. There is a general overlap in the methods.

The LTSDD graphs are different from those presented in earlier research; intervals and between interval differences are calculated and transformed into the SDD calculations. This maximization of data points enables extension of the SDD line over much longer periods of time. In FIG. 20, the top 75 to the 99 percent of the patient HbA1c are used in the calculations (the range of the HbA1c is 7.2 to 11.7%).

A regression line may be interpolated through these data. The line may include a fitted polynomial which is linear, or near linear, in the first 4 or 6 weeks and then transforms into a curved, more gradually increasing line. The regression intercepts at time 0 are a mixture of biologic and analytic variation. For HbA1c, the biologic variation is relatively small compared to the analytical variation, such that the intercepts are virtually equivalent to the analytical imprecisions of the corresponding assays.

Figure 21:
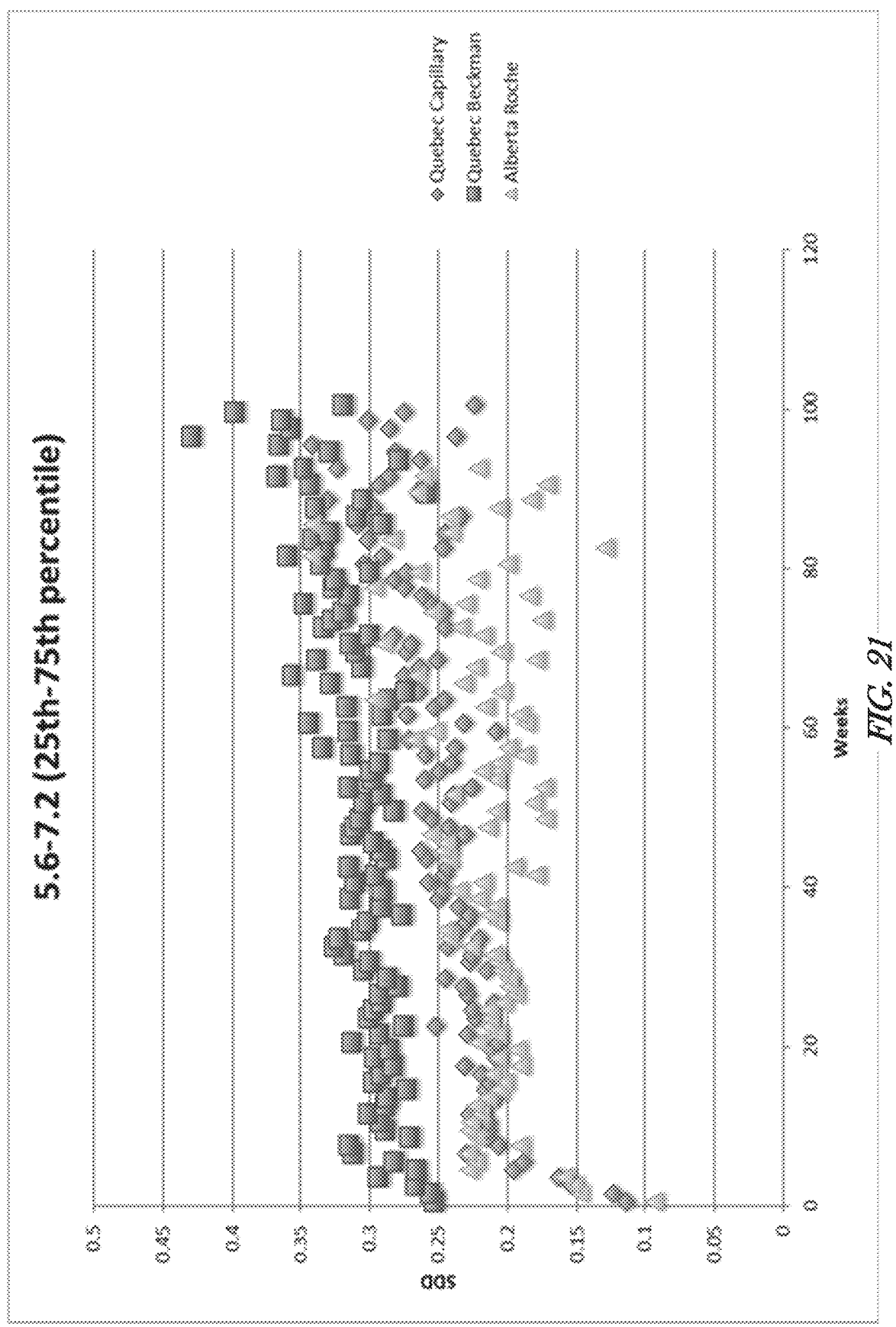
In FIG. 21, patients were selected whom had HbA1c values between the 25 to 75 percentile (from 5.6 to 7.2%), the maximum SDD was less than 0.4%.

The biologic variation of the patient depends on his/her HbA1c Patients with very low HbA1c (presumably patients without diabetes) will have the lowest variation in HbA1c and patients with poorly controlled diabetes will tend to exhibit the highest HbA1c variation. In FIG. 21, patients were selected whom had HbA1c values between the 25 to 75 percentile (from 5.6 to 7.2%), the maximum SDD was less than 0.4%. While there is overlap between the Capillarys and the Roche, the patients run on the Beckman system have highly divergent LTSDD and probably exhibit too much variation to perform a medical diagnostic based on the Beckman data. The variation is associated with the Beckman system's increased analytic variability and hides the patient's biologic variability. FIG. 21 shows the LTSDD of the same 3 hemoglobin A1c assays in patients with good diabetes control. The Quebec Beckman shows factitiously high variation, secondary to the elevated Beckman analytical variation compared to Quebec Capillarys and Roche assays which demonstrate overlapping variation.

One thing that becomes clear from studying FIGS. 20 and 21, is that the analytical methods contribute to the total HbA1c variations with the more precise (diamonds and triangles) assays helping to demonstrate patient stability more than the less precise assays. That is, the less precise assay tends to demonstrate patient instability more than the Capillary and Roche assays, regardless of the patient.

Illustration 2: Electrolytes and Metabolites

Electrolyte and metabolite measurements are probably the most popular tests done on healthy and ill patients alike. Sodium is arguably the most important extracellular electrolyte. Multiple physiologic mechanisms exist in the mammal to maintain the extracellular sodium at nearly constant levels (variation of sodium concentration in the human is about 1%). Thus, sodium levels are a good indicator of an abnormal condition in a patient.

Figure 22:
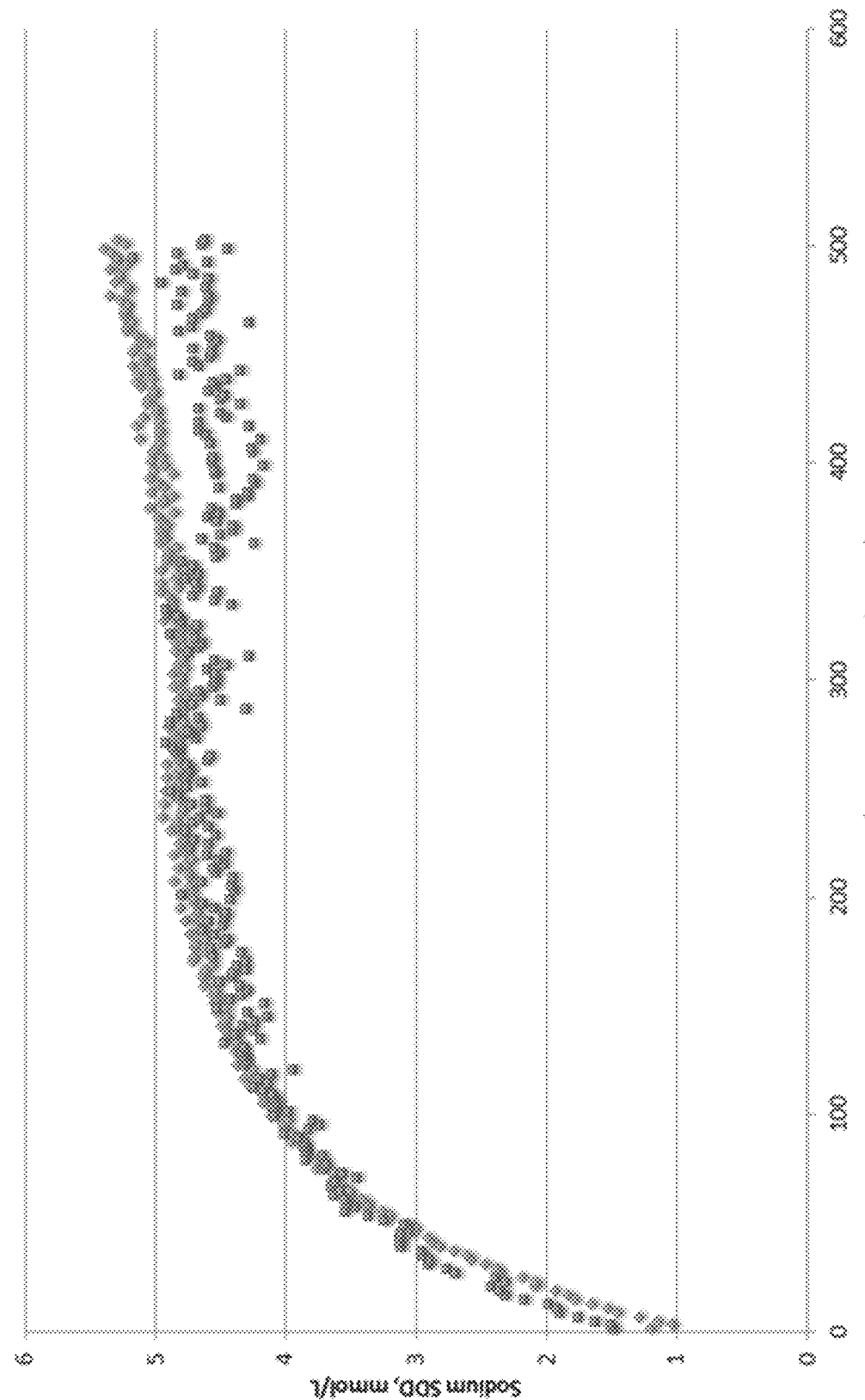
FIG. 22 shows that the LTSDD of two different sodium assays that are roughly the same, but the GEM (square) points, tend to be more spread out with some low variation points that recur every 24 hours.

FIG. 22 shows that the LTSDD of two different sodium assays that are roughly the same, but the GEM (square) points, tend to be more spread out with some low variation points that recur every 24 hours. A resourceful observer will note that the diamond line demonstrates less analytic error at time 0, but overall, the lines are roughly equivalent for the first 400 hours. In a very recent paper, it is postulated that the 24-hour alternation of high and low points is due to a calibrator that is run at 3 AM. Sadly, the action of this calibrator appears temporary, lasting slightly more than 4.5 hours. FIG. 22 illustrates a plot of LTSDD of ICU patients sodium measured with the GEM 4000 (square points) and the Radiometer 800 (diamond points).

Figure 23:
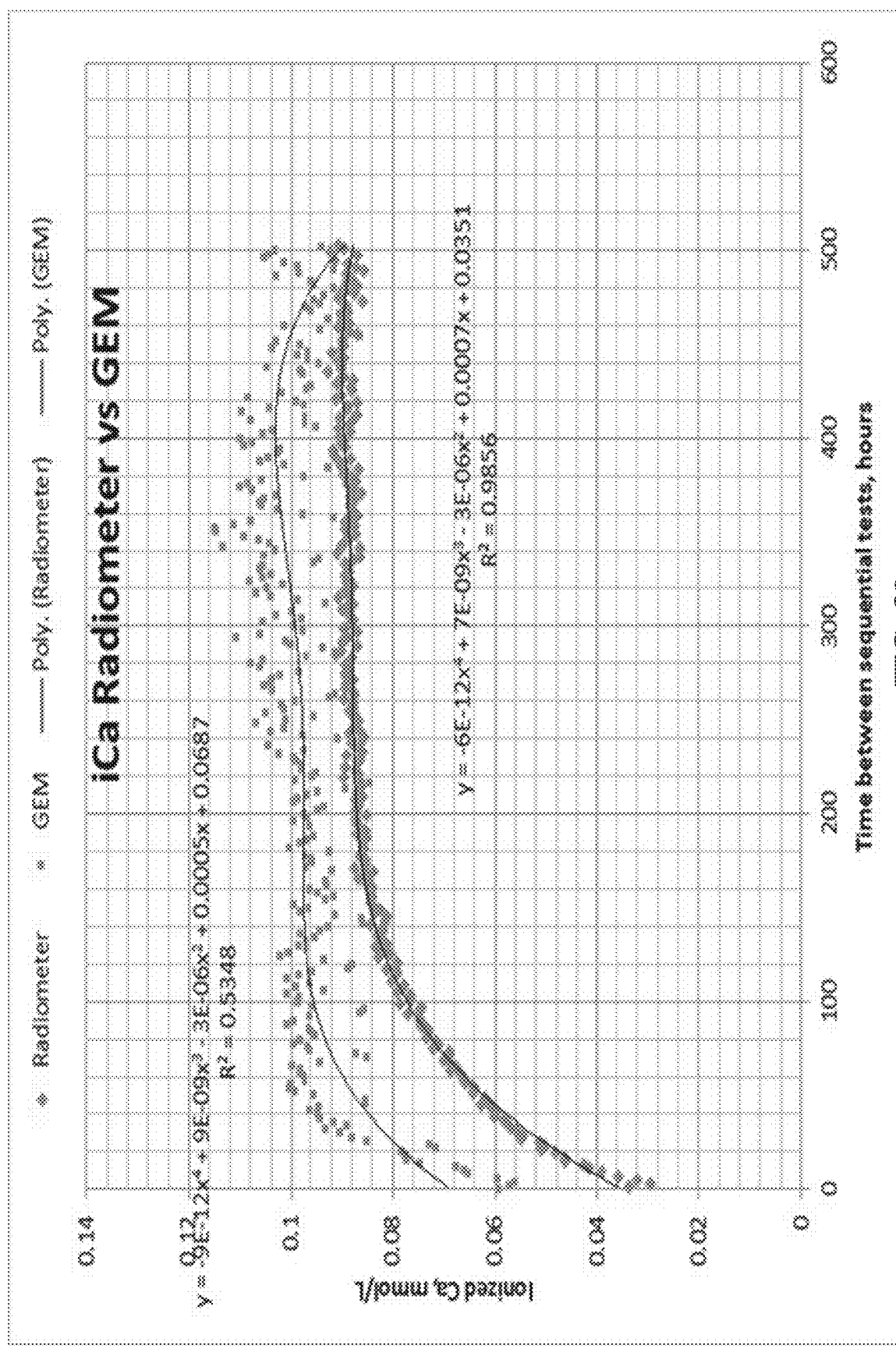
FIG. 23 illustrates, by way of example, a diagram of an embodiment of SDD for ionized calcium using GEM 4000 and Radiometer assays.

The GEM 4000 assay for ionized Calcium (iCa) patterns (square points) in FIG. 23 are very different from the Radiometer patterns (diamond points). Similar to the GEM sodium line, there is about a 24-hour rhythmicity in the square iCa SDD points with some of the lower GEM points approaching the diamond points, but overall the diamond Radiometer SDD performance is superior to that of the square GEM points.

Figure 24:
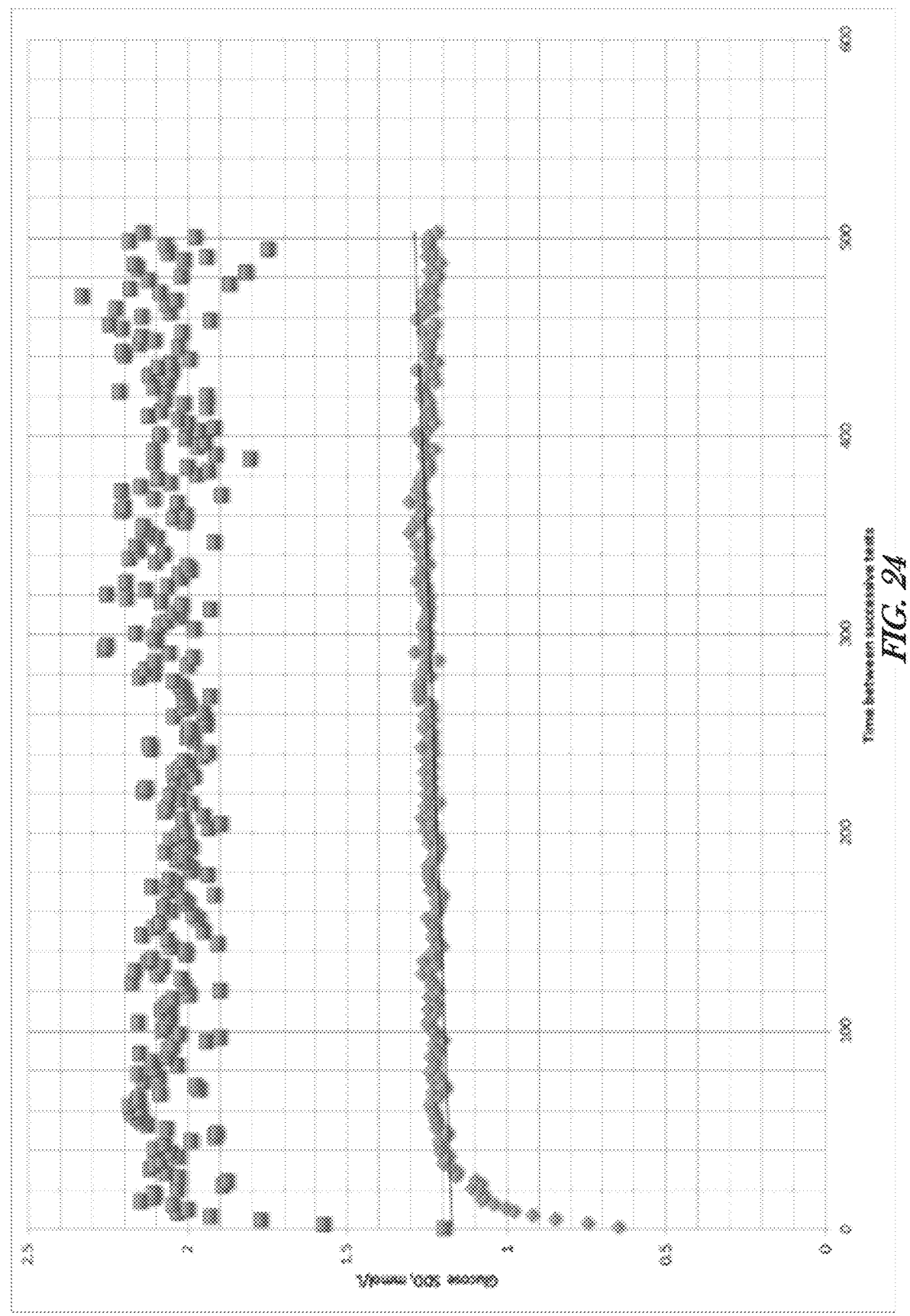
FIG. 24 illustrates, by way of example, a diagram of an embodiment of of SDD for glucose using GEM 4000 and Radiometer assays.

GEM and Radiometer glucose SDD graphs show the same tendency of the GEM lines to be much broader than the Radiometer and the 24-hour pattern of low and high points can be discerned in the GEM LTSDD. This is shown in FIG. 24 in which the square points represent SDD of the GEM assay and the diamond point represent SDD of the Radiometer assay. FIG. 24 illustrates the SDD for glucose for the GEM and Radiometer assays.

Illustration 3: Lipids, Inlcuding Cholesterol, HDL Cholesterol, nonHDL Cholesterol and Triglycerides For decades, the measurement of lipids has been preceded by a 10 to 12 hour fast. Authorities have begun to discount the value of the fast, stating that fasting is inconvenient to the patient, and the fasting requirement lessens the opportunities for blood-sampling and subsequent health improvement. Fasting primarily reduces the triglyceride component. As many more patients exhibit treatable cholesterol abnormalities, patients should be free to provide blood for lipid studies at their own convenience and without 10 to 12 hour fasts. The effect of non-fasting status on lipid concentrations was measured by calculating the LTSDD of thousands of lipid panel results obtained over the course of 3 years from Calgary Laboratory Services. This dataset is from a predominantly outpatient population. The results were separated by fasting status with data from patients who either fasted for more than 12 hours or who did not meet the criteria for fasting (fasted for less than 12 hours). The dataset included patients of a range of ages and included both male and female patients.

FIGS. 9*a*, 9*b*, 9*c*, 9*d*, 10*a*, 10*b*, 10*c*, and 10*d* of U.S. Provisional Patent Application Ser. No. 62/538,176 referenced supra, compare the LTSDD of fasting and non-fasting lipids. Also presented in these Figures are frequency histograms representing the number of lipid pairs and the separation between successive lipid testing.

In addition to the SDD transformation, the SDD numbers were divided by the patient mean/median to obtain the relative variation (in percentages), which is typically used to determine the overall acceptability of the analytic method or to even contemplate whether non-fasting is equivalent to fasting. Series 2 (darker) represents the fasting patients which vastly outnumber the non-fasting patients. FIGS. 9*c* and 10*c* show the numbers of each of these groups expressed over the two years that they were sampled and measured.

The darker fasting points are much more continuous as their SDD estimates are more accurate, being based on the incorporation of thousands of points. Long-term trends are obvious in the data with probably the most pronounced in the season variation. At one year, the variation is the least (an implication of this finding can be that patients should have their testing repeated only yearly; otherwise all kinds of seasonal components including weather, activity, or diet can complicate the interpretation of patient lipid levels). FIGS. 9c and 10c probably indicate over-testing as many tests are repeated at 4, 8 and 26 week intervals. What is quite evident is, for the total cholesterol and HDL cholesterol, the biological variation of the non-fasting lipids is equivalent to the fasting lipids.

What follows shows that the SDD curves may be expressed as an exponential equation with a Taylor's Series approximation to fit the line derived from the analysis of the short time intervals. Assume that the body has a fixed level of a given analyte that it is trying to maintain; however, there is also (biological) noise. If we denote the analyte by A, this can be expressed mathematically as the following stochastic differential eqn:

$$\frac{dA}{dt} = \frac{1}{\tau}(A_\infty - A) + D\Delta\delta_{ij}$$

Figure 25:
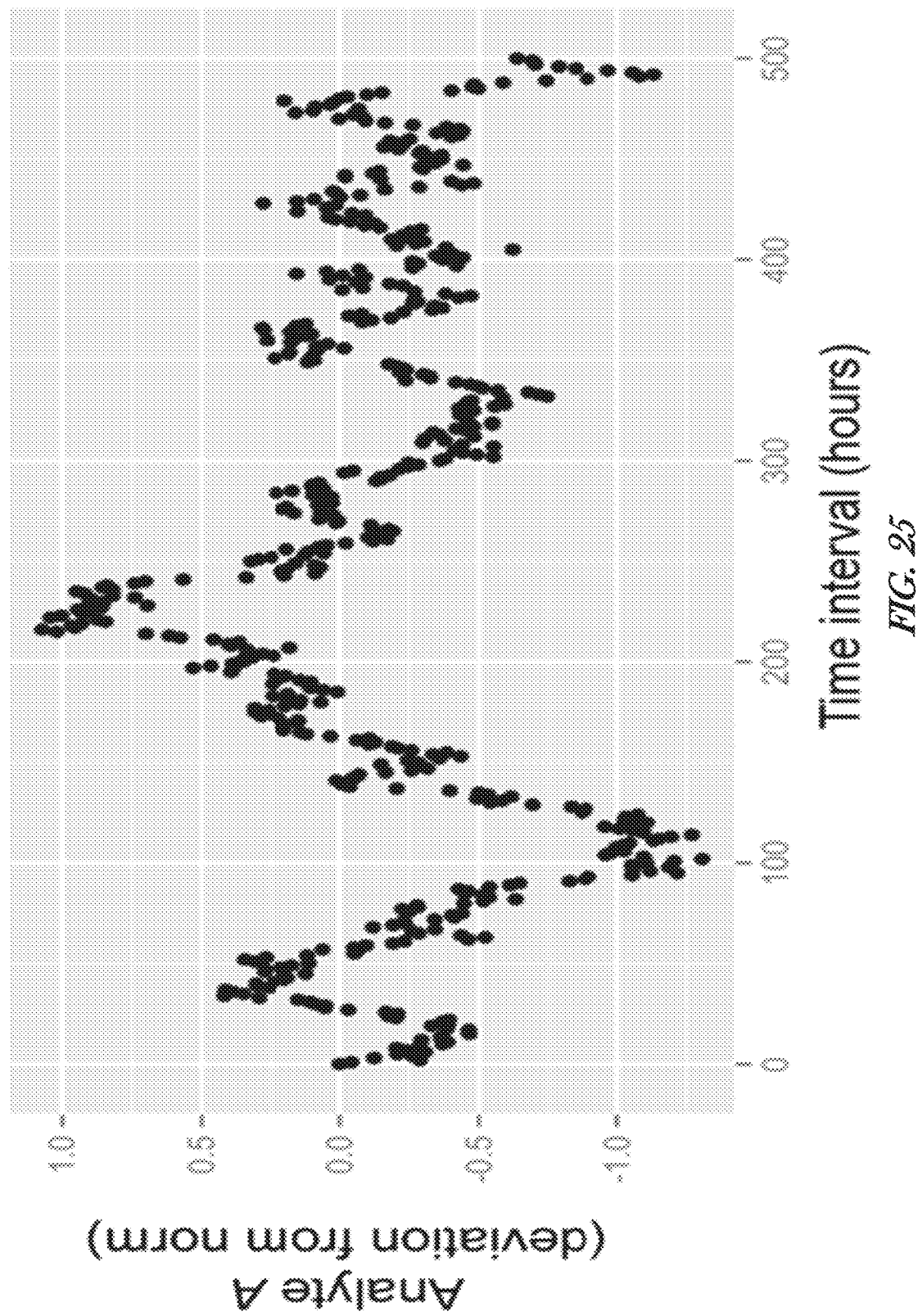
FIG. 25 illustrates, by way of example, a diagram of a graph of a hypothetical analyte measurement distance from normal (e.g., average, such as median or mean, or the like).

Here, A is the level of the analyte (a function of time), $A_\infty$ is the analyte steady-state value, $\Delta\delta_{ij}$ is uncorrelated (Gaussian) noise, D is the magnitude of the noise, and $\tau$ is the timescale with which the analyte returns to steady state after a perturbation. It can be shown that the solution to this is an exponential function. FIG. 25 illustrates an example realization.

Figure 26:
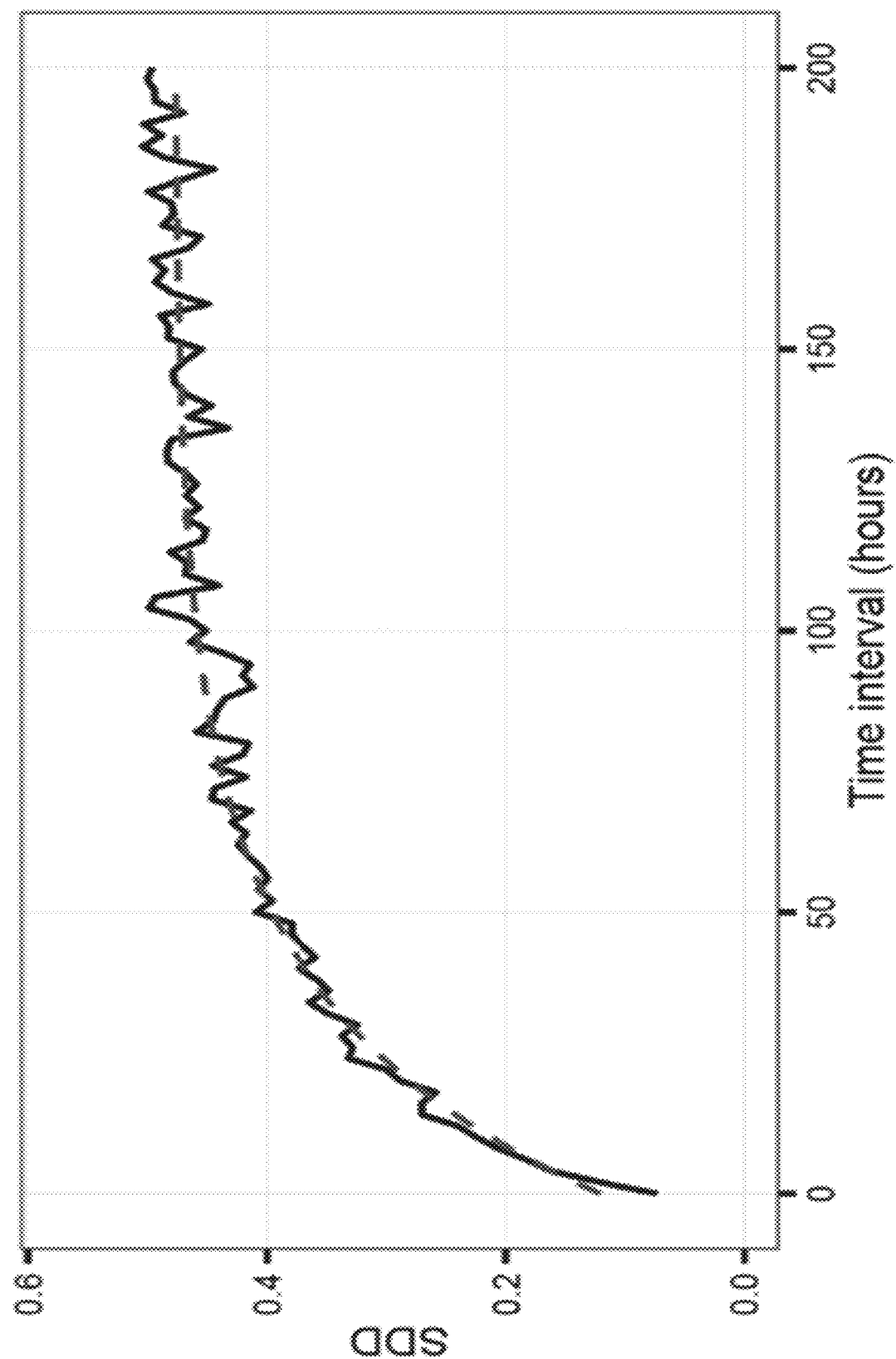
FIG. 26 illustrates, by way of example, a diagram of an embodiment of simulated data of an analyte (solid line) and an exponential fit to the data (dashed line).

If sample results are generated using lots of patients with this simple scheme, and analyzed, the results look like curves produced from analyzing patient data (see previous SDD curves). FIG. 26 illustrates an SDD curve for the data shown in FIG. 25.

The solid line in FIG. 26 is the simulated data, and dashed line is the exponential fit to the data. This curve is the same structure that the SDD data has, suggesting that a simple interpretation of a steady-state analyte value with biological noise can explain the data. It can be demonstrated that an exponential fit works well using the functional form:

$$SDD = Y_\infty - (Y_0 - Y_\infty) \cdot \exp(-t/\tau)$$

In a Taylor series:

$$e^x = 1 + x + \frac{x^2}{2!} + \frac{x^3}{3!} + \ldots$$

In this case, $x = -t/\tau$, so $$e^{-t/\tau} = 1 + (-t/\tau) + \frac{(-t/\tau)^2}{2!} + \frac{(-t/\tau)^3}{3!} + \ldots$$

Combining the functional form and the Taylor series expansion:

$$SDD = Y_\infty - (Y_0 - Y_\infty) \cdot \left(1 + (-t/\tau) + \frac{(-t/\tau)^2}{2!} + \frac{\left(-\frac{t}{\tau}\right)^3}{3!} + \ldots\right)$$

Figure 27:
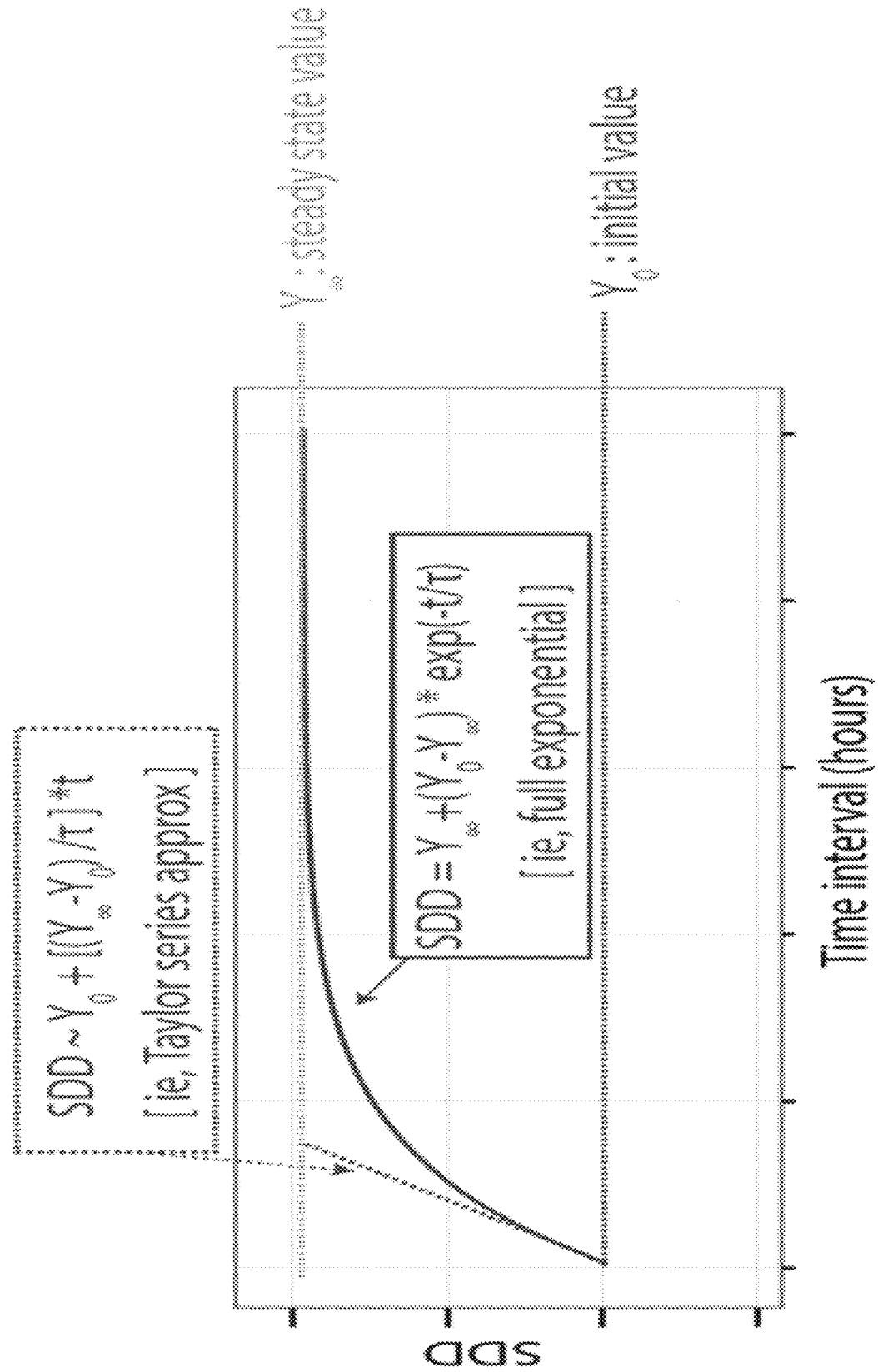
FIG. 27 illustrates, by way of example, a diagram of an embodiment of an exponential curve with explanation of the different states corresponding to the curve.

Note when t is small, the squared term, cubic term, etc. are very small, so this SDD equation can simplify to:

$$SDD \approx Y_\infty + (Y_\infty - Y_0) \cdot (t/\tau)$$

which is a line (constant term+term linear in time). Geometrically, this can be viewed as illustrated in FIG. 27.

Note in small time intervals, the linear approximation looks almost identical to the full exponential equation.

Figure 28:
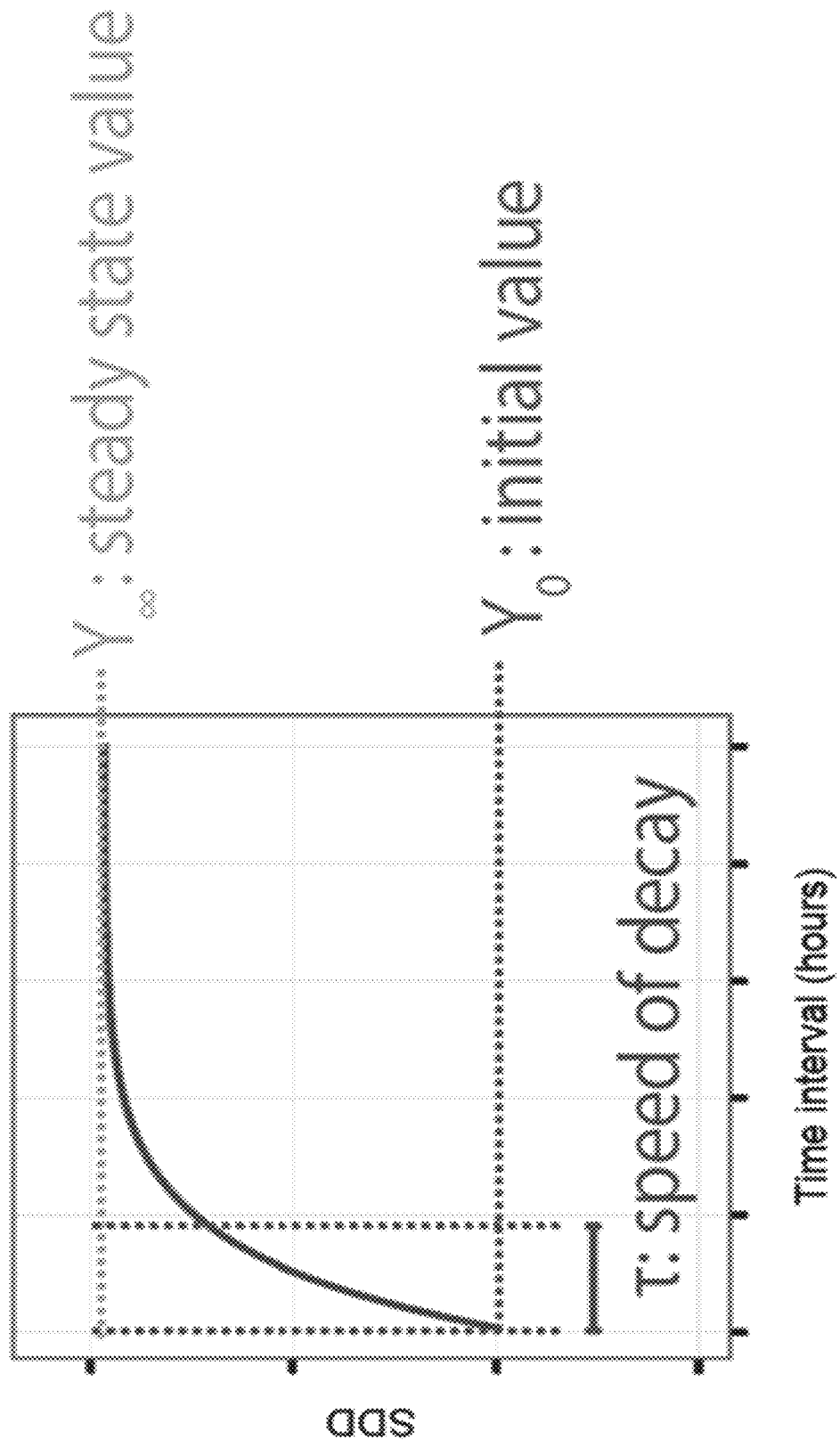
FIG. 28 illustrates, by way of example, another diagram of an embodiment of an exponential curve with explanation of the different states corresponding to the curve.
Figure 29:
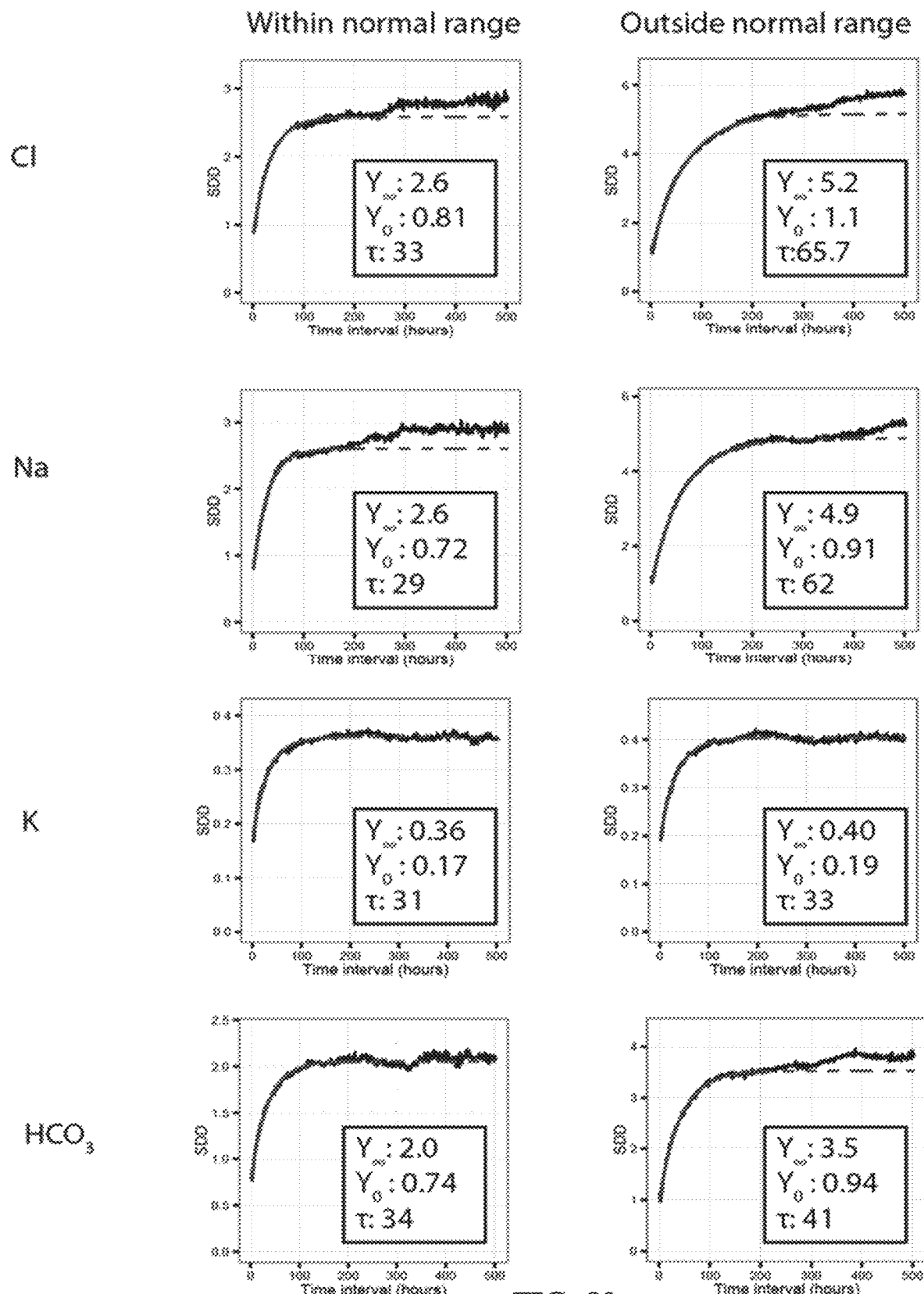
FIG. 29 illustrates, by way of example, experimental data (darker points) fit with an exponential (lighter line) between t=0 and t=200 for a variety of analytes; the exponential outside of this fit range is shown with a dashed line.
Figure 30:
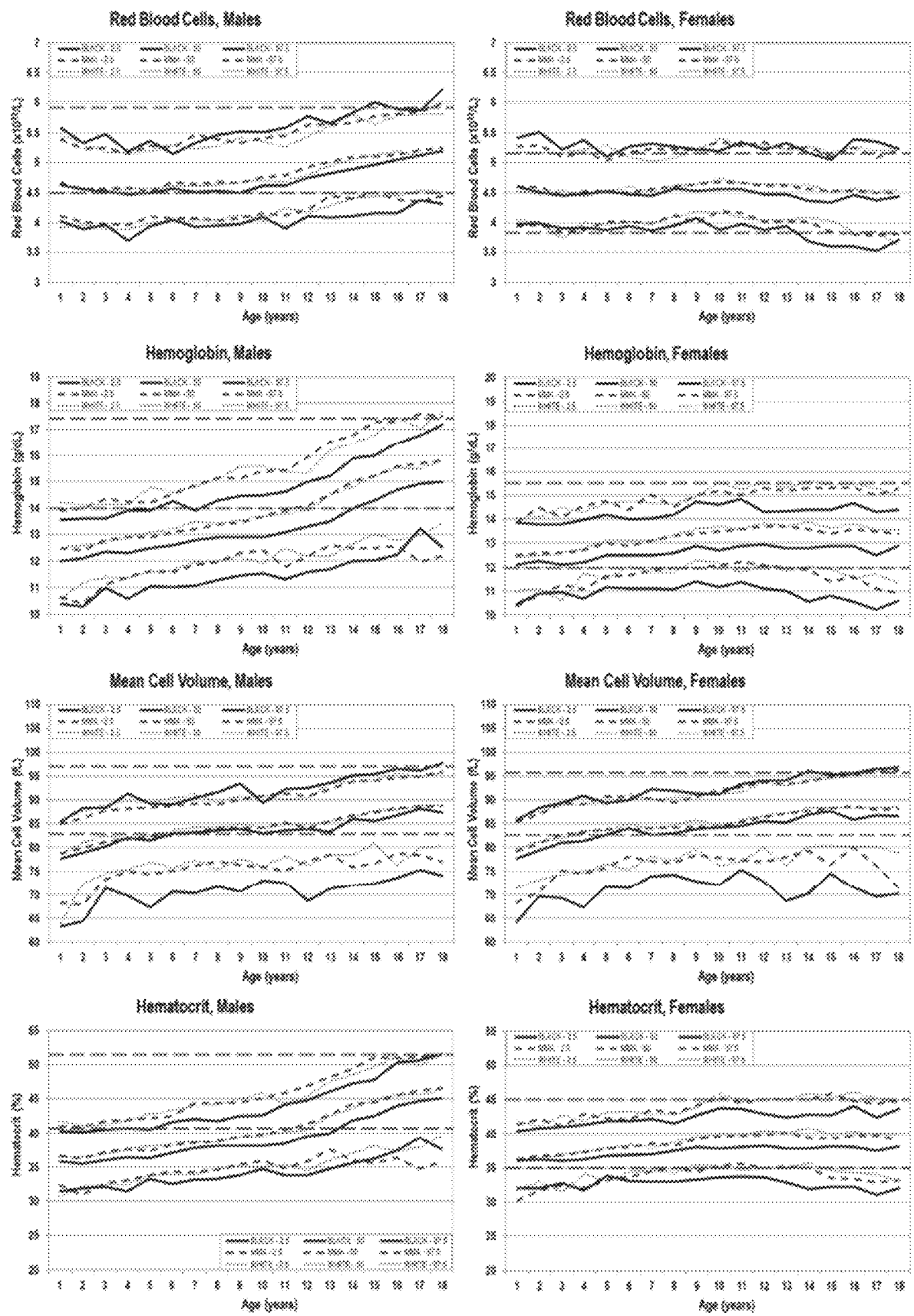
FIG. 30 illustrates, by way of example, experimental and corresponding fit for a variety of analytes and patient demographics.

A quick summary on exponential fit to standard deviation of deltas is provided:

Arithmetically, fit is:

$$SDD \approx Y_\infty + (Y_\infty - Y_0) \cdot (t/\tau)$$

where $Y_\infty$, $Y_0$, $\tau$ are fit parameters. Geometrically, this can be viewed as in FIG. 28. In FIG. 29, experimental data (darker points) is fit with an exponential (lighter line) between t=0 and t=200; the exponential outside of this fit range is shown with a dashed line. FIG. 30 illustrates, by way of example, experimental and corresponding fit for a variety of analytes and patient demographics.

Delta Check Application

In one or more embodiments, these curves can be used to determine the delta check limits that laboratory computer systems use to identify patients with sufficient changes in analyte level. For the most part, these limits are non-statistical and arbitrarily large. Sometimes, they are based on the patients' level; sometimes they are universal for all patients. A computer program can examine data generated by a hospital over one year (for example) and, using an SDD analysis and expression as an exponential, the clinical laboratory computer can start using delta check limits that are optimized for their patients and their selection of instruments. The curves can represent the SDD limits, such as can be multiplied by a specified constant, such as to reduce the numbers of false positives, false negatives, or the like.

Discovering Over-Ordering and Abnormal Variation with the SDD Analysis

To the student of biologic variation, there are two types of biologic variation, the usual, normal level variation and variation that exceeds normal limits. What the clinician observes is a mixture of the patient's biologic variation and the instrument's analytic variation. It is clinically useful to evaluate inpatients and outpatients to selectively demonstrate a) variation that is within normal limits, b) increased variation that is expected and c) increased variation that is unexpected.

Biologic Variation that is Within Normal Limits

In cohorts of patients in Ontario and British Columbia it has been estimated that laboratory testing is growing by 4 to 5% per year. The increase in testing may be due to testing associated with chronic disease, such as diabetes, kidney, or cardiovascular disease. Often, the testing is done and there is no additional follow up or therapy. In hospitals, testing tends to be repeated daily in patients who are expected to be transferred to stepdown units or to be discharged. The SDD analysis demonstrates that a cohort of patients' laboratory variation is normal. This finding can be directed to entity that ordered the test, such as to reduce his/her test ordering. Information like this can be made more predictive, if the patient results are a large distance from the abnormal or normal zone and the patients' biologic variation was within normal limits. Ultimately, less tests may be ordered.

Biologic Variation that is Increased and Expected

After many types of surgeries and medical procedures, laboratory tests may become predictably abnormal, signaling to the clinician that the laboratory variation is increased, but expected. This might be helpful to the physician or medical personnel in making a diagnostic.

Biologic Variation that is Increased and Unexpected

Signaling that the laboratory tests are varying more than expected may be helpful in situations that the clinician could intervene. Examples include creatinine, a marker of renal failure, and early indicators of decreased hemoglobin and platelets.

Example of Demonstrating the Biologic Variation is within Normal Limits for the Purposes of Test Reduction Evaluation of the patient's biologic variation in the context of patients waiting for discharge and laboratory testing is performed on a daily basis. Evaluations of the biologic variation can be incorporated into assessment of the test levels relative to the reference interval. The results of these tests can more accurately signal whether it is the patient's analyte instability or the variation of the laboratory analyzer that is responsible for the change in measured value.

Prior to the patient results being compared to the SDD limits, for each analyte, the individual tests for the relevant time interval can be compared to the normal range (health associated reference interval). If the patient results are within the appropriate age/gender/ethnicity/waist circumference reference interval, there may be less risk than if the biologic variation is increased. There is even less risk if the results are not abnormal and at or near midpoint between the upper and lower normal bounds. The figure below shows composite reference interval graphs for the hematology analytes, red blood count, hemoglobin, mean cell volume and hematocrit for males and females of white, black and Mexican ethnicities.

To evaluate the stored results of a patient, their age, gender, ethnicity or waist circumference can be input into a computer program and the current patient results can be compared to the age appropriate, ethnicity appropriate, gender appropriate, or waist circumference appropriate reference interval.

Assessment of the Biologic Variation of an Individual Patient's Analyte

It may be important to detect increased biologic variation as rapidly as possible. While two observations are the smallest number to provide a measure of variation; the running mean and standard deviation of the last 4 consecutive analyte values can be determined. The running standard deviation can be compared to a multiple of a smoothed SDD. If large numbers of patients or large numbers of analytes are being examined in real time to feedback the existence of a significant trend, then the running SDD multiple may exceed at least SDD×3 limit, such as to reduce the number of false rejections.

Whenever the multiple of the SDD is exceeded, the information about whether the new values are closer to the reference interval or further from the reference interval can be incorporated, such as to decide what information to relay to the clinical care group (e.g., medical personnel).

Figure 31:
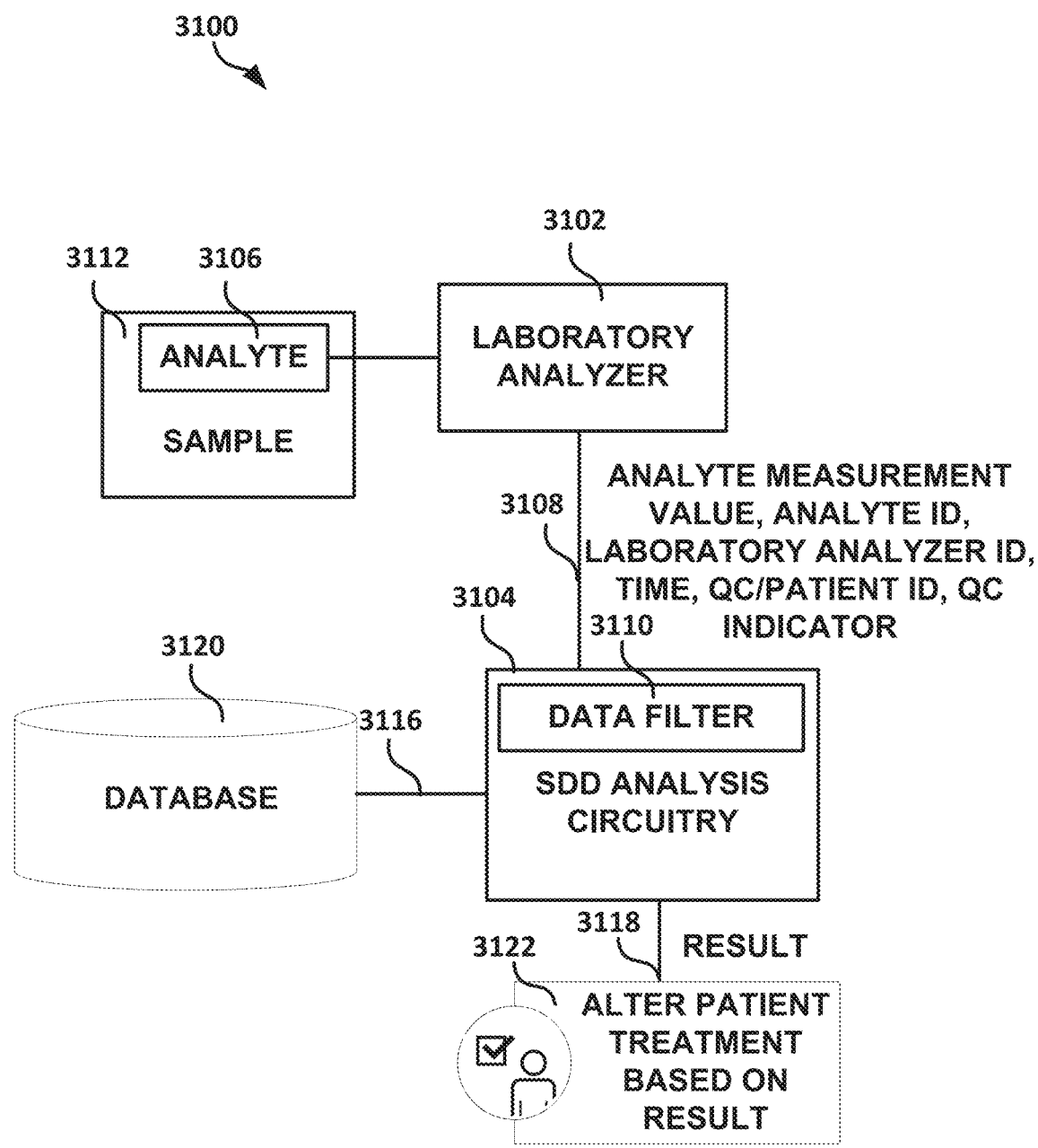
FIG. 31 illustrates, by way of example, a block diagram of an embodiment of a system 3100 for patient data analysis and care.

FIG. 31 illustrates, by way of example, a block diagram of an embodiment of a system 3100 for patient data analysis and care. The system 3100 as illustrated includes a laboratory analyzer 3102, SDD analysis circuitry 3104, a database 3120, and personnel 3122 to administer care to the patient.

The laboratory analyzer 3102 measures a value of an analyte 3106 in a sample 3112 from the patient. The patient sample 3112 can include blood, urine, marrow, tissue, hair, or the like. The analyte 3106 can be any analyte, such as those discussed herein including, but not limited to, hemoglobin A1c, troponin, calcium, sodium, chlorine, potassium, magnesium, hydrogen carbonate, glucose, creatinine, phosphate, uric acid, cholesterol (high-density lipoprotein (HDL), low-density lipoprotein (LDL), total, etc.), triglycerides, urate, retinol-binding protein, transthyretin, lactate, platelets, white or red blood cells, among others.

The laboratory analyzer 3102 performs an assay on the patient sample 3112 to determine a measurement value 3108 of the analyte 3106. The laboratory analyzer 3102 can include equipment from Roche, Beckman, GEM, Radiometer, other chemical measurement device manufacturer, or the like. There are many different types of laboratory analyzers. The measurement value 3108 from the laboratory analyzer 3102 can be associated with one or more of a laboratory analyzer identification (ID) that uniquely identifies the laboratory analyzer 3102, a time (date and time of day, sometimes including time zone), patient ID that uniquely identifies the patient from which the patient sample 3112 was obtained, or a QC indicator that identities whether the sample 3112 is from a patient or is a QC sample. For example, when the QC indicator is equal to "1" the measurement value can correspond to a result of the laboratory analyzer 3102 performing a measurement on the QC sample corresponding to a QC ID that uniquely identifies the QC sample. In this example, when the QC indicator is equal to "o" the measurement value can correspond to a result of the laboratory analyzer 3102 performing a measurement on the patient sample corresponding to the patient ID.

The measurement value 3108 can be provided to the SDD analysis circuitry 3104. The SDD analysis circuitry 3104 can include software, hardware (e.g., one or more electric or electronic components including a central processing unit (CPU), application specific integrated circuit (ASIC), field programmable gate array (FPGA), a state machine comprised of logic gates (e.g., AND, OR, XOR, negate, or the like) or multiplexers, transistors, resistors, capacitors, inductors, diodes, regulators, switches, analog to digital converters, digital to analog converters, or the like), firmware, or a combination thereof. The SDD analysis circuitry 3104 can determine an SDD based on data from the database 3120 or the laboratory analyzer 3102. The SDD analysis circuitry 3104 can determine based on an SDD plot of SDD values vs time between measurement of the SDD values.

The database 3120 can include historic measurement values along with associated identifying data. For example, the database 3120 can be indexed by patient ID, QC ID, laboratory analyzer ID, analyte ID, laboratory technician II), or the like. A laboratory technician is an entity that operates the laboratory analyzer 3102. An example data structure for an entry in the database 3120 can include the analyte measurement value, an analyte ID that uniquely identifies the type of analyze associated with the analyte measurement, a time the analyte measurement value was determined, and one or more of a laboratory analyzer ID, a QC/patient ID, a QC indicator, patient demographic data (e.g., height, weight, age, gender, waist circumference, race, or the like), or the like. The SDD analysis circuitry 3104 can include a data filter 3110 to produce a query that returns, from the database 3120, only specified data that meets the criteria specified by the data filter 3110 in the query.

The SDD analysis circuitry 3104 can produce a result 3118 based on the analysis performed thereby. The result 3118 can include one or more of: (1) refraining from performing another analyte measurement; (2) an indication of the patient's percentage change in measurement value along with an expected variation from the laboratory analyzer; (3) an indication that a laboratory technician is associated with greater than normal variation and performed the measurement using the laboratory analyzer; (4) an indication that the laboratory analyzer used to produce the analyte measurement is associated with greater than normal variation and the amount of variation associated therewith; (5) that the biologic variation of the patient is high based on the analyte measurement and that medication should be administered to regulate the high biologic variation; (6) use a different assay to make a measurement because the current laboratory analyzer produces results with too much analytical variation to be reliable; (7) whether or not the patient is to fast or not before a next measurement of the analyte; among many others.

The medical personnel 3122 can alter the patient treatment based on the result 3118. For example the medical personnel 3122 can (1) refrain from performing a next scheduled analyte measurement corresponding to the same analyte ID as the result; (2) adjusting an amount of medication used to regulate the analyte; (3) ordering the analyte measurement be re-performed by a different laboratory technician or using a different laboratory analyzer; (4) adding or removing a medication from the patient's intake schedule; (5) ordering another analyte measurement of the same analyte using a different assay; among others.

The data filter 3110, for example, can specify an analyte ID, time range, range of analyte measurement values, laboratory analyzer ID, laboratory technician ID, patient ID, QC ID, QC indicator, or the like. The corresponding data in the database 3120 that matches the specified characteristics can be returned to the SDD analysis circuitry 3104. The SDD analysis circuitry 3104 can then determine the SDD for the returned results and make a recommendation regarding the analyte measurement 3108 based on the determined SDD.

For example, to determine whether a laboratory technician is associated with higher than normal variation, the SDD of analyte measurements associated with a specific laboratory technician ID can be compared to other laboratory technicians who operate the same laboratory analyzer 3102. If the variation in the results is sufficiently high compare to that of other laboratory technicians (within a specified number of standard deviations from average, such as less than one, one, greater than one, greater than two, or the like) the laboratory technician can be associated with a higher than normal variation.

In another example, to determine whether a patient is to fast or not, variation of analyte measurements of a same analyte performed on fasting patients can be compared to variation of analyte measurements of a same analyte performed on non-fasting patients (note the analyte measurements can be from a same group of one or more laboratory analyzers to control for analytic variation). If the variation is sufficiently high comparatively, fasting/non-fasting can be important and selected accordingly. If the variation is the same, non-fasting can be selected so as to not burden the patient unnecessarily.

In yet another example, if all laboratory analyzers of a specific assay type are found to have higher analytic variation (based on an SDD of QC samples for example) than other assays, that assay type can be deemed unreliable. In the examples of FIGS. 21, and 23-24 it can be determined that the GEM assay is unreliable and the medical personnel 3122 can order the assay be performed in accord with a Radiometer assay. For such analyses, a laboratory analyzer type data field can be stored with data in the database 3120.

For a more specific analysis of whether the biologic variation is consistent with other like patients, the data filter 3110 can specify a query for data of a specific analyte ID and associated with patients of similar demographic characteristics, such as age, gender, waist circumference, race, weight, height, or the like. An SDD of the population of returned results can be compared to an SDD of the patients results. The corresponding variation can be compared to determine whether the patient's condition corresponds to an abnormal condition or a normal condition. The medical personnel 3122 can then take the next proper steps better informed.

Figure 32:
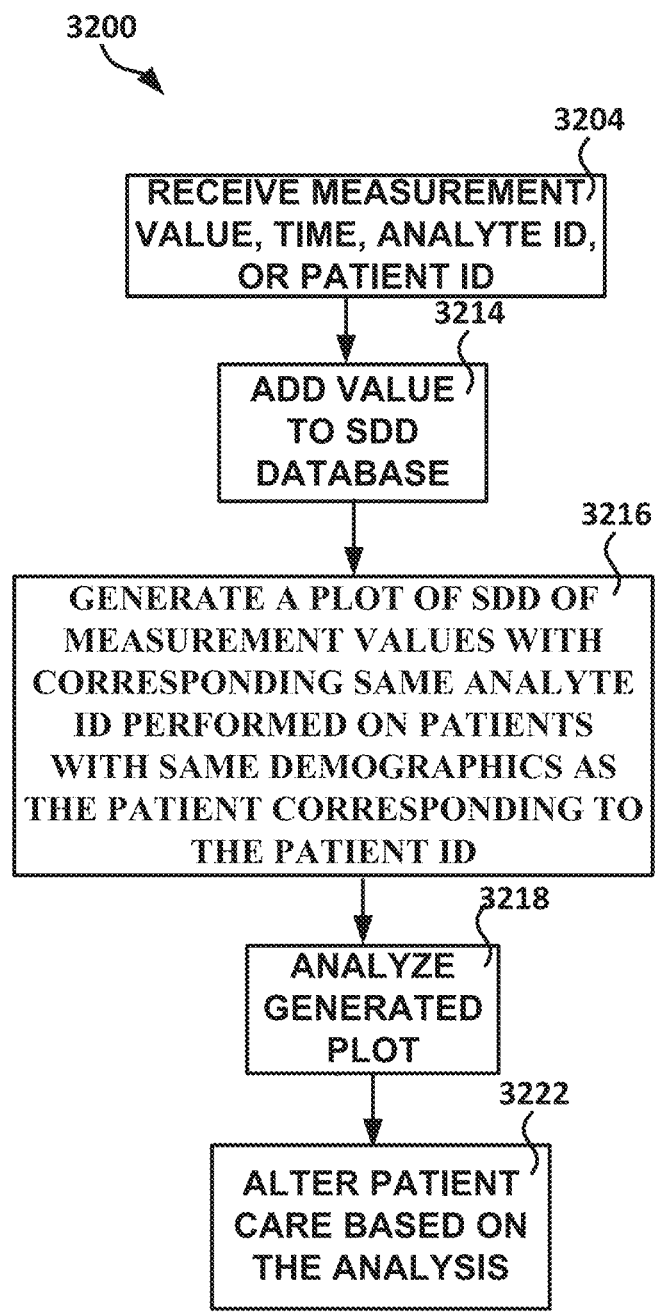
FIG. 32 illustrates, by way of example, a diagram of an embodiment of a method 3200 for altering patient treatment.
Figure 33:
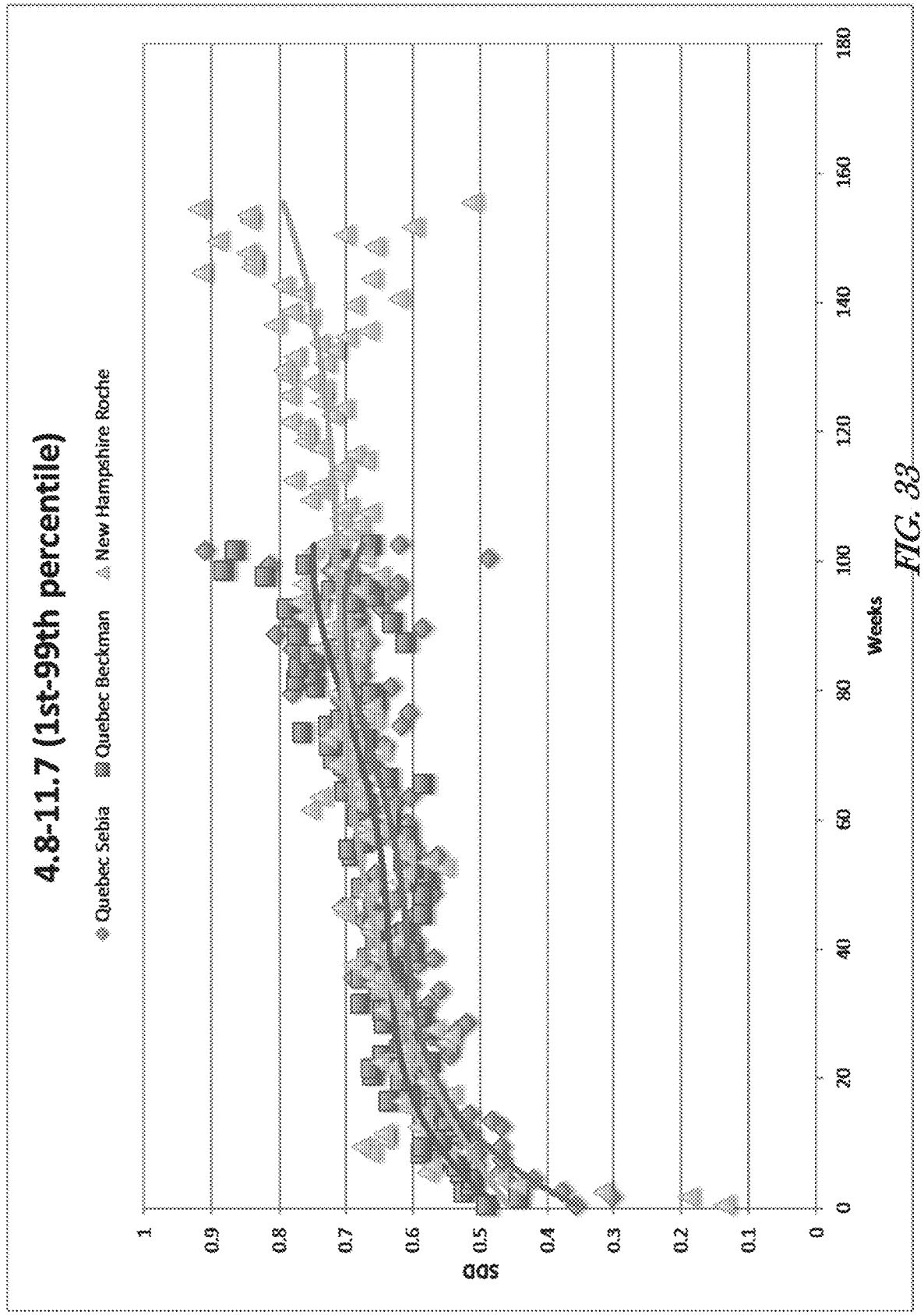
FIGS. 33-36 illustrate, by way of example, diagrams of graphs of embodiments of HbA1c for different ranges of patient results (e.g., 1 percentile (P) to 99 P; 1 P to 25 P, 25 P to 75 P, and 75 P to 99 P).
Figure 34:
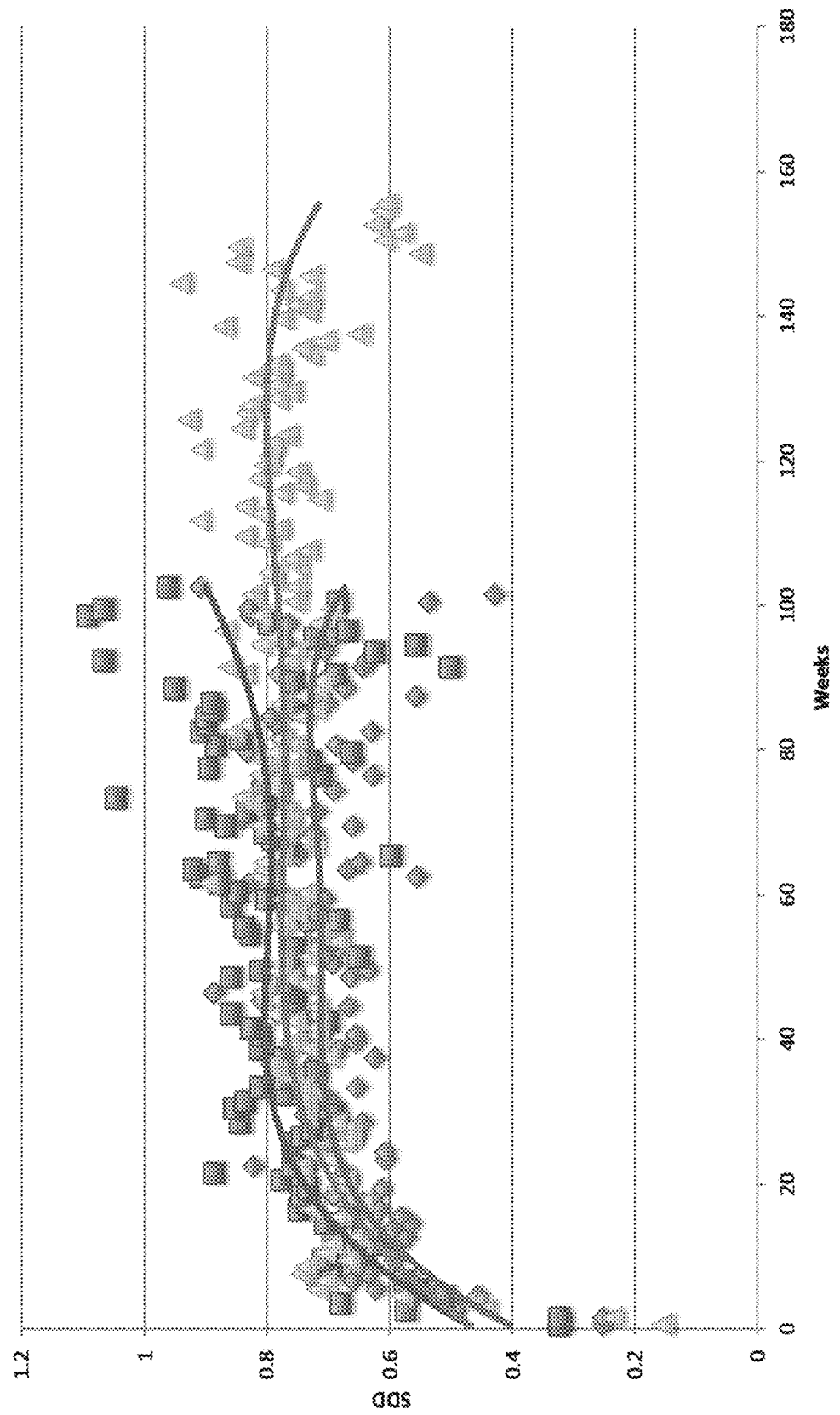
Figure 35:
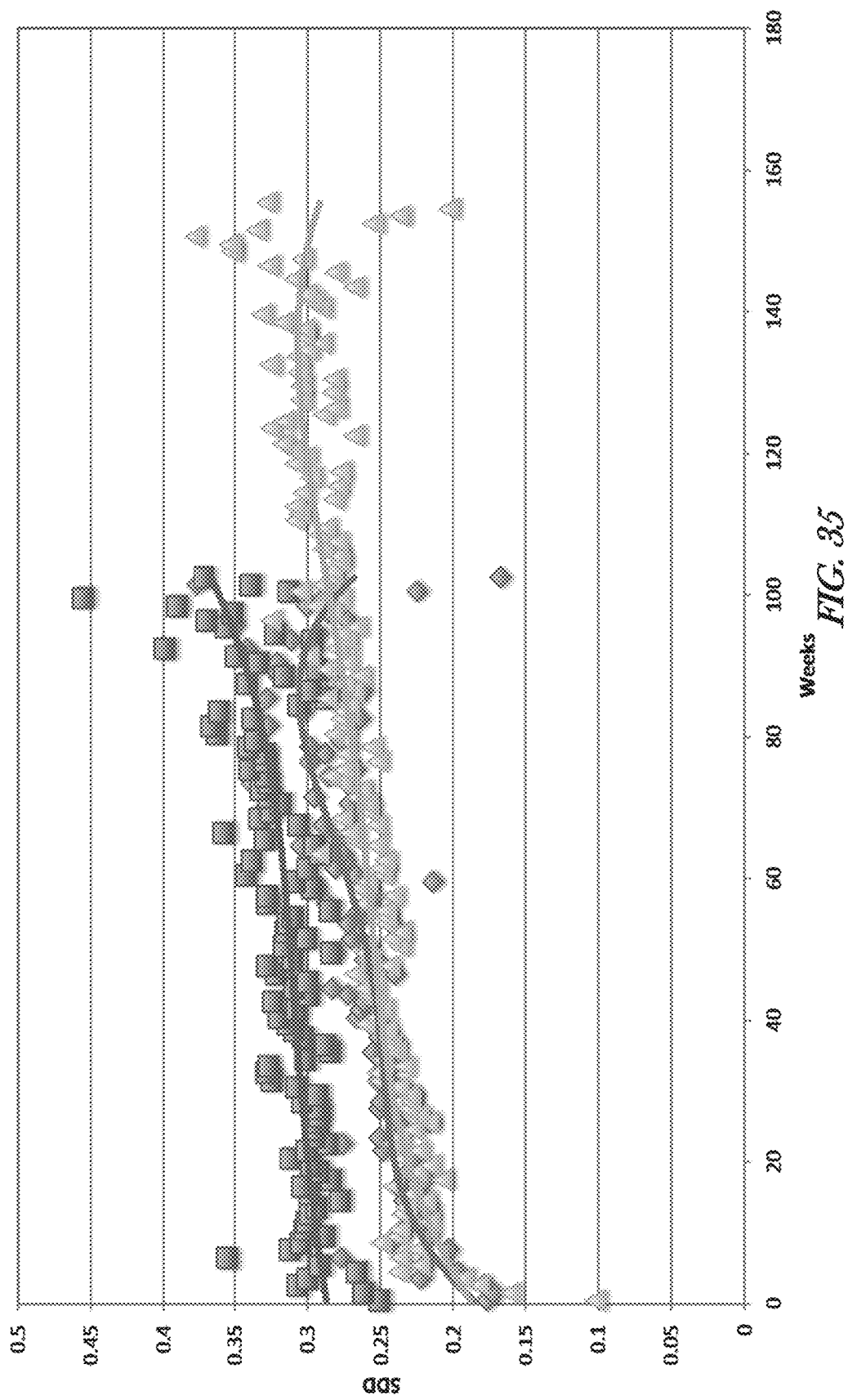
Figure 36:
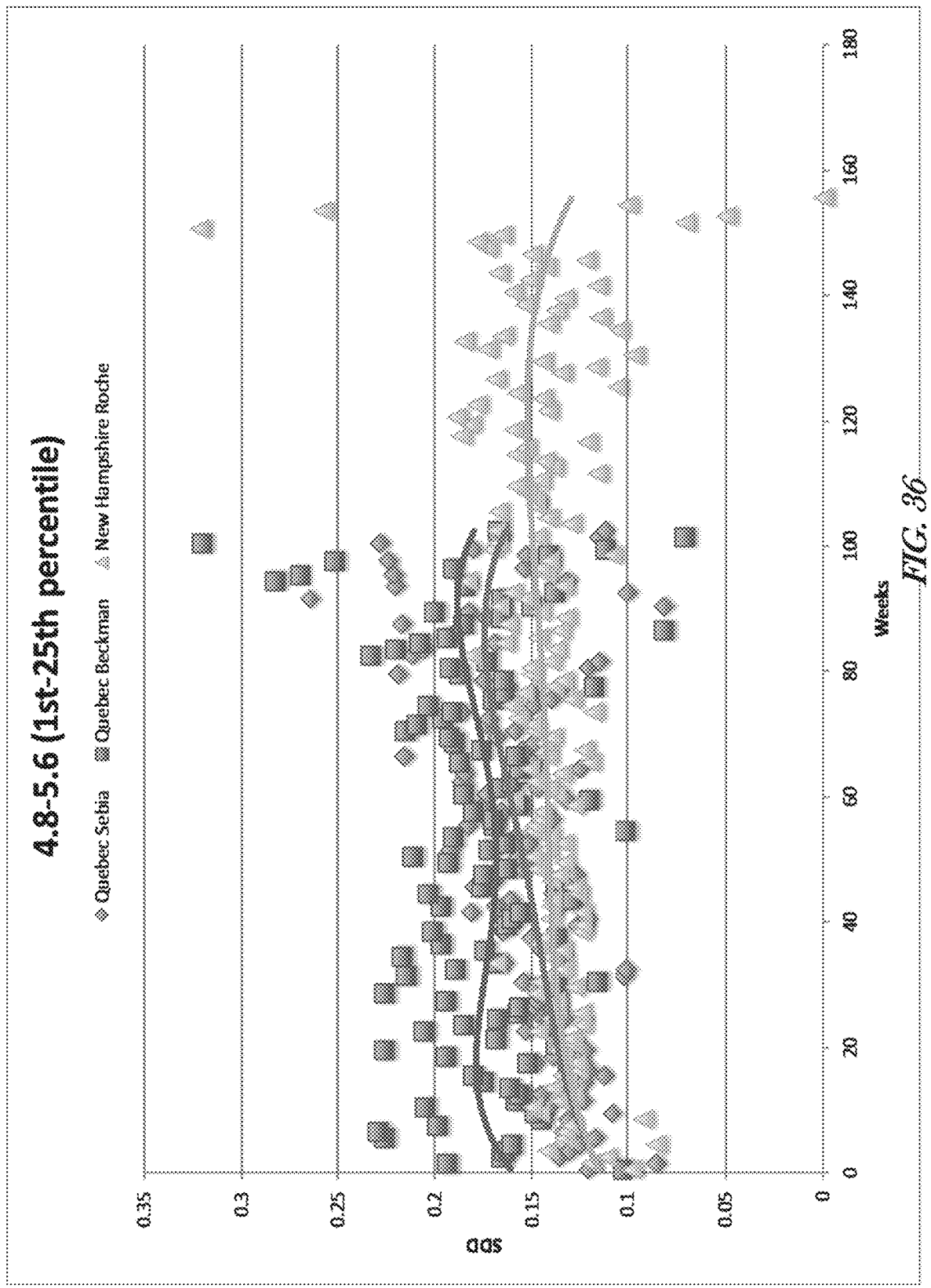

FIG. 32 illustrates, by way of example, a diagram of an embodiment of a method 3200 for altering patient treatment. The method 3200 as illustrated includes receiving one or more measurement values and corresponding time at which the measurement value was determined, analyte ID, laboratory analyzer ID, or QC ID/patient ID, at operation 3204; adding the measurement value to the SDD database, at operation 3214; generating a plot of SDD of measurement values with corresponding same analyte ID performed on patients with same demographics as the patient corresponding to the patient ID, at operation 3216; analyzing the generated plot, at operation 3218; and altering patient care based on the analysis, at operation 3222.

Use of Techniques in Real Time with Biological/Analytical Limits

Assume that the amounts of biologic variation and analytic variation have been determined for each laboratory analyzer of the laboratory method used and for typical patients being evaluated with the laboratory method (for patients with low-normal variation (PLNV), patients with normal variation (PNV) and patients with normal variation to normal-high normal variation (PNVHNC)).

The approach to gaining these variations is described elsewhere herein and summarized here. The long term (LT) variation of specimens can be determined. This variation is applied to the interpretation of the analysis of patient specimens. Repeated patient measurements (patient measurements of a same analyte) can be considered analogous to the repeated measurement of aliquots of a single patient sample over months or years. For hemoglobin A1c (HbA1c) or other analyte interpretations, a measurement of a prior specimen is compared to a measurement of a new specimen. In the models herein, the variation of all possible measurement pairs is calculated; results are grouped and compared with subsequent measurement results as long as the time interval between the two measurements is the same. The standard deviation of the differences sometimes called standard deviation of the deltas (SDD) of the groups of measurement pairs provides an average variation for each time interval. Graphs of the LT SDD versus the time interval easily illustrate the effect of reagent lot variation or biased analytical runs.

Graphs of the methods' LT intra-patient SDD variation for 4 HbA1c ranges: 1) 1st P to the $99^{th}$ P; 2) the 75th P to 99th P (high results, consistent with poor control); 3) 25th P to 75th P (middle of the road results); and 4) 1st P to the 25th P (the lowest results representing patients with non-elevated HbA1c or patients with good control) were generated. These graphs are provided in FIGS. 33, 34, 35, and 36. Highly abnormal HbA1c (>99th percentile (P) or <1st P) were removed as these outliers might artefactually elevate the SDD. In the SDD calculations, the shortest time interval was one week and extended to 103 weeks for the Beckman and Sebia and up to 156 weeks for the Roche. To better appreciate the SDD trends, the data were fitted with a 4th degree polynomial. Finally, pertinent imprecision information from contemporaneous College of American Pathologists (CAP) proficiency testing (PT) reports were extracted and generated combinations of likely biologic and analytic variations that explain the observed HbA1c variation at 26 weeks (½ year or 6 months), which represents a typical interval for repeating HbA1c.

Then for every test that is performed for every patient with representative disease that require testing for diagnosis or therapeutic adjustment (e.g., diabetes (HbA1c), thyroid supplementation (for thyroid deficiency or with a diagnosis of thyroid cancer and requirement for extra thyroid supplementation to prevent thyroid gland stimulation), patient with chest pain (troponin ordered to rule out/rule in myocardial infarction), platelets, electrolytes (e.g., magnesium, potassium, sodium, calcium, phosphate, chloride, etc.), or the like, identify to which range the patient measurement corresponds.

For every test that is performed for every patient with representative disease that require testing for diagnosis or therapeutic adjustment (using HbA1c and FIGS. 33-36 as an example), the sum of the variation of the patient and the Roche method at one year—a usual time that a patient can be retested for an updated diabetes diagnosis. One year is also the period that the type 2 diabetes patient is retested to determine worsening or improvement of diabetic status.

PLNV (1 year, Roche, FIG. 36)=2×0.15%=0.3% (using a multiplier of 2 to establish the 95% limits).

PNV (1 year, Roche, FIG. 35)=2×0.25%=0.5%.

PNVHNV (1 year, Roche, FIG. 34)=2×0.7%=1.4%.

If HbA1c is well within normal limits for a patient being screened for diabetes (HbA1c value with ±PNV) then there is no issue. Example: patient being screened to determine whether he/she has diabetes and the HbA1c is 5%. The HbA1c limit to diagnose diabetes is 6.5%. The usual excursion for a patient with no diabetes would be 0.3%. A patient with a low screening value and an assumed maximum excursion of 0.3% would have a very low risk of diabetes. The next time for HbA1c measurement could be extended beyond the one-year cycle. If HBA1C is close to the decision limit of diabetes (6.5%), but lower than the decision limit, then the patient result and the maximum excursion could be added. If the sum is greater than 6.5%, then the patient is at high risk of developing diabetes and the patient should receive appropriate instructions in diet and exercise to delay the onset of diabetes.

The following can be done for a patient with type 2 diabetes:

1) If the new HbA1c is within the stable HbA1c target, then the HbA1c can be repeated one year later.
2) If the new HbA1c is beyond the acceptable HbA1c target, then appropriate measures must be taken to reduce the HbA1c, such as medication adjustments.
3) If the HbA1c is within 0.3% of previous HbA1c, the patient is classified to have stable diabetes.
4) If the HbA1c has increased by more than 0.5%, then appropriate measures should be taken to reduce the HbA1c, such as by adjusting medication.

Using such an interpretive approach with reduce the probability of over-diagnosis and overtreatment and result in more efficient and accurate medical practices.

Table 1 summarizes the coefficient of variation (CV) for the $1^{st}$ to $25^{th}$ percentile and the $25^{th}$ to $75^{th}$ percentile comparing the actual CV for a 100 sample by 26 week SDD of a median HbA1c, likely CV of biologic variation ($CV_b$), likely CV of analytic variation ($CV_a$), and total CV.

TABLE 1

Values of average biologic intra-patient variation and analytic variation associated with the 26 week SDD for Beckman, Sebia, and Roche for middle and low HbA1c ranges.

| Range | Beckman CV (%) | Sebia CV (%) | Roche CV (%) | Likely $CV_b$ | Likely $CV_a$ | Total CV ($CV_a^2 + CV_b^2)^{1/2}$ |
|---|---|---|---|---|---|---|
| $1^{st}$ to $25^{th}$ | | 2.6% | 2.5% | 1.5% | 2% | 2.5% Sebia, Roche |
| $1^{st}$ to $25^{th}$ | 3.2% | | | 1.5% | 3% | 3.4% Beckman |
| $25^{th}$ to $75^{th}$ | | 3.8% | 3.7% | 3.5% | 2% | 4.0% Sebia, Roche |
| $25^{th}$ to $75^{th}$ | 4.9% | | | 3.5% | 3% | 4.6% Beckman |

Reducing Cost by Reducing Unnecessary Analyte Measurements

The GEM 4000™ (Instrumentation Laboratory, Waltham Mass.) and ABL 800 (Radiometer, Copenhagen, Del.) are point-of-care analyzers, primarily used in critical care settings to measure blood gases, glucose, and electrolytes. Previous studies have shown that the GEM 4000 produces borderline low sigma tests results compared to the ABL 800. While physicians using a low sigma analyzer have recourse to retesting with point of care testing, they might simply send blood to the central laboratory. In this study, the number and costs of replicate tests sent to the central laboratory within 30 minutes of running the point of care test panel were analyzed.

Laboratory databases were mined for measurements of glucose and electrolytes using either twin GEM 4000™ instruments or twin Radiometer 800 ABL blood gas analyzers at either the Foothills Hospital adult ICU in Calgary, Alberta or the General Systems adult ICU at University Hospital in Edmonton, Alberta, respectively, between 2013-2016. Any concurrent testing (within 30 minutes) performed by the central laboratory Roche Cobas 8000™ or the Beckman DXc chemistry systems in Calgary and Edmonton, respectively, were counted. In Alberta, individual electrolytes and glucoses have been costed at about $5.00 per test.

Each patient with GEM 4000 testing averaged 6.1 central laboratory sodium measurements, compared to the average patient with ABL 800 testing who averaged 2.5 sodium measurements. For Na, Cl, bicarbonate and potassium, the rate of central laboratory testing for the GEM patients was roughly 2.2 to 2.4 times that of the ABL 800. The yearly total cost for repeated central laboratory Na, Cl, bicarbonate, potassium and glucose testing was $120,000 for the GEM patients and $45,500 for the ABL 800 patients.

One of the hidden costs of using a low sigma analyzer is the increased costs of redundant central laboratory testing. In addition to this extra testing which is presumably associated with the use of a low sigma analyzer, other less tangible factors should be considered when selecting an ABG analyzer including the cost of diagnostic error.

Better Understanding Human Chemistry Mechanisms

An assumption of the biologic analytic model is that biologic variation varies little. A normal range platelet biologic variation extends from 3 to 10% (median 7.7%). The wide platelet BV may be partially explained by the duration of a biologic variation study. As a general rule, the longer that biologic variation data are collected on individual patients, the larger will be the biologic variation (e.g. HbA1c).

Figure 37:
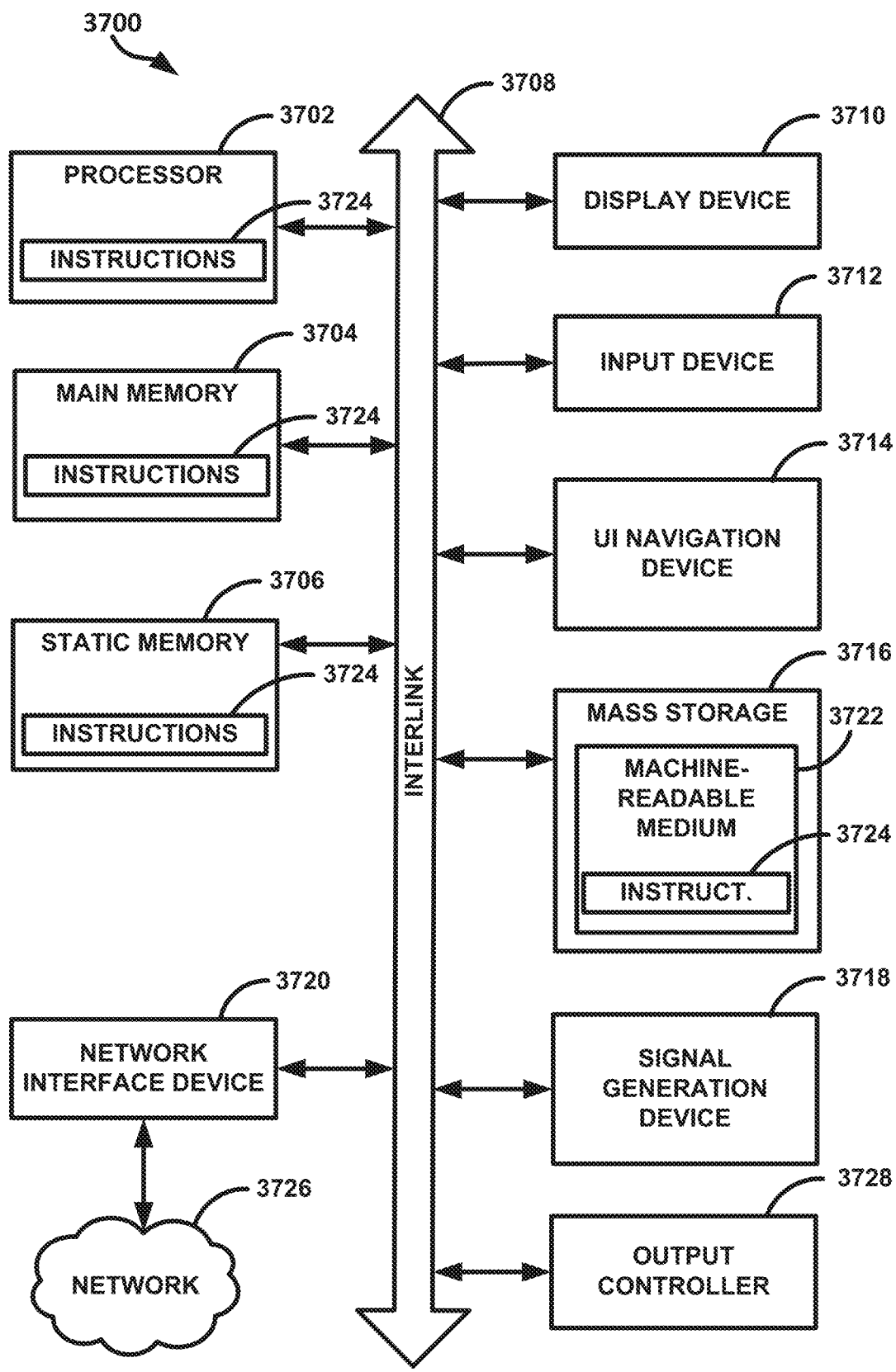
FIG. 37 illustrates, by way of example, a block diagram of an example of a device 3700 upon which any of one or more processes (e.g., methods) discussed herein can be performed.

Some studies are shorter term and have been conducted over periods of 1 to 3 days. These studies have produced BY ranging from 3% to 6%. Other studies have been done over 20 weeks and have generated BV of up to 10%. The relative platelet variation (measured over 48 hours) in thrombocytopenic patients is twice that of Buoro's short term variation in normal patients. The implication of this finding is that while platelets of thrombocytopenic patients are being consumed or sequestered in areas like the spleen, either the patient bone marrow is producing proportionally more platelets or else the patients are being treated with therapies such as steroids and platelet concentrate FIG. 37 illustrates, by way of example, a block diagram of an example of a device 3700 upon which any of one or more processes (e.g., methods) discussed herein can be performed. The device 3700 (e.g., a machine) can operate so as to perform one or more of the calibration, diagnosis, or analysis (e.g., methodologies) discussed herein. In some examples, the device 3700 can operate as a standalone device or can be connected (e.g., networked) to one or more items, such as a laboratory analyzer, a database. An item of the analyzer can include one or more of the items of the device 3700, or the device can implement at least a part of a middleware, cloud, distributed, or other solution to performing one or more of the methods discussed herein.

Embodiments, as described herein, can include, or can operate on, logic or a number of components, modules, or mechanisms. Modules are tangible entities (e.g., hardware) capable of performing specified operations when operating. A module includes hardware. In an example, the hardware can be specifically configured to carry out a specific operation (e.g., hardwired). In an example, the hardware can include configurable execution units (e.g., transistors, logic gates (e.g., combinational and/or state logic), circuits, etc) and a computer readable medium containing instructions, where the instructions configure the execution units to carry out a specific operation when in operation. The configuring can occur under the direction of the executions units or a loading mechanism. Accordingly, the execution units can be communicatively coupled to the computer readable medium when the device is operating. In this example, the execution units can be a user of more than one module. For example, under operation, the execution units can be configured by a first set of instructions to implement a first module at one point in time and reconfigured by a second set of instructions to implement a second module.

Device (e.g., computer system) 3700 can include a hardware processor 3702 (e.g., a central processing unit (CPU), a graphics processing unit (GPU), a hardware processor core, processing circuitry (e.g., logic gates, multiplexer, state machine, a gate array, such as a programmable gate array, arithmetic logic unit (ALU), or the like), or any combination thereof), a main memory 3704 and a static memory 3706, some or all of which can communicate with each other via an interlink (e.g., bus) 3708. The device 3700 can further include a display unit 3710, an input device 3712 (e.g., an alphanumeric keyboard), and a user interface (UI) navigation device 3714 (e.g., a mouse). In an example, the display unit 3710, input device 3712 and UI navigation device 3714 can be a touch screen display. The device 3700 can additionally include a storage device (e.g., drive unit) 3716, a signal generation device 3718 (e.g., a speaker), and a network interface device 3720. The device 3700 can include an output controller 3728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.

The storage device 3716 can include a machine readable medium 3722 on which is stored one or more sets of data structures or instructions 3724 (e.g., software) embodying or utilized by any one or more of the techniques or functions described herein. The instructions 3724 can also reside, completely or at least partially, within the main memory 3704, within static memory 3706, or within the hardware processor 3702 during execution thereof by the device 3700. In an example, one or any combination of the hardware processor 3702, the main memory 3704, the static memory 3706, or the storage device 3716 can constitute machine readable media.

While the machine readable medium 3722 is illustrated as a single medium, the term "machine readable medium" can include a single medium or multiple media (e.g., a centralized or distributed database, and/or associated caches and servers) configured to store the one or more instructions 3724. The term "machine readable medium" can include any tangible medium that is capable of storing, encoding, or carrying instructions for execution by the device 3700 and that cause the device 3700 to perform any one or more of the techniques (e.g., processes) of the present disclosure, or that is capable of storing, encoding or carrying data structures used by or associated with such instructions. The term "machine-readable medium" shall accordingly be taken to include, but not be limited to, solid-state memories, and optical and magnetic media. Specific examples of machine-readable media can include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks. A machine readable medium does not include signals per se.

The instructions 3724 can further be transmitted or received over a communications network 3726 using a transmission medium via the network interface device 3720 utilizing any one of a number of transfer protocols (e.g., frame relay, internee protocol (IP), transmission control protocol (TCP), user datagram protocol (UDP), hypertext transfer protocol (HTTP), etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 3720 can include one or more physical jacks (e.g., Ethernet, coaxial, or phone jacks) or one or more antennas to connect to the communications network 3726. In an example, the network interface device 3720 can include a plurality of antennas to wirelessly communicate using at least one of single-input multiple-output (SMO), multiple-input multiple-output (MIMO), or multiple-input single-output (MISO) techniques. The term "transmission medium" shall be taken to include any intangible medium that is capable of storing, encoding or carrying instructions for execution by the device 3700, and includes digital or analog communications signals or other intangible medium to facilitate communication of such software.

Additional Notes and Examples

The description of embodiments can be better understood by some examples. The examples can include other subject matter disclosed herein.

Example 1 includes a method for altering patient care based on a standard deviation of deltas analysis, the method comprising receiving a measurement value of an analyte of a sample, a patient identification indicating a patient from which the sample was taken, a laboratory analyzer identification indicating a laboratory analyzer used to generate the measurement value, a time at which the measurement value was generated, and an analyte identification indicating a type of analyte to which the measurement value corresponds, identifying one or more demographics of the patient, retrieving measurement values of the analyte corresponding to the same laboratory analyzer or a group of laboratory analyzers, same analyte identification, and corresponding to patients with the same identified one or more demographics, generating a standard deviation of deltas (SDD) plot of the received and retrieved measurement values, determining whether the measurement value corresponds to a normal or abnormal condition based on the generated SDD plot, and altering patient care based on the determination of whether the measurement value corresponds to the normal or abnormal condition.

In Example 2, Example 1 can further include, wherein the demographics include two or more of sex, waist circumference, age, and weight.

In Example 3, Example 2 can further include, wherein each point of the standard deviation of deltas plot is determined for each of a plurality of respective time delta bins, as $$SDD = \sqrt{\frac{\sum (x_{i-1} - x_i)^2}{2n}},$$

where $x_i$ and $x_{i-1}$ are measurement values in a same time delta bin of the time delta bins.

In Example 4, at least one of Examples 1-3 can further include, wherein the SDD plot includes SDD values vs time between corresponding measurement values.

In Example 5, at least one of Examples 1-4 can further include, wherein altering patient care includes refraining from performing a measurement on a second sample of the patient in response to determining the measurement value corresponds to the normal condition.

In Example 6, at least one of Examples 1-5 can further include, wherein altering patient care includes ordering a measurement of the second sample of the patient on a different laboratory analyzer in response to determining the laboratory analyzer includes analytic variation that is too high to reliably determine whether the condition of the patient is normal or abnormal.

In Example 7, Example 6 can further include, wherein determining the laboratory analyzer includes analytic variation that is too high includes generating an SDD plot of quality control (QC) sample measurements performed by the laboratory analyzer, the measurements of the same analyte as the analyte of the sample of the patient.

In Example 8, at least one of Examples 1-7 can further include, wherein the analyte includes one or more of sodium, calcium, magnesium, potassium, hemoglobin A1c, troponin, chlorine, glucose, or white or red blood cells.

In Example 9, at least one of Examples 1-8 can further include, wherein altering patient care includes ordering a measurement of the second sample of the patient from a different laboratory technician in response to determining the laboratory technician is associated with an analyte variation that is too high to reliably determine whether the condition of the patient is normal or abnormal.

In Example 10, Example 9 can further include, wherein determining the laboratory analyzer includes analytic variation that is too high includes generating an SDD plot of sample measurements performed by the laboratory technician.

In Example 11, at least one of Examples 1-10 can further include, wherein altering the patient care includes adjusting an amount of medication or administering a new medication to the patient in response to determining the condition of the patient is abnormal.

In Example 12, at least one of Examples 1-11 can further include, wherein altering the patient care includes determining, based on SDD plots of patients that fast and SDD plots that do not fast before measurement values are determined, whether or not the patient is to fast or not before a next measurement of the analyte, and either refraining from fasting or fasting in response to determining the biologic variation is sufficiently different between patients that fast and patients that do not fast.

In Example 13, at least one of Examples 1-12 can further include, wherein determining whether the measurement value corresponds to a normal or abnormal condition based on the generated SDD plot includes comparing the variation in the patient to a variation in patients of a variety of percentile ranges including low percentile variation, middle percentile variation, and high percentile variation.

Example 14 can include a non-transitory machine-readable medium including instructions that, when executed by a machine, cause the machine to perform the method of at least one of Examples 1-13.

Example 15 can include a system or device configured to implement method of at least one of Examples 1-13.

The above detailed description includes references to the accompanying drawings, which form a part of the detailed description. The drawings show, by way of illustration, specific embodiments in which methods, apparatuses, and systems discussed herein may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

As used herein, a "-" (dash) used when referring to a reference number means "or", in the non-exclusive sense discussed in the previous paragraph, of all elements within the range indicated by the dash. For example, 103A-B means a nonexclusive "or" of the elements in the range {103A, 103B}, such that 103A-103B includes "103A but not 103B", "103B but not 103A", and "103A and 103B".

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

What is claimed is:

1. A method for altering patient care based on a standard deviation of deltas (SDD) analysis, the method comprising:
   receiving a measurement value of an analyte of a sample, a patient identification indicating a patient from which the sample was taken, a laboratory analyzer identification indicating a laboratory analyzer used to generate the measurement value, a time at which the measurement value was generated, and an analyte identification indicating a type of analyte to which the measurement value corresponds;
   identifying one or more demographics of the patient;
   retrieving measurement values of the analyte corresponding to the same laboratory analyzer or a group of laboratory analyzers, same analyte identification, and corresponding to patients with the same identified one or more demographics;
   generating an SDD plot of the received and retrieved measurement values, the SDD plot presenting SDD values for deltas values between measurement values taken greater than one month apart and including data points representing a respective SDD value determined for delta values between measurement values in each of a plurality of time delta bins, the time delta bins arranged by day increments and ranging from one day to more than one month;
   determining the laboratory analyzer is operating abnormally based on the generated SDD plot; and
   calibrating the laboratory analyzer in response to determining the laboratory analyzer is operating abnormally.

2. The method of claim 1, wherein the demographics include two or more of sex, waist circumference, age, and weight.

3. The method of claim 2, wherein each point of the SDD plot is determined for each of the plurality of respective time delta bins, as $$SDD = \sqrt{\frac{\sum (x_{i-1} - x_i)^2}{2n}},$$

where xi and xi−1 are measurement values in a same time delta bin of the time delta bins.

4. The method of claim 3, wherein the SDD plot includes SDD values vs time between corresponding measurement values.

5. The method of claim 1, wherein altering patient care includes refraining from performing a measurement on a second sample of the patient in response to determining the measurement value corresponds to a normal condition.

6. The method of claim 1, wherein altering patient care includes ordering a measurement of the second sample of the patient on a different laboratory analyzer in response to determining the laboratory analyzer includes analytic variation that is too high to reliably determine whether the condition of the patient is normal or abnormal.

7. The method of claim 6, wherein determining the laboratory analyzer includes analytic variation that is too high includes generating an SDD plot of quality control (QC) sample measurements performed by the laboratory analyzer, the measurements of the same analyte as the analyte of the sample of the patient.

8. The method of claim 1, wherein the analyte includes one or more of sodium, calcium, magnesium, potassium, hemoglobin A1c, troponin, chlorine, glucose, or white or red blood cells.

9. The method of claim 1, further comprising altering patient care by ordering a measurement of the second sample of the patient from a different laboratory technician in response to determining the laboratory technician is associated with an analyte variation that is too high to reliably determine whether a condition of the patient is normal or abnormal.

10. The method of claim 9, wherein determining the laboratory analyzer includes analytic variation that is too high includes generating an SDD plot of sample measurements performed by the laboratory technician.

11. The method of claim 1, further comprising altering patient care by adjusting an amount of medication or administering a new medication to the patient in response to determining a condition of the patient is abnormal.

12. The method of claim 1, further comprising altering patient care by determining, based on SDD plots of patients that fast and SDD plots that do not fast before measurement values are determined, whether or not the patient is to fast or not before a next measurement of the analyte, and either refraining from fasting or fasting in response to determining the biologic variation is sufficiently different between patients that fast and patients that do not fast.

13. The method of claim 1, further comprising determining whether the measurement value corresponds to a normal or abnormal condition in the patient based on the generated SDD plot including comparing the variation in the patient to a variation in patients of a variety of percentile ranges including low percentile variation, middle percentile variation, and high percentile variation.

14. A non-transitory machine-readable medium including instructions stored thereon that, when executed by a machine, cause the machine to perform operations comprising:
- receiving a measurement value of an analyte of a sample, a patient identification indicating a patient from which the sample was taken, a laboratory analyzer identification indicating a laboratory analyzer used to generate the measurement value, a time at which the measurement value was generated, and an analyte identification indicating a type of analyte to which the measurement value corresponds;
- identifying one or more demographics of the patient;
- retrieving measurement values of the analyte corresponding to the same laboratory analyzer or a group of laboratory analyzers, same analyte identification, and corresponding to patients with the same identified one or more demographics;
- generating a standard deviation of deltas (SDD) plot of the received and retrieved measurement values, the SDD plot presenting SDD values for deltas values between measurement values taken greater than one month apart and including data points representing a respective SDD value determined for delta values between measurement values in each of a plurality of time delta bins, the time delta bins arranged by day increments and ranging from one day to more than one month;
- determining the laboratory analyzer is operating abnormally based on the generated SDD plot; and
- causing calibration of the laboratory analyzer in response to determining the laboratory analyzer is operating abnormally.

15. The non-transitory machine-readable medium of claim 14, wherein the demographics include two or more of sex, waist circumference, age, and weight and, wherein each point of the SDD plot is determined for each of a plurality of respective time delta bins, as $$SDD = \sqrt{\frac{\Sigma(x_{i-1} - x_i)^2}{2n}},$$

where $x_i$ and $x_{i-1}$ are measurement values in a same time delta bin of the time delta bins.

16. The non-transitory machine-readable medium of claim 14, further comprising altering patient care by refraining from performing a measurement on a second sample of the patient in response to determining the measurement value corresponds to a normal condition.

17. The non-transitory machine-readable medium of claim 14, further comprising altering patient care by ordering a measurement of the second sample of the patient on a different laboratory analyzer in response to determining the laboratory analyzer includes analytic variation that is too high to reliably determine whether a condition of the patient is normal or abnormal.

18. The non-transitory machine-readable medium of claim 17, wherein determining the laboratory analyzer includes analytic variation that is too high includes generating an SDD plot of sample measurements performed by the laboratory analyzer on a quality control (QC) sample, the measurements of the same analyte as the analyte of the sample of the patient.

19. The non-transitory machine-readable medium of claim 14, further comprising altering patient care includes ordering a measurement of the second sample of the patient from a different laboratory technician in response to determining the laboratory technician is associated with an analyte variation that is too high to reliably determine whether a condition of the patient is normal or abnormal.

20. The non-transitory machine-readable medium of claim 19, wherein determining the laboratory analyzer includes analytic variation that is too high includes generating an SDD plot of sample measurements performed by the laboratory technician.

* * * * *